(12) United States Patent
Lee et al.

(10) Patent No.: US 11,499,149 B2
(45) Date of Patent: Nov. 15, 2022

(54) DONOR REPAIR TEMPLATES MULTIPLEX GENOME EDITING

(71) Applicant: 2seventy bio, Inc., Cambridge, MA (US)

(72) Inventors: Baeckseung Lee, Kenmore, WA (US); Alexander Astrakhan, Seattle, WA (US)

(73) Assignee: 2seventy bio, Inc., Cambridge, MA (US)

( * ) Notice: Subject to any disclaimer, the term of this patent is extended or adjusted under 35 U.S.C. 154(b) by 422 days.

(21) Appl. No.: 16/485,345

(22) PCT Filed: Feb. 15, 2018

(86) PCT No.: PCT/US2018/018370
§ 371 (c)(1),
(2) Date: Aug. 12, 2019

(87) PCT Pub. No.: WO2018/152325
PCT Pub. Date: Aug. 23, 2018

(65) Prior Publication Data
US 2019/0390189 A1 Dec. 26, 2019

Related U.S. Application Data

(60) Provisional application No. 62/459,203, filed on Feb. 15, 2017.

(51) Int. Cl.
*C12N 15/90* (2006.01)
*C12N 15/10* (2006.01)
(Continued)

(52) U.S. Cl.
CPC ............ *C12N 15/102* (2013.01); *A61K 35/17* (2013.01); *C07K 14/7051* (2013.01);
(Continued)

(58) Field of Classification Search
CPC ............................... C12N 15/90; C12N 15/85
See application file for complete search history.

(56) References Cited

U.S. PATENT DOCUMENTS 5,786,538 A 7/1998 Barone
5,994,136 A 11/1999 Naldini et al.
(Continued)

FOREIGN PATENT DOCUMENTS

GB 2531454 A 4/2016
WO WO 2006/010834 A1 2/2006
(Continued)

OTHER PUBLICATIONS

Albert, et al., "Site-specific integration of DNA into wild-type and mutant lox sites placed in the plant genome." Plant J. (1995); 7(4): 649-659.
(Continued)

*Primary Examiner* — Karen Cochrane Carlson
(74) *Attorney, Agent, or Firm* — Panitch Schwarze Belisario & Nadel LLP; Stephany G. Small; Travis W. Bliss

(57) ABSTRACT

The present disclosure provides improved multiplex genome editing compositions and methods. The disclosure further provides genome edited cells for the prevention, treatment, or amelioration of at least one symptom of a hemoglobinopathy, a cancer, an infectious disease, an autoimmune disease, an inflammatory disease, or an immunodeficiency.

19 Claims, 7 Drawing Sheets

Specification includes a Sequence Listing.

Gene A homology arms
 Gene B homology arms
 Insert with or without its own promoter Two different inner and outer arm sets Two different inner and outer arm sets Alternatively positioned two different arm sets Two different inserts and two different arm sets

(51) Int. Cl.
| | |
|---|---|
| A61K 35/17 | (2015.01) |
| C07K 14/725 | (2006.01) |
| C07K 14/705 | (2006.01) |
| C07K 16/28 | (2006.01) |
| C12N 9/22 | (2006.01) |
| C12N 15/66 | (2006.01) |
| C12N 15/86 | (2006.01) |
| A61K 38/00 | (2006.01) |

(52) U.S. Cl.
CPC .. *C07K 14/70517* (2013.01); *C07K 14/70521* (2013.01); *C07K 14/70578* (2013.01); *C07K 16/2878* (2013.01); *C12N 9/22* (2013.01); *C12N 15/66* (2013.01); *C12N 15/86* (2013.01); *A61K 38/00* (2013.01); *C07K 2317/622* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2740/15043* (2013.01); *C12N 2750/14143* (2013.01); *C12N 2830/50* (2013.01)

(56) References Cited

U.S. PATENT DOCUMENTS

| | | | |
|---|---|---|---|
| 6,013,516 | A | 1/2000 | Verma et al. |
| 6,682,907 | B1 | 1/2004 | Charneau et al. |
| 8,614,092 | B2 | 12/2013 | Zhang et al. |
| 8,784,799 | B2 | 7/2014 | Samulski et al. |
| 8,809,058 | B2 | 8/2014 | Ferrari et al. |
| 8,889,641 | B2 | 11/2014 | Asokan et al. |
| 9,012,224 | B2 | 4/2015 | Bowles et al. |
| 9,017,967 | B2 | 4/2015 | Bonas et al. |
| 9,169,492 | B2 | 10/2015 | Monahan et al. |
| 9,169,494 | B2 | 10/2015 | Hewitt et al. |
| 2016/0145646 | A1 | 5/2016 | Lai et al. |

FOREIGN PATENT DOCUMENTS

| | | |
|---|---|---|
| WO | 2014184741 A1 | 11/2014 |
| WO | WO 2015/168125 A1 | 11/2015 |
| WO | WO 2016/176690 A2 | 11/2016 |
| WO | WO 2017/156484 A1 | 9/2017 |
| WO | WO 2017/177137 A1 | 10/2017 |
| WO | WO 2018/035423 A1 | 2/2018 |
| WO | WO 2018/049226 A1 | 3/2018 |

OTHER PUBLICATIONS

Altschul, S. et al., "Gapped BLAST and PSI-BLAST: a new generation of protein database search programs", Nucleic Acids Res (1997);25(17):3389-402.

Ausubel et al., "Current Protocols in Molecular Biology," John Wiley & Sons Inc, 1994-1998, Chapter 15, 31 pages.

Belteki, et al., "Site-specific cassette exchange and germline transmission with mouse ES cells expressing φ31 integrase." Nature Biotechnology (2003); 21: 321-324.

Bethke et al., "Segmental genomic replacement by Cre-mediated recombination: genotoxic stress activation of the p53 promoter in single-copy transformants." Nucleic Acids Research (1997); 25(14): 2828-2834.

Boissel et al., "megaTALs: a rare-cleaving nuclease architecture for therapeutic genome engineering," Nucleic Acids Research, 2013, 42(4):2591-2601.

Choo et al., "Toward a code for the interactions of zinc fingers with DNA: selection of randomized fingers displayed on phage," Proc Natl Acad Sci USA. Nov. 8, 1994;91(23):11163-7.

Choo et al., "Selection of DNA binding sites for zinc fingers using rationally randomized DNA reveals coded interactions," Proc Natl Acad Sci USA. Nov. 8, 1994;91(23):11168-72.

Christian et al., "Targeting DNA Double-Strand Breaks with TAL Effector Nucleases," Genetics. Oct. 2010;186(2):757-61.

Clever, J. et al., "RNA Secondary Structure and Binding Sites for gag Gene Products in the 5' Packaging Signal of Human Immunodeficiency Virus Type 1." J. of Virology (1995); 69(4): 2101-2109.

Cong et al., "Multiplex Genome Engineering Using CRISPR/Cas Systems," Science 2013, 339:819-823.

Cullen et al., "Regulatory Pathways Governing HIV-1 Replication", Cell (1989); 58: 423-426.

Cullen, B.R., "Human Immunodeficiency Virus as a Prototypic Complex Retrovirus", Journal of Virology (1991); 65(3): 1053-1056.

Desjarlais et al., "Use of a zinc-finger consensus sequence framework and specificity rules to design specific DNA binding proteins." Proceedings of the National Academy of Sciences (1993); 90.6: 2256-2260.

Desjarlais et al., "Toward rules relating zinc finger protein sequences and DNA binding site preferences," Proc Natl Acad Sci USA. Aug. 15, 1992;89(16):7345-9.

Desjarlais et al., "Length-encoded multiplex binding site determination: application to zinc finger proteins," Proceedings of the National Academy of Sciences (1994); 91.23: 11099-11103.

Dull et al., "A third-generation lentivirus vector with a conditional packaging system", Journal of Virology (1998); 72(11): 8463-8671.

Esvelt et al., "Orthogonal Cas9 proteins for RNA-guided gene regulation and editing," Nat Methods. Nov. 2013;10(11):1116-21.

Extended European Search Report dated Nov. 12, 2020, for European Application No. 18755081.9, 8 pages.

Fok et al., Multiplexed CRISPR/Cas9 genome editing increases the efficacy of homologous-dependent repair of donor sequences in mammalian cells, South African Journal of Science, vol. 111, No. 7-8, Jul. 2015.

Gomez-Foix et al, "Adenovirus-mediated Transfer of the Muscle Glycogen Phosphorylase Gene into Hepatocytes Confers Altered Regulation of Glycogen Metabolism," J Biol Chem. Dec. 15, 1992;267(35):25129-34.

Graham et al., "Characteristics of a Human Cell Line Transformed by DNA from Human Adenovirus Type 5," J. gen. Virol. 1977, 36, 59-72.

Graham & Preveck, "Chapter 11, Manipulation of Adenovirus Vectors," Methods in Molecular Biology, vol. 7: Gene transfer and Expression Protocols, 1991.

Graham & Preveck, "Adenovirus-Based Expression Vectors and Recombinant Vaccines" Vaccines: New Approaches to Immunological Problems, 1992.

Greisman et al., "A general strategy for selecting high-affinity zinc finger proteins for diverse DNA target sites," Science. Jan. 31, 1997;275(5300):657-61.

Groth, et al., "A phage integrase directs efficient site-specific integration in human cells." PNAS (2000); 97(11): 5995-6000.

Grunhaus, A., and Horwitz, M. S. "Adenoviruses as cloning vectors," Semin. Virol. 1992; 3, 237-252.

Herz & Gerard, "Adenovirus-mediated transfer of low density lipoprotein receptor gene acutely accelerates cholesterol clearance in normal mice," PNAS, 1993, vol. 90, 2812-2816.

Hoess, et al., "The role of the loxP spacer region in P1 site-specific recombination," Nucleic Acids Res, 14 (1986), pp. 2287-2300.

Huang et al., "Role of the hepatitis B virus posttranscriptional regulatory element in export of intronless transcripts," Molecular and Cellular Biology (1995); 15(7): 3864-3869.

Ibarra et al., "Efficient Modification of the CCR5 Locus in Primary Human T Cells With megaTAL Nuclease Establishes HIV-1 Resistance," Molecular Therapy—Nucleic Acids, Aug. 23, 2016, vol. 5, No. 8, pp. 1-10.

International Search Report and Written Opinion dated May 8, 2018, for International Application No. PCT/US2018/018370, 9 pages.

Jamieson et al., "In vitro selection of zinc fingers with altered DNA-binding specificity," Biochemistry. May 17, 1994;33(19):5689-95.

Jarjour et al., "High-resolution profiling of homing endonuclease binding and catalytic specificity using yeast surface display," 2009. Nuc. Acids Res. 37(20): 6871-6880.

(56) References Cited

OTHER PUBLICATIONS

Jinek et al., "A programmable dual RNA-guided DNA endonuclease in adaptive bacterial immunity," Science 2012, 337(6096): 816-821.
Jinek et al., "RNA-programmed genome editing in human cells," Elife. Jan. 29, 2013;2:e00471.
Jones & Shenk, Isolation of Deletion and Substitution Mutants of Adenovirus Type 5, Cell 1978, vol. 13, 181-188.
Kay et al., "A bacterial effector acts as a plant transcription factor and induces a cell size regulator," Science. Oct. 26, 2007;318(5850):648-51.
Kutner, et al., "Simplified production andconcentration of HIV-1-based lentiviral vectors using HYPERFlask vessels and anion exchange membrane chromatography", BMC Biotechnol. (2009); 9:10. p. 1-7.
Kutner et al., "Production, concentration and titration of pseudotyped HIV-1-based lentiviral vectors", Nature Protocols (2009); 4: 495-505.
Langer, et al., "A genetic screen identifies novel non-compatible loxP sites," Nucleic Acids Res, 30 (2002), pp. 3067-3077.
Lee et al., "Role of nucleotide sequences of loxP spacer region in Cre-mediated recombination." Gene (1998); 216 (1): 55-65.
Le Gal La Salle et al., "An Adenovirus Vector for Gene Transfer into Neurons and Glia in the Brain," Science Feb. 12, 1993, vol. 259, 988-990.
Levrero et al., "Defective and nondefective adenovirus vectors for expressing foreign genes in vitro and in vivo," Gene 1991; 101:195-202.
Liu et al., "HnRNP L binds a cis-acting RNA sequence element that enables intron-dependent gene expression," Genes & Dev. (1995); 9: 1766-1780.
Liu et al., "Design of polydactyl zinc-finger proteins for unique addressing within complex genomes," Proceedings of the National Academy of Sciences (1997); 94.11: 5525-5530.
MacLeod et al., "Integration of a CD19 CAR into the TCR Alpha Chain Locus Streamlines Production of Allogeneic Gene-Edited CAR T Cells", Molecular Therapy, vol. 25, No. 4, Feb. 9, 2017, pp. 949-961.
McLeod, et al., "Identification of the crossover site during FLP-mediated recombination in the *Saccharomyces cerevisiae* plasmid 2 microns circle," Mol. Cell. Biol, vol. 6, No. 10, Oct. 1986, pp. 3357-3367.
Mali et al., "RNA-Guided Human Genome Engineering via Cas9," Science. Feb. 15, 2013; 339(6121): 823-826.
Naldini L. et al., "Efficient transfer, integration, and sustained long-term expression of the transgene in adult rat brains injected with a lentiviral vector", Proc Natl Acad Sci USA (1996); 93(21): 11382-11388.
Naldini, L. et al., "In vivo gene delivery and stable transduction of nondividing cells by a lentiviral vector", Science (1996); 272(5259): 263-267.
Naldini, L., "Lentiviruses as gene transfer agents for delivery to non-dividing cells", Curr Opin Biotechnol. (1998); 5: 457-463.
Pomerantz, et al., "Structure-based design of transcription factors." Science (1995); 267.5194: 93-96.
Pomerantz, et al., "Analysis of homeodomain function by structure-based design of a transcription factor," Proc Natl Acad Sci USA. Oct. 10, 1995;92(21):9752-6.
Qi et al., "Repurposing CRISPR as an RNA-guided platform for sequence-specific control of gene expression," Cell. Feb. 28, 2013; 152(5):1173-83.
Ragot et al., "Efficient adenovirus-mediated transfer of a human minidystrophin gene to skeletal muscle of mdx mice," Nature Feb. 18, 1993; vol. 361: 647-650.
Ran et al., "Genome engineering using the CRISPR-Cas9 system," Nat Protoc. Nov. 2013;8(11):2281-2308.
Rebar et al., "Zinc finger phage: affinity selection of fingers with new DNA-binding specificities," Science. Feb. 4, 1994;263(5147):671-3.
Rosenfeld et al., "Adenovirus-Mediated Transfer of a Recombinant α1-Antitrypsin Gene to the Lung Epithelium in Vivo," Science Apr. 19, 1991; vol. 252: 431-434.
Rosenfeld et al., "In vivo transfer of the human cystic fibrosis transmembrane conductance regulator gene to the airway epithelium," Cell, Jan. 10, 1992; vol. 68: 143-155.
Sauer, B. "Site-specific recombination: developments and applications", Curr Opin Biotechnol. (1994); 5(5): 521-7.
Schlake et al., "Use of mutated FLP recognition target (FRT) sites for the exchange of expression cassettes at defined chromosomal loci." Biochemistry (1994); 33(43): 12746-12751.
Segal, "Bacteria herald a new era of gene editing," Elife. Jan. 29, 2013;2:e00563.
Senecoff, et al., "DNA Recognition by the FLP Recombinase of the Yeast 2 μ Plasmid." J. Mol. Biol. (1988); 201 (2): 405-421.
Stoddard, "Homing endonuclease structure and function," Quarterly Reviews of Biophysics 2005; 38(1): pp. 49-95.
Sterman et al., "Adenovirus-mediated herpes simplex virus thymidine kinase/ganciclovirgene therapy in patients with localized malignancy: results of a phase I clinical trial in malignant mesothelioma," Hum Gene Ther. May 1, 1998;9(7):1083-92.
Takeuchi et al., "Tapping natural reservoirs of homing endonucleases for targeted gene modification," 2011. Proc Natl Acad Sci U. S. A. Aug. 9, 2011; 108(32): 13077-13082.
Thyagarajan, et al., "Site-specific genomic integration in mammalian cells mediated by phage phiC31 integrase." Mol Cell Biol. (2001); 21(12): 3926-3934.
Wu et al., "Building zinc fingers by selection: toward a therapeutic application," Proc Natl Acad Sci USA. Jan. 17, 1995;92(2):344-8.
Zennou et al., "HIV-1 genome nuclear import is mediated by a central DNA flap," Cell. Apr. 14, 2000;101(2):173-85.
Zetsche et al., "Cpf1 is a single RNA-guided endonuclease of a class 2 CRISPR-Cas system," Cell. Oct. 22, 2015;163(3):759-71.
Zufferey et al., "Multiply attenuated lentiviral vector achieves efficient gene delivery in vivo", Nat Biotechnol. (1997), 15(9): 871-875.
Zufferey, R. et al., "Woodchuck hepatitis virus posttranscriptional regulatory element enhances expression of transgenes delivered by retroviral vectors." J Virol. (1999); 73(4): 2886-2892.
Dunin-Horkawicz, S. et al., "Phylogenomic analysis of the GIY-YIG nuclease superfamily," BMC Genomics, vol. 7:98, 19 pages, Apr. 28, 2006.
Hensgens, L. et al., "Two Intron Sequences in Yeast Mitochondrial COX1 Gene: Homology among URF-Containing Introns and Strain-Dependent Variation in Flanking Exons," Cell, vol. 32, 379-389, Feb. 1983.
Office Action dated Jul. 22, 2022 in EP Application No. 18755081.9.
Office Action dated Jul. 5, 2022 in JP Application No. 2019564394.

SEQUENCE LISTING

```
<160> NUMBER OF SEQ ID NOS: 40

<210> SEQ ID NO 1
<211> LENGTH: 7317
<212> TYPE: DNA
<213> ORGANISM: Artificial Sequence
<220> FEATURE:
<223> OTHER INFORMATION: Synthesized sequence pBW1411

<400> SEQUENCE: 1
cagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120
actaggggtt ccttgtagtt aatgattaac ccgccatgct acttatctac gtaaggctgt     180
tgcaggcatc acacggtgga aagatctgga actgtggcca tggtgtgagg ccatccacaa     240
ggtggaagct ttgaggggga gccgattagc catggacagt tgtcattcag tagggtcacc     300
tgtgccccag cgaaggggga tgggccggga aggcagaggc caggcacctg cccccagcag     360
gggcagaggc tgtgggcagc cgggaggctc ccagaggctc cgacagaatg ggagtggggt     420
tgagcccacc cctcactgca gcccaggaac ctgagcccag aggggccac ccaccttccc      480 caggcaggga ggcccggccc ccagggagat ggggggggatg ggggaggaga agggcctgcc     540
cccacccggc agcctcagga ggggcagctc gggcgggata tggaaagagg ccacagcagt     600
gagcagagac acagaggagg aagggccct gagctgggga gacccccacg gggtagggcg      660
tgggggccac gggcccacct cctcccccatc tcctctgtct ccctgtctct gtctctctct     720
ccctccccca ccctctcccc agtcctaccc cctcctcacc cctcctcccc cagcactgcc     780
tctgtcactc tcgcccacgt ggatgtggag gaagagggg cgggagcaag gggcgggcac      840 cctccttca acctgacctg ggacagtttc ccttccgctc acctccgcct gagcagtgga     900
gaaggcggca ctctggtggg gctgctccaa atcatggcct cttggccaag attgatagct     960
tgtgcctgtc cctgagtccc agtccatcac gagcagctgg tttctaagat gctatttccc    1020
gtataaagca tgagaccgtg acttgccagc cccacagagc cccgcccttg tccatcactg    1080
gcatctggac tccagcctgg gttggggcaa agagggaaat gagatcatgt cctaaccctg    1140
atcctcttgt cccacagata tccagaaccc tgaccctgcc gtgtaccagc tgagagactc    1200
taaatccagt gacaagtctg tctgcctatc gcgtgaacag agaaacagga gaatatgggc    1260
caaacaggat atctgtggta agcagttcct gccccggctc agggccaaga acagttggaa    1320
```

```
cagcagaata tgggccaaac aggatatctg tggtaagcag ttcctgcccc ggctcagggc   1380
caagaacaga tggtccccag atgcggtccc gccctcagca gtttctagag aaccatcaga   1440
tgtttccagg gtgccccaag gacctgaaat gaccctgtgc cttatttgaa ctaaccaatc   1500
agttcgcttc tcgcttctgt tcgcgcgctt ctgctcccg agctctatat aagcagagct    1560
cgtttagtga accgtcagat cgcctggaga cgccatccac gctgttttga cttccataga   1620
aggatctcga ggccaccatg gtgagcaagg gcgaggagct gttcaccggg gtggtgccca   1680
tcctggtcga gctggacggc gacgtaaacg gccacaagtt cagcgtgtcc ggcgagggcg   1740
agggcgatgc cacctacggc aagctgaccc tgaagttcat ctgcaccacc ggcaagctgc   1800
ccgtgccctg gcccaccctc gtgaccaccc tgacctacgg cgtgcagtgc ttcagccgct   1860
accccgacca catgaagcag cacgacttct tcaagtccgc catgcccgaa ggctacgtcc   1920
aggagcgcac catcttcttc aaggacgacg gcaactacaa gacccgcgcc gaggtgaagt   1980
tcgagggcga caccctggtg aaccgcatcg agctgaaggg catcgacttc aaggaggacg   2040
gcaacatcct ggggcacaag ctggagtaca actacaacag ccacaacgtc tatatcatgg   2100
ccgacaagca gaagaacggc atcaaggtga acttcaagat ccgccacaac atcgaggacg   2160
gcagcgtgca gctcgccgac cactaccagc agaacacccc catcggcgac ggccccgtgc   2220
tgctgcccga caaccactac ctgagcaccc agtccgccct gagcaaagac cccaacgaga   2280
agcgcgatca catggtcctg ctggagttcg tgaccgccgc cgggatcact ctcggcatgg   2340
acgagctgta caagtaagcg gccgcgcttt atttgtgaaa tttgtgatgc tattgcttta   2400
tttgtaacca ttataagctg caataaacaa gttaacaaca caattgcat tcattttatg    2460 tttcaggttc aggggggagat gtgggaggtt ttttaaagcc tctttgattc tcaaacaaat   2520
gtgtcacaaa gtaaggattc tgatgtgtat atcacagaca aaactgtgct agacatgagg   2580
tctatggact tcaagagcaa cagtgctgtg gcctggagca caaatctga ctttgcatgt    2640 gcaaacgcct tcaacaacag cattattcca gaagacacct tcttccccag cccaggtaag   2700
ggcagctttg gtgccttcgc aggctgtttc cttgcttcag gaatggccag gttctgccca   2760
gagctctggt caatgatgtc taaaactcct ctgattggtg gtaccggttc tgggcggtgc   2820
tacaactggg ctggcggcca ggatggttct taggtaggtg gggtcggcgg tcaggtgtcc   2880
cagagccagg ggtctggagg gaccttccac cctcagtccc tggcaggtcg ggggggtgctg    2940 aggcgggcct ggccctggca gcccaggggt cccggagcga ggggtctgga gggacctttc    3000
actctcagtc cctggcaggt cggggggtgc tgtggcaggc ccagccttgg cccccagctc    3060
tgccccttac cctgagctgt gtggctttgg gcagctcgaa ctcctgggtt cctctctggg    3120
ccccaactcc tccctggcc caagtcccct ctttgctcct gggcaggcag acctctgtc     3180 ccctctcagc cggtccttgg ggctgcgtgt ttctgtagaa tgacgggtca ggctggccag   3240
aaccccaaac cttggccgtg gggagtctgc gtggcggctc tgccttgccc aggcatcctt   3300
ggtcctcact cgagttttcc taaggatggg atgagcccca tgtgggacta accttggctt   3360
tacgacgtca aagtttagat gagctggtga tattttctc attatatcca aagtgtacct    3420
gttcgagtga ggacagttct tctgtctcca ggatccctcc tgggtgggga ttgtgcccgc   3480
ctgggtctct gcccagattc cagggctctc cccgagccct gttcagacca tccgtggggg   3540
aggccttggc ctcactctta cgtagataag tagcatggcg ggttaatcat taactacaag   3600
gaacccctag tgatggagtt ggccactccc tctctgcgcg ctcgctcgct cactgaggcc   3660
```

```
gggcgaccaa aggtcgcccg acgcccgggc tttgcccggg cggcctcagt gagcgagcga   3720
gcgcgccagc tggcgtaata gcgaagaggc ccgcaccgat cgcccttccc aacagttgcg   3780
cagcctgaat ggcgaatggc gattccgttg caatggctgg cggtaatatt gttctggata   3840
ttaccagcaa ggccgatagt ttgagttctt ctactcaggc aagtgatgtt attactaatc   3900
aaagaagtat tgcgacaacg gttaatttgc gtgatggaca gactctttta ctcggtggcc   3960
tcactgatta taaaaacact tctcaggatt ctggcgtacc gttcctgtct aaaatccctt   4020
taatcggcct cctgtttagc tcccgctctg attctaacga ggaaagcacg ttatacgtgc   4080
tcgtcaaagc aaccatagta cgcgccctgt agcggcgcat taagcgcggc gggtgtggtg   4140
gttacgcgca gcgtgaccgc tacacttgcc agcgccctag cgcccgctcc tttcgctttc   4200
ttcccttcct ttctcgccac gttcgccggc tttccccgtc aagctctaaa tcggggctc    4260
cctttagggt tccgatttag tgctttacgg cacctcgacc ccaaaaaact tgattagggt   4320
gatggttcac gtagtgggcc atcgccctga tagacggttt ttcgcccttt gacgttggag   4380
tccacgttct ttaatagtgg actcttgttc caaactggaa caacactcaa ccctatctcg   4440
gtctattctt ttgatttata agggattttg ccgatttcgg cctattggtt aaaaaatgag   4500
ctgatttaac aaaaatttaa cgcgaatttt aacaaaatat taacgtttac aatttaaata   4560
tttgcttata caatcttcct gttttttgggg cttttctgat tatcaaccgg ggtacatatg   4620
attgacatgc tagttttacg attaccgttc atcgattctc ttgtttgctc cagactctca   4680
ggcaatgacc tgatagcctt tgtagagacc tctcaaaaat agctaccctc tccggcatga   4740
atttatcagc tagaacggtt gaatatcata ttgatggtga tttgactgtc tccggccttt   4800
ctcacccgtt tgaatcttta cctacacatt actcaggcat tgcatttaaa atatatgagg   4860
gttctaaaaa ttttatcct tgcgttgaaa taaaggcttc tcccgcaaaa gtattacagg   4920
gtcataatgt ttttggtaca accgatttag ctttatgctc tgaggcttta ttgcttaatt   4980
ttgctaattc tttgccttgc ctgtatgatt tattggatgt tggaatcgcc tgatgcggta   5040
ttttctcctt acgcatctgt gcggtatttc acaccgcata tggtgcactc tcagtacaat   5100
ctgctctgat gccgcatagt taagccagcc ccgacacccg ccaacacccg ctgacgcgcc   5160
ctgacgggct tgtctgctcc cggcatccgc ttacagacaa gctgtgaccg tctccgggag   5220
ctgcatgtgt cagaggtttt caccgtcatc accgaaacgc gcgagacgaa agggcctcgt   5280
gatacgccta ttttttatagg ttaatgtcat gataataatg gtttcttaga cgtcaggtgg   5340
cacttttcgg ggaaatgtgc gcggaacccc tatttgttta ttttttctaaa tacattcaaa   5400
tatgtatccg ctcatgagac aataaccctg ataaatgctt caataatatt gaaaaaggaa   5460
gagtatgagt attcaacatt tccgtgtcgc ccttattccc ttttttgcgg cattttgcct   5520
tcctgttttt gctcacccag aaacgctggt gaaagtaaaa gatgctgaag atcagttggg   5580
tgcacgagtg ggttacatcg aactggatct caacagcggt aagatccttg agagttttcg   5640
ccccgaagaa cgttttccaa tgatgagcac ttttaaagtt ctgctatgtg gcgcggtatt   5700
atcccgtatt gacgccgggc aagagcaact cggtcgccgc atacactatt ctcagaatga   5760
cttggttgag tactcaccag tcacagaaaa gcatcttacg gatggcatga cagtaagaga   5820
attatgcagt gctgccataa ccatgagtga taacactgcg gccaacttac ttctgacaac   5880
gatcggagga ccgaaggagc taaccgcttt tttgcacaac atgggggatc atgtaactcg   5940
ccttgatcgt tgggaaccgg agctgaatga agccatacca aacgacgagc gtgacaccac   6000
gatgcctgta gcaatggcaa caacgttgcg caaactatta actggcgaac tacttactct   6060
```

```
agcttcccgg caacaattaa tagactggat ggaggcggat aaagttgcag gaccacttct    6120
gcgctcggcc cttccggctg gctggtttat tgctgataaa tctggagccg gtgagcgtgg    6180
gtctcgcggt atcattgcag cactgggcc agatggtaag ccctcccgta tcgtagttat     6240
ctacacgacg gggagtcagg caactatgga tgaacgaaat agacagatcg ctgagatagg    6300
tgcctcactg attaagcatt ggtaactgtc agaccaagtt tactcatata tactttagat    6360
tgatttaaaa cttcattttt aatttaaaag gatctaggtg aagatccttt ttgataatct    6420
catgaccaaa atcccttaac gtgagttttc gttccactga gcgtcagacc ccgtagaaaa    6480
gatcaaagga tcttcttgag atccttttt tctgcgcgta atctgctgct tgcaaacaaa     6540
aaaaccaccg ctaccagcgg tggtttgttt gccggatcaa gagctaccaa ctcttttttcc   6600 gaaggtaact ggcttcagca gagcgcagat accaaatact gtccttctag tgtagccgta    6660
gttaggccac cacttcaaga actctgtagc accgcctaca tacctcgctc tgctaatcct    6720
gttaccagtg gctgctgcca gtggcgataa gtcgtgtctt accgggttgg actcaagacg    6780
atagttaccg gataaggcgc agcggtcggg ctgaacgggg ggttcgtgca cacagcccag    6840
cttggagcga acgacctaca ccgaactgag atacctacag cgtgagctat gagaaagcgc    6900
cacgcttccc gaagggagaa aggcggacag gtatccggta agcggcaggg tcggaacagg    6960
agagcgcacg agggagcttc cagggggaaa cgcctggtat ctttatagtc ctgtcgggtt    7020
tcgccacctc tgacttgagc gtcgatttt gtgatgctcg tcagggggc ggagcctatg      7080 gaaaaacgcc agcaacgcgg cctttttacg gttcctggcc ttttgctggc cttttgctca    7140
catgttcttt cctgcgttat cccctgattc tgtggataac cgtattaccg cctttgagtg    7200
agctgatacc gctcgccgca gccgaacgac cgagcgcagc gagtcagtga gcgaggaagc    7260
ggaagagcgc ccaatacgca aaccgcctct ccccgcgcgt tggccgattc attaatg       7317
```

<210> SEQ ID NO 2
<211> LENGTH: 7413
<212> TYPE: DNA
<213> ORGANISM: Artificial Sequence
<220> FEATURE:
<223> OTHER INFORMATION: Synthesized sequence pBW1490

<400> SEQUENCE: 2

```
cagctgcgcg ctcgctcgct cactgaggcc gcccgggcaa agcccgggcg tcgggcgacc      60
tttggtcgcc cggcctcagt gagcgagcga gcgcgcagag agggagtggc caactccatc     120 actagggtt cctgtagtt aatgattaac ccgccatgct acttatctac gtaatggggg       180
aggagaaggg cctgccccca cccggcagcc tcaggagggg cagctcgggc gggatatgga     240
aagaggccac agcagtgagc agagacacag aggaggaagg ggccctgagc tggggagacc     300
cccacggggt agggcgtggg ggccacgggc ccacctcctc ccatctcct ctgtctccct      360 gtctctgtct ctctctccct ccccaccct tccccagtc ctaccccctc ctcacccctc       420
ctcccccagc actgcctctg tcactctcgc ccacgtggat gtggaggaag aggggcggg     480 agcaaggggc gggcaccctc ccttcaacct gacctgggac agtttccctt ccgctcacct     540
ccgcctgagc agtggagaag gcggcactct ggtgggctg ctccaaatca tggcctcttg     600
gccaagattg atagcttgtg cctgtccctg agtcccagtc catcacgagc agctggtttc     660
taagatgcta tttcccgtat aaagcatgag accgtgactt gccagcccca cagagccccg     720 ccccttgtcca tcactggcat ctggactcca gcctgggttg gggcaaagag ggaaatgaga    780
```

-continued

```
tcatgtccta acccctgatcc tcttgtccca cagatatcca gaaccctgac cctgccgtgt    840
accagctgag agactctaaa tccagtgaca agtctgtctg cctatacgcg taatgaaaga    900
ccccacctgt aggtttggca agctaggatc aaggttagga acagagagac agcagaatat    960
gggccaaaca ggatatctgt ggtaagcagt tcctgccccg gctcagggcc aagaacagtt   1020
ggaacagcag aatatgggcc aaacaggata tctgtggtaa gcagttcctg ccccggctca   1080
gggccaagaa cagatggtcc ccagatgcgg tcccgccctc agcagtttct agagaaccat   1140
cagatgtttc cagggtgccc caaggacctg aaatgaccct gtgccttatt tgaactaacc   1200
aatcagttcg cttctcgctt ctgttcgcgc gcttctgctc cccgagctca ataaaagagc   1260
ccacaacccc tcactcggcg cgattcacct gcgcgtctac gccaccatgg cactccccgt   1320
caccgccctt ctcttgcccc tcgccctgct gctgcatgct gccaggcccg acattgtgct   1380
cactcagtca cctcccagcc tggccatgag cctgggaaaa agggccacca tctcctgtag   1440
agccagtgag tccgtcacaa tcttggggag ccatcttatt cactggtatc agcagaagcc   1500
cgggcagcct ccaacccttc ttattcagct cgcgtcaaac gtccgacgg gtgtacctgc    1560
cagattttct ggtagcgggt cccgcactga ttttacactg accatagatc cagtggaaga   1620
agacgatgtg ccgtgtatt attgtctgca gagcagaacg attcctcgca catttggtgg   1680
gggtactaag ctggagatta agggaagcac gtccggctca gggaagccgg gctccggcga   1740
gggaagcacg aaggggcaaa ttcagctggt ccagagcgga cctgagctga aaaacccgg   1800
cgagactgtt aagatcagtt gtaaagcatc tggctatacc ttcaccgact acagcataaa   1860
ttgggtgaaa cgggcccctg gaaagggcct caaatggatg ggttggatca ataccgaaac   1920
tagggagcct gcttatgcat atgacttccg cgggagattc gccttttcac tcgagacatc   1980
tgcctctact gcttacctcc aaataaacaa cctcaagtat gaagatacag ccacttactt   2040
ttgcgccctc gactatagtt acgccatgga ctactgggga cagggaaccct ccgttaccgt   2100
cagttccgcg gccgcaacca caacacctgc tccaaggccc cccacacccg ctccaactat   2160
agccagccaa ccattgagcc tcagacctga agcttgcagg cccgcagcag gaggcgccgt   2220
ccatacgcga ggcctggact tcgcgtgtga tatttatatt tgggcccctt tggccggaac   2280
atgtggggtg ttgcttctct cccttgtgat cactctgtat tgtaagcgcg ggagaaagaa   2340
gctcctgtac atcttcaagc agccttttat gcgacctgtg caaaccactc aggaagaaga   2400
tgggtgttca tgccgcttcc ccgaggagga agaaggaggg tgtgaactga gggtgaaatt   2460
ttctagaagc gccgatgctc ccgcatatca gcagggtcag aatcagctct acaatgaatt   2520
gaatctcggc aggcgagaag agtacgatgt tctggacaag agacggggca gggatcccga   2580
gatgggggga aagccccgga gaaaaaatcc tcaggagggg ttgtacaatg agctgcagaa   2640
ggacaagatg gctgaagcct atagcgagat cggaatgaaa ggcgaaagac gcagaggcaa   2700
ggggcatgac ggtctgtacc agggtctctc tacagccacc aaggcacttt atgatgcgtt   2760
gcatatgcaa gccttgccac cccgctaagc ggccgcgctt tatttgtgaa atttgtgatg   2820
ctattgcttt atttgtaacc attataagct gcaataaaca agttaacaac aacaattgca   2880
ttcattttat gtttcaggtt caggggagat gtgggaggt tttttaaagc tcaccggttt   2940
tgattctcaa acaaatgtgt cacaaagtaa ggattctgat gtgtatatca cagacaaaac   3000
tgtgctagac atgaggtcta tggacttcaa gagcaacagt gctgtggcct ggagcaacaa   3060
atctgacttt gcatgtgcaa acgccttcaa caacagcatt attccagaag acaccttctt   3120
ccccagccca ggtaagggca gctttggtgc cttcgcaggc tgtttccttg cttcaggaat   3180
```

```
ggccaggttc tgcccagagc tctggtcaat gatgtctaaa actcctctga ttggtggtac    3240
cggttctggg cggtgctaca actgggctgg cggccaggat ggttcttagg taggtggggt    3300
cggcggtcag gtgtcccaga gccagggg tc tggagggacc ttccaccctc agtccctggc    3360
aggtcggggg gtgctgaggc gggcctggcc ctggcagccc aggggtcccg gagcgagggg    3420
tctggaggga cctttcactc tcagtccctg gcaggtcggg gggtgctgtg gcaggcccag    3480
ccttggcccc cagctctgcc ccttaccctg agctgtgtgg cttt gggcag ctcgaactcc    3540 tgggttcctc tctgggcccc aactcctccc ctggcccaag tcccctcttt gctcctgggc    3600
aggcaggacc tctgtcccct ctcagccggt ccttggggct gcgtgtttct gtagtacgta    3660
gataagtagc atggcgggtt aatcattaac tacaaggaac ccctagtgat ggagttggcc    3720
actccctctc tgcgcgctcg ctcgctcact gaggccgggc gaccaaaggt cgcccgacgc    3780
ccgggctttg cccgggcggc ctcagtgagc gagcgagcgc gccagctggc gtaatagcga    3840
agaggcccgc accgatcgcc cttcccaaca gttgcgcagc ctgaatggcg aatggcgatt    3900
ccgttgcaat ggctggcggt aatattgttc tggatattac cagcaaggcc gatagtttga    3960
gttcttctac tcaggcaagt gatgttatta ctaatcaaag aagtattgcg acaacggtta    4020
atttgcgtga tggacagact ctttt actcg gtggcctcac tgattataaa aacacttctc    4080
aggattctgg cgtaccgttc ctgtctaaaa tccctttaat cggcctcctg tttagctccc    4140
gctctgattc taacgaggaa agcacgttat acgtgctcgt caaagcaacc atagtacgcg    4200
ccctgtagcg gcgcattaag cgcggcgggt gtggtggtta cgcgcagcgt gaccgctaca    4260
cttgccagcg ccctagcgcc cgctccttt c gctttcttcc cttcctttct cgccacgttc    4320
gccggctttc cccgtcaagc tctaaatcgg gggctcccct tagggttccg atttagtgct    4380
ttacggcacc tcgaccccaa aaaacttgat tagggtgatg gttcacgtag tgggccatcg    4440
ccctgataga cggttttt cg ccctttgacg ttggagtcca cgttctttaa tagtggactc    4500
ttgttccaaa ctggaacaac actcaaccct atctcggtct attctttt ga tttataaggg    4560 attttgccga tttcggccta ttggttaaaa aatgagctga tttaacaaaa atttaacgcg    4620
aattttaaca aaatattaac gtttacaatt taaatatttg cttatacaat cttcctgttt    4680
ttggggcttt tctgattatc aaccggggta catatgattg acatgctagt tttacgatta    4740
ccgttcatcg attctcttgt ttgctccaga ctctcaggca atgacctgat agcctttgta    4800
gagacctctc aaaaatagct acccctctccg gcatgaattt atcagctaga acggttgaat    4860
atcatattga tggtgatttg actgtctccg gcctttctca cccgtttgaa tctttaccta    4920
cacattactc aggcattgca tttaaaatat atgagggttc taaaaatttt tatccttgcg    4980
ttgaaataaa ggcttctccc gcaaaagtat acagggtca taatgttttt ggtacaaccg    5040
atttagcttt atgctctgag gctttattgc ttaattttgc taattctttg ccttgcctgt    5100
atgatttatt ggatgttgga atcgcctgat gcggtatttt ctccttacgc atctgtgcgg    5160
tatttcacac cgcatatggt gcactctcag tacaatctgc tctgatgccg catagttaag    5220
ccagccccga cacccgccaa cacccgctga cgcgccctga cgggcttgtc tgctcccggc    5280
atccgcttac agacaagctg tgaccgtctc cgggagctgc atgtgtcaga ggttttcacc    5340
gtcatcaccg aaacgcgcga gacgaaaggg cctcgtgata cgcctatttt tataggttaa    5400
tgtcatgata taatggttt cttagacgtc aggtggcact tttcggggaa atgtgcgcgg    5460
aacccctatt tgtttatttt tctaaataca ttcaaatatg tatccgctca tgagacaata    5520
```

```
acccCgataa atgcttcaat aatattgaaa aaggaagagt atgagtattc aacatttccg    5580
tgtcgccctt attcccttt ttgcggcatt ttgccttcct gttttttgctc acccagaaac    5640 gctggtgaaa gtaaaagatg ctgaagatca gttgggtgca cgagtgggtt acatcgaact    5700
ggatctcaac agcggtaaga tccttgagag ttttcgcccc gaagaacgtt ttccaatgat    5760
gagcactttt aaagttctgc tatgtggcgc ggtattatcc cgtattgacg ccgggcaaga    5820
gcaactcggt cgccgcatac actattctca gaatgacttg gttgagtact caccagtcac    5880
agaaaagcat cttacggatg gcatgacagt aagagaatta tgcagtgctg ccataaccat    5940
gagtgataac actgcggcca acttacttct gacaacgatc ggaggaccga aggagctaac    6000
cgcttttttg cacaacatgg ggatcatgt aactcgcctt gatcgttggg aaccggagct    6060
gaatgaagcc ataccaaacg acgagcgtga caccacgatg cctgtagcaa tggcaacaac    6120
gttgcgcaaa ctattaactg gcgaactact tactctagct tcccggcaac aattaataga    6180
ctggatggag gcggataaag ttgcaggacc acttctgcgc tcggcccttc cggctggctg    6240
gtttattgct gataaatctg gagccggtga gcgtgggtct cgcggtatca ttgcagcact    6300
ggggccagat ggtaagccct cccgtatcgt agttatctac acgacgggga gtcaggcaac    6360 tatgatgaa cgaaatagac agatcgctga gataggtgcc tcactgatta gcattggta    6420 actgtcagac caagtttact catatatact ttagattgat ttaaaacttc attttaatt    6480 taaaggatc taggtgaaga tcctttttga taatctcatg accaaaatcc cttaacgtga    6540
gttttcgttc cactgagcgt cagaccccgt agaaaagatc aaaggatctt cttgagatcc    6600 ttttttctg cgcgtaatct gctgcttgca acaaaaaaa ccaccgctac cagcggtggt    6660 ttgttgccg gatcaagagc taccaactct ttttccgaag gtaactggct tcagcagagc    6720
gcagatacca aatactgtcc ttctagtgta gccgtagtta ggccaccact tcaagaactc    6780
tgtagcaccg cctacatacc tcgctctgct aatcctgtta ccagtggctg ctgccagtgg    6840
cgataagtcg tgtcttaccg ggttggactc aagacgatag ttaccggata aggcgcagcg    6900
gtcgggctga acgggggggtt cgtgcacaca gcccagcttg gagcgaacga cctacaccga    6960
actgagatac ctacagcgtg agctatgaga aagcgccacg cttcccgaag ggagaaaggc    7020
ggacaggtat ccggtaagcg gcagggtcgg aacaggagag cgcacgaggg agcttccagg    7080
gggaaacgcc tggtatcttt atagtcctgt cgggtttcgc cacctctgac ttgagcgtcg    7140
atttttgtga tgctcgtcag ggggggcggag cctatggaaa aacgccagca acgcggcctt    7200
tttacggttc ctggcctttt gctggccttt tgctcacatg ttctttcctg cgttatcccc    7260
tgattctgtg gataaccgta ttaccgcctt tgagtgagct gataccgctc gccgcagccg    7320
aacgaccgag cgcagcgagt cagtgagcga ggaagcggaa gagcgcccaa tacgcaaacc    7380
gcctctcccc gcgcgttggc cgattcatta atg                                7413
```

<210> SEQ ID NO 3
<211> LENGTH: 3
<212> TYPE: PRT
<213> ORGANISM: Artificial Sequence
<220> FEATURE:
<223> OTHER INFORMATION: Exemplary linker sequence

<400> SEQUENCE: 3

Gly Gly Gly
1

<210> SEQ ID NO 4

```
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 4

Asp Gly Gly Gly Ser
1               5

<210> SEQ ID NO 5
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 5

Thr Gly Glu Lys Pro
1               5

<210> SEQ ID NO 6
<211> LENGTH: 4
<212> TYPE: PRT
<213> ORGANISM: Artificial Sequence
<220> FEATURE:
<223> OTHER INFORMATION: Exemplary linker sequence

<400> SEQUENCE: 6

Gly Gly Arg Arg
1

<210> SEQ ID NO 7
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 7

Gly Gly Gly Gly Ser
1               5

<210> SEQ ID NO 8
<211> LENGTH: 14
<212> TYPE: PRT
<213> ORGANISM: Artificial Sequence
<220> FEATURE:
<223> OTHER INFORMATION: Exemplary linker sequence

<400> SEQUENCE: 8

Glu Gly Lys Ser Ser Gly Ser Gly Ser Glu Ser Lys Val Asp
1               5                   10

<210> SEQ ID NO 9
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 9

Lys Glu Ser Gly Ser Val Ser Ser Glu Gln Leu Ala Gln Phe Arg Ser
1               5                   10                  15

Leu Asp
```

```
<210> SEQ ID NO 10
<211> LENGTH: 8
<212> TYPE: PRT
<213> ORGANISM: Artificial Sequence
<220> FEATURE:
<223> OTHER INFORMATION: Exemplary linker sequence

<400> SEQUENCE: 10

Gly Gly Arg Arg Gly Gly Gly Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Exemplary linker sequence

<400> SEQUENCE: 11

Leu Arg Gln Arg Asp Gly Glu Arg Pro
1               5

<210> SEQ ID NO 12
<211> LENGTH: 12
<212> TYPE: PRT
<213> ORGANISM: Artificial Sequence
<220> FEATURE:
<223> OTHER INFORMATION: Exemplary linker sequence

<400> SEQUENCE: 12

Leu Arg Gln Lys Asp Gly Gly Gly Ser Glu Arg Pro
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Exemplary linker sequence

<400> SEQUENCE: 13

Leu Arg Gln Lys Asp Gly Gly Gly Ser Gly Gly Gly Ser Glu Arg Pro
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: Cleavage sequence by TEV protease
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa = Gly or Ser

<400> SEQUENCE: 14

Glu Xaa Xaa Tyr Xaa Gln Xaa
1               5

<210> SEQ ID NO 15
<211> LENGTH: 7
```

<212> TYPE: PRT
<213> ORGANISM: Artificial Sequence
<220> FEATURE:
<223> OTHER INFORMATION: Cleavage sequence by TEV protease

<400> SEQUENCE: 15

Glu Asn Leu Tyr Phe Gln Gly
1               5

<210> SEQ ID NO 16
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 16

Glu Asn Leu Tyr Phe Gln Ser
1               5

<210> SEQ ID NO 17
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 17

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 18
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 18

Ala Thr Asn Phe Ser Leu Leu Lys Gln Ala Gly Asp Val Glu Glu Asn
1               5                   10                  15

Pro Gly Pro

<210> SEQ ID NO 19
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 19

Leu Leu Lys Gln Ala Gly Asp Val Glu Glu Asn Pro Gly Pro
1               5                   10

<210> SEQ ID NO 20
<211> LENGTH: 21
<212> TYPE: PRT
<213> ORGANISM: Artificial Sequence
<220> FEATURE:
<223> OTHER INFORMATION: Self-cleaving polypeptide comprising 2A site

<400> SEQUENCE: 20

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 21
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 21

Glu Gly Arg Gly Ser Leu Leu Thr Cys Gly Asp Val Glu Glu Asn Pro
1               5                   10                  15

Gly Pro

<210> SEQ ID NO 22
<211> LENGTH: 13
<212> TYPE: PRT
<213> ORGANISM: Artificial Sequence
<220> FEATURE:
<223> OTHER INFORMATION: Self-cleaving polypeptide comprising 2A site

<400> SEQUENCE: 22

Leu Leu Thr Cys Gly Asp Val Glu Glu Asn Pro Gly Pro
1               5                   10

<210> SEQ ID NO 23
<211> LENGTH: 23
<212> TYPE: PRT
<213> ORGANISM: Artificial Sequence
<220> FEATURE:
<223> OTHER INFORMATION: Self-cleaving polypeptide comprising 2A site

<400> SEQUENCE: 23

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 24
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 24

Gln Cys Thr Asn Tyr Ala Leu Leu Lys Leu Ala Gly Asp Val Glu Ser
1               5                   10                  15

Asn Pro Gly Pro
            20

<210> SEQ ID NO 25
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 25

Leu Leu Lys Leu Ala Gly Asp Val Glu Ser Asn Pro Gly Pro
1               5                   10

<210> SEQ ID NO 26

```
<211> LENGTH: 25
<212> TYPE: PRT
<213> ORGANISM: Artificial Sequence
<220> FEATURE:
<223> OTHER INFORMATION: Self-cleaving polypeptide comprising 2A site

<400> SEQUENCE: 26

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 27
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 27

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 28
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 28

Leu Leu Lys Leu Ala Gly Asp Val Glu Ser Asn Pro Gly Pro
1               5                   10

<210> SEQ ID NO 29
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 29

Leu Leu Asn Phe Asp Leu Leu Lys Leu Ala Gly Asp Val Glu Ser Asn
1               5                   10                  15

Pro Gly Pro

<210> SEQ ID NO 30
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 30

Thr Leu Asn Phe Asp Leu Leu Lys Leu Ala Gly Asp Val Glu Ser Asn
1               5                   10                  15

Pro Gly Pro

<210> SEQ ID NO 31
<211> LENGTH: 14
<212> TYPE: PRT
<213> ORGANISM: Artificial Sequence
<220> FEATURE:
```

```
<223> OTHER INFORMATION: Self-cleaving polypeptide comprising 2A site

<400> SEQUENCE: 31

Leu Leu Lys Leu Ala Gly Asp Val Glu Ser Asn Pro Gly Pro
1               5                   10

<210> SEQ ID NO 32
<211> LENGTH: 17
<212> TYPE: PRT
<213> ORGANISM: Artificial Sequence
<220> FEATURE:
<223> OTHER INFORMATION: Self-cleaving polypeptide comprising 2A site

<400> SEQUENCE: 32

Asn Phe Asp Leu Leu Lys Leu Ala Gly Asp Val Glu Ser Asn Pro Gly
1               5                   10                  15

Pro

<210> SEQ ID NO 33
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 33

Gln Leu Leu Asn Phe Asp Leu Leu Lys Leu Ala Gly Asp Val Glu Ser
1               5                   10                  15

Asn Pro Gly Pro
            20

<210> SEQ ID NO 34
<211> LENGTH: 24
<212> TYPE: PRT
<213> ORGANISM: Artificial Sequence
<220> FEATURE:
<223> OTHER INFORMATION: Self-cleaving polypeptide comprising 2A site

<400> SEQUENCE: 34

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 35
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 35

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr
        35                  40

<210> SEQ ID NO 36
<211> LENGTH: 18
<212> TYPE: PRT
<213> ORGANISM: Artificial Sequence
<220> FEATURE:
```

```
<223> OTHER INFORMATION: Self-cleaving polypeptide comprising 2A site

<400> SEQUENCE: 36

Leu Asn Phe Asp Leu Leu Lys Leu Ala Gly Asp Val Glu Ser Asn Pro
1               5                   10                  15

Gly Pro

<210> SEQ ID NO 37
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 37

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 38
<211> LENGTH: 33
<212> TYPE: PRT
<213> ORGANISM: Artificial Sequence
<220> FEATURE:
<223> OTHER INFORMATION: Self-cleaving polypeptide comprising 2A site

<400> SEQUENCE: 38

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 39
<211> LENGTH: 10
<212> TYPE: DNA
<213> ORGANISM: Artificial Sequence
<220> FEATURE:
<223> OTHER INFORMATION: Consensus Kozak sequence

<400> SEQUENCE: 39 gccrccatgg                                                          10

<210> SEQ ID NO 40
<211> LENGTH: 9
<212> TYPE: PRT
<213> ORGANISM: Artificial Sequence
<220> FEATURE:
<223> OTHER INFORMATION: Motif

<400> SEQUENCE: 40

Leu Ala Gly Leu Ile Asp Ala Asp Gly
1               5
```

DONOR REPAIR TEMPLATES MULTIPLEX GENOME EDITING

CROSS REFERENCE TO RELATED APPLICATIONS

This application is the National Stage of International Application No. PCT/US2018/018370, filed Feb. 15, 2018, which claims the benefit under 35 U.S.C. § 119(e) of U.S. Provisional Application No. 62/459,203, filed Feb. 15, 2017, each of which is incorporated by reference herein in its entirety.

REFERENCE TO SEQUENCE LISTING SUBMITTED ELECTRONICALLY

The Sequence Listing associated with this application is provided in text format in lieu of a paper copy, and is hereby incorporated by reference into the specification. The name of the text file containing the Sequence Listing is "BLUE084_Sequence_Listing". The text file is 30,266 bytes, was created on Jun. 3, 2022, and is submitted electronically via EFS-Web as an ASCII formatted sequence listing.

BACKGROUND

Technical Field

The present disclosure relates to improved donor repair template compositions for use in genome editing. More particularly, the disclosure relates to single donor repair templates designed to simultaneously target multiple sites in a genome.

Description of the Related Art

The ability to efficiently and simultaneously edit multiple genetic loci remains elusive. Moreover, the ability to drive homology directed repair at multiple target loci using DNA repair templates and genome editing nucleases such as zinc-finger nuclease (ZFN), TALE nuclease (TALENs), CRISPR/Cas9 nuclease systems, and megaTAL nucleases has proven to be particularly difficult.

Although adeno-associated virus (AAV) DNA repair templates are often selected for editing a single genomic loci because they have low immunogenicity and are efficient at driving homology-directed recombination, existing designs are not suitable for simultaneously targeting multiple genetic loci. The prevailing solution to the problem of targeting multiple genetic loci remains using multiple nucleases and multiple DNA donor repair templates. The solution is ineffective and not suitable for manufacturing complex genome editing cell-based therapies for clinical use.

BRIEF SUMMARY

Improved immune effector cell compositions and methods of manufacturing the same using multiplex genome editing compositions are contemplated herein.

In various embodiments, a DNA donor repair template is provided comprising: a first pair of homology arms to a first target site; a second pair of homology arms to a second target site; and one or more transgenes.

In particular embodiments, the first pair of homology arms comprises a 5' homology arm homologous to a DNA sequence 5' of the first target site; and a 3' homology arm homologous to a DNA sequence 3' of the first target site.

In particular embodiments, the second pair of homology arms comprises a 5' homology arm homologous to a DNA sequence 5' of the second target site; and a 3' homology arm homologous to a DNA sequence 3' of the second target site.

In certain embodiments, the lengths of the 5' and 3' homology arms to the first target site and/or the second target site are independently selected from about 100 bp to about 2500 bp.

In some embodiments, the lengths of the 5' and 3' homology arms to the first target site and/or the second target site are independently selected from about 100 bp to about 1500 bp.

In additional embodiments, the lengths of the 5' and 3' homology arms to the first target site and/or the second target site are independently selected from about 100 bp to about 1000 bp.

In particular embodiments, the lengths of the 5' and 3' homology arms to the first target site and/or the second target site are independently selected from about 100 bp to about 500 bp.

In further embodiments, the lengths of the 5' and 3' homology arms to the first target site and/or the second target site are about 500 bp.

In some embodiments, the lengths of the 5' and 3' homology arms to the first target site and/or the second target site are about 300 bp.

In additional embodiments, the lengths of the 5' and 3' homology arms to the first target site and/or the second target site are about 100 bp.

In particular embodiments, the 5' homology arm of the first target site is located 5' of the 5' homology arm of the second target site.

In certain embodiments, the 3' homology arm of the first target site is located 5' of the 3' homology arm of the second target site.

In some embodiments, the 3' homology arm of the first target site is located 3' of the 3' homology arm of the second target site.

In further embodiments, the 5' homology arm and the 3' homology arm of the first target site flank a first transgene and the 5' homology arm and the 3' homology arm of the second target site flank a second transgene.

In further embodiments, the first target site and the second target site are in different genes.

In particular embodiments, the first target site or the second target site comprises an engineered nuclease cleavage site in a TCRα gene.

In some embodiments, the first target site or the second target site comprises an engineered nuclease cleavage site in an immune system checkpoint gene or a gene that encodes an immunosuppressive signaling component.

In particular embodiments, the first target site is an engineered nuclease cleavage site in a TCRα gene and the second target site is an engineered nuclease cleavage site in an immune system checkpoint gene or a gene that encodes an immunosuppressive signaling component.

In certain embodiments, the first target site is an engineered nuclease cleavage site in a first immune system checkpoint gene or a gene that encodes an immunosuppressive signaling component and the second target site is an engineered nuclease cleavage site in a second immune system checkpoint gene or a gene that encodes an immunosuppressive signaling component.

In further embodiments, the immune system checkpoint gene is independently selected from the group consisting of:

programmed cell death protein 1 (PD-1), lymphocyte activation gene 3 protein (LAG-3), T cell immunoglobulin domain and mucin domain protein 3 (TIM-3), cytotoxic T lymphocyte antigen-4 (CTLA-4), band T lymphocyte attenuator (BTLA), T cell immunoglobulin and immunoreceptor tyrosine-based inhibitory motif domain (TIGIT), V-domain Ig suppressor of T cell activation (VISTA), and killer cell immunoglobulin-like receptor (KIR) genes.

In certain embodiments, the gene that encodes an immunosuppressive signaling component is independently selected from the group consisting of: interleukin receptor 10 alpha, transforming growth factor β receptor I (TGFβRI), transforming growth factor β receptor II (TGFβRII), aryl hydrocarbon receptor (AHR), serum and glucocorticoid-regulated kinase 1 (SGK1), tuberous sclerosis complex 2 (TSC2), von Hippel-Lindau tumor suppressor (VHL), adenosine A2a receptor (A2AR), and Cbl proto-oncogene B (CBLB).

In particular embodiments, the engineered nuclease is selected from the group consisting of: a meganuclease, a megaTAL, a TALEN, a ZFN, and a CRISPR/Cas nuclease.

In further embodiments, the engineered nuclease is a meganuclease engineered from an LAGLIDADG (SEQ ID NO: 40) homing endonuclease (LHE) selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMIII, I-PanMIII, I-PnoMI, I-ScuMI, I-SmaMI, I-SscMI, and I-Vdi141I.

In some embodiments, the engineered nuclease is a meganuclease engineered from an LHE selected from the group consisting of: I-CpaMI, I-HjeMI, I-OnuI, I-PanMI, and SmaMI.

In particular embodiments, the engineered nuclease is an I-OnuI LHE.

In additional embodiments, the engineered nuclease is an I-SmaMI LHE.

In certain embodiments, the engineered nuclease is a megaTAL comprising a TALE DNA binding domain and an engineered meganuclease.

In further embodiments, the TALE binding domain comprises about 9.5 TALE repeat units to about 15.5 TALE repeat units.

In particular embodiments, the TALE binding domain comprises about 9.5 TALE repeat units, about 10.5 TALE repeat units, about 11.5 TALE repeat units, about 12.5 TALE repeat units, about 13.5 TALE repeat units, about 14.5 TALE repeat units, or about 15.5 TALE repeat units.

In additional embodiments, the one or more transgenes comprises a polynucleotide encoding an immunopotency enhancer, an immunosuppressive signal damper, or an engineered antigen receptor.

In certain embodiments, the one or more transgenes further comprise an RNA polymerase II promoter operably linked to the polynucleotide encoding the immunopotency enhancer, the immunosuppressive signal damper, or the engineered antigen receptor.

In some embodiments, the one or more transgenes encodes one or more CARs.

In particular embodiments, the one or more CARs are selected from the group consisting of an anti-BCMA CAR and an anti-CD19 CAR.

In further embodiments, the RNA polymerase II promoter is selected from the group consisting of: a short EF1α promoter, a long EF1α promoter, a human ROSA 26 locus, a Ubiquitin C (UBC) promoter, a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter.

In further embodiments, the polynucleotide further encodes one or more self-cleaving viral peptides operably linked to, interspersed between, and/or flanking one or more immunopotency enhancers, immunosuppressive signal dampers, or engineered antigen receptors.

In additional embodiments, the self-cleaving viral peptide is a 2A peptide.

In particular embodiments, the polynucleotide further comprises a heterologous polyadenylation signal.

In certain embodiments, the one or more immunosuppressive signal dampers comprise an enzymatic function that counteracts an immunosuppressive factor; an exodomain that binds an immunosuppressive factor, optionally wherein the exodomain is an antibody or antigen binding fragment thereof; an exodomain that binds an immunosuppressive factor and a transmembrane domain; or an exodomain that binds an immunosuppressive factor, a transmembrane domain, and a modified endodomain that is unable to transduce immunosuppressive signals.

In particular embodiments, the one or more immunopotency enhancers are independently selected from the group consisting of: a bispecific T cell engager molecule (BiTE), an immunopotentiating factor, and a flip receptor.

In some embodiments, the one or more immunopotency enhancers are independently selected from the group consisting of: a cytokine, a chemokine, a cytotoxin, a cytokine receptor, and variants thereof.

In particular embodiments, the one or more engineered antigen receptors are independently selected from the group consisting of: an engineered TCR, a CAR, a DARIC, or a zetakine.

In additional embodiments, the one or more engineered antigen receptors are CARs.

In particular embodiments, the one or more CARs are selected from the group consisting of an anti-BCMA CAR and an anti-CD19 CAR.

In various embodiments, a viral vector comprising a DNA donor repair template contemplated herein is provided.

In further embodiments, the viral vector is a recombinant adeno-associated viral vector (rAAV) or a retrovirus.

In certain embodiments, the rAAV has one or more ITRs from AAV2.

In particular embodiments, the rAAV has a serotype selected from the group consisting of: AAV1, AAV2, AAV3, AAV4, AAV5, AAV6, AAV7, AAV8, AAV9, and AAV10.

In some embodiments, the rAAV has an AAV6 serotype.

In some embodiments, the retrovirus is a lentivirus.

In additional embodiments, the lentivirus is an integrase deficient lentivirus.

In various embodiments, a cell comprising a DNA donor repair template and/or a viral vector contemplated herein is provided.

In certain embodiments, the one or more transgenes have been inserted at the first target site and at the second target site by homology directed repair.

In some embodiments, the cell is a hematopoietic cell.

In particular embodiments, the cell is an immune effector cell.

In certain embodiments, the cell is CD3+, CD4+, CD8+, or a combination thereof.

In additional embodiments, the cell is a T cell.

In further embodiments, the cell is a cytotoxic T lymphocyte (CTL), a tumor infiltrating lymphocyte (TIL), or a helper T cell.

In particular embodiments, the source of the cell is peripheral blood mononuclear cells, bone marrow, lymph nodes tissue, cord blood, thymus issue, tissue from a site of infection, ascites, pleural effusion, spleen tissue, or tumors.

In various embodiments, a composition comprising a DNA donor repair template, a viral vector, or a cell contemplated herein is provided.

In various embodiments, a composition comprising a physiologically acceptable excipient and a DNA donor repair template, a viral vector, or a cell contemplated herein is provided.

In various embodiments, a method of treating, preventing, or ameliorating at least one symptom of a cancer, infectious disease, autoimmune disease, inflammatory disease, and immunodeficiency, or condition associated therewith is provided, comprising administering to the subject an effective amount of a composition contemplated herein, and optionally administering to the subject an effective amount of one or more polynucleotides encoding one or more engineered nucleases designed to introduce a DSB at the first target site and a DSB at the second target site.

In various embodiments, a method of treating a solid cancer is provided comprising administering to the subject an effective amount of a composition contemplated herein, and optionally administering to the subject an effective amount of one or more polynucleotides encoding one or more engineered nucleases designed to introduce a DSB at the first target site and the second target site.

In some embodiments, the solid cancer comprises liver cancer, pancreatic cancer, lung cancer, breast cancer, ovarian cancer, prostate cancer, testicular cancer, bladder cancer, brain cancer, sarcoma, head and neck cancer, bone cancer, thyroid cancer, kidney cancer, or skin cancer.

In various embodiments, a method of treating a hematological malignancy is provided comprising administering to the subject an effective amount of a composition contemplated herein, and optionally administering to the subject an effective amount of one or more polynucleotides encoding one or more engineered nucleases designed to introduce a DSB at the first target site and the second target site.

In particular embodiments, the hematological malignancy is a leukemia, lymphoma, or multiple myeloma.

BRIEF DESCRIPTION OF THE SEQUENCE IDENTIFIERS

Figure 1:
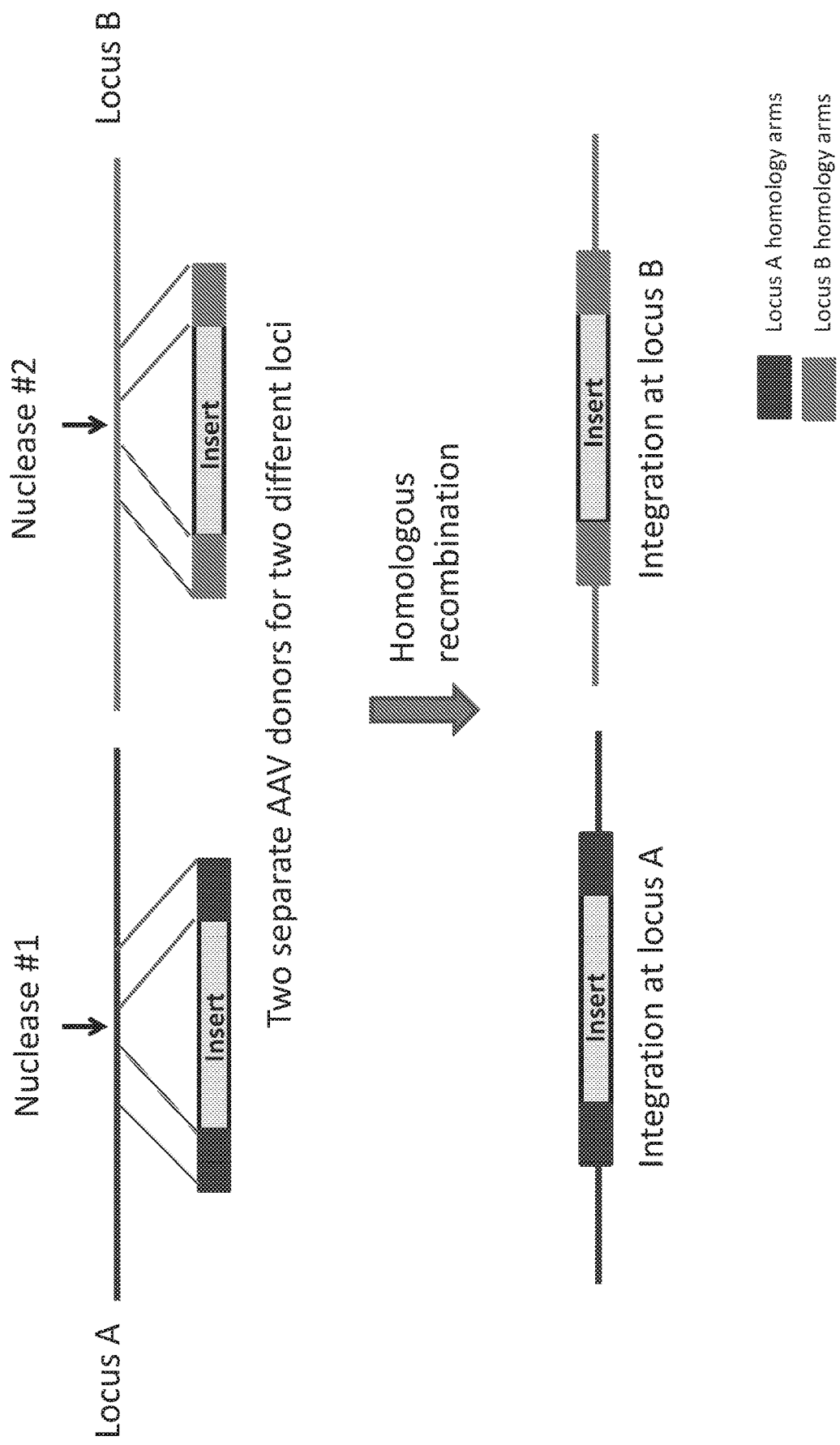
FIG. 1 shows a common and ineffective strategy for driving homology directed repair at multiple target loci using multiple AAV donor repair templates.
Figure 2:
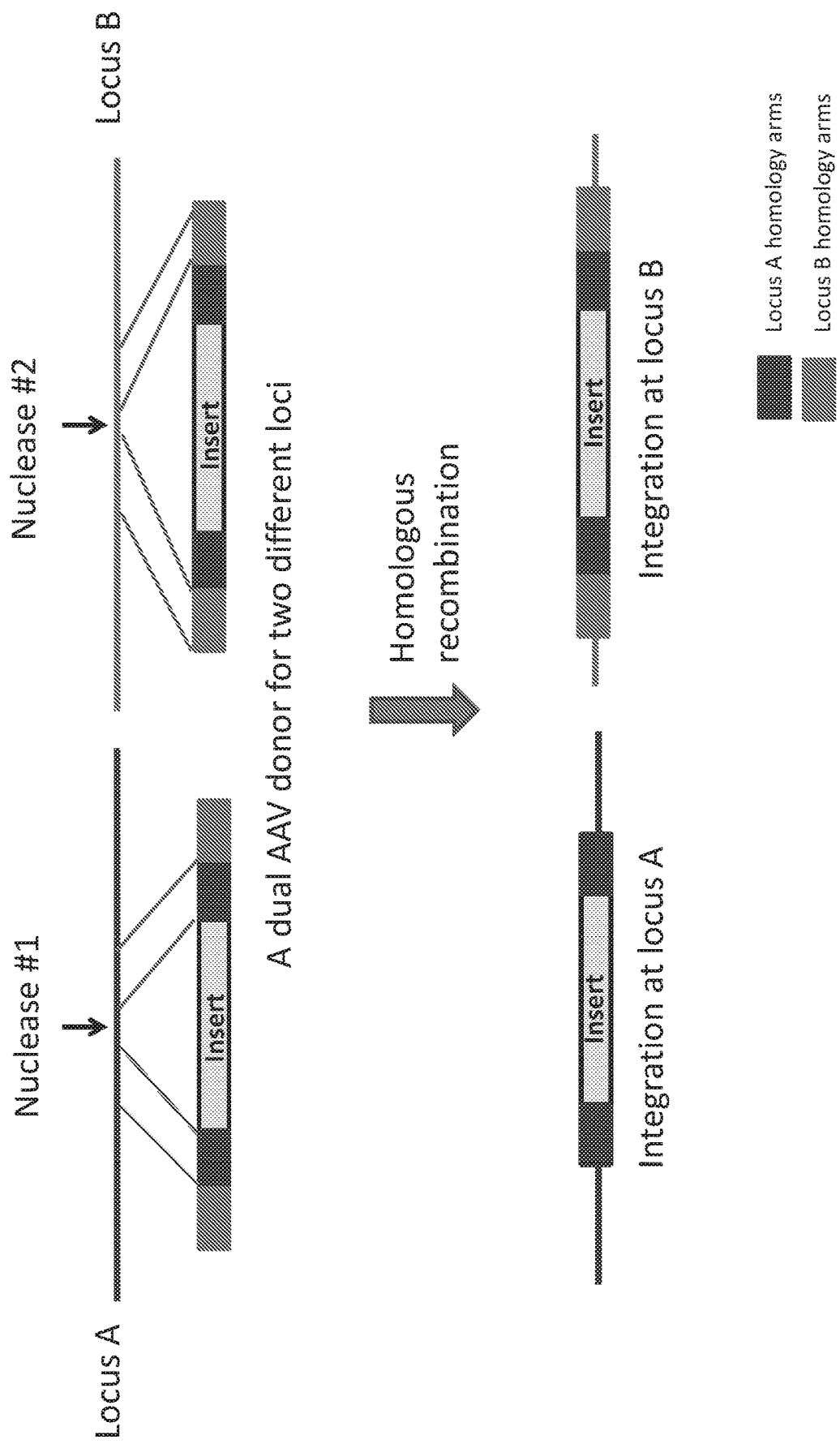
FIG. 2 shows a representative inventive strategy for efficiently driving homology directed repair at multiple target loci using a single AAV donor repair template.

SEQ ID NO: 1 sets forth the polynucleotide sequence of an AAV donor repair template.

SEQ ID NO: 2 sets forth the polynucleotide sequence of an AAV donor repair template.

SEQ ID NOs: 3-13 set forth the amino acid sequences of various linkers.

SEQ ID NOs: 14-38 set forth the amino acid sequences of protease cleavage sites and self-cleaving polypeptide cleavage sites.

DETAILED DESCRIPTION

A. Overview

Various embodiments contemplated herein, generally relate to, in part, improved genome editing compositions and methods of manufacturing improved immune effector cell compositions using the same. The improved genome editing compositions and methods enable the editing of multiple target sites in the genome using a single DNA donor repair template, thereby greatly simplifying and increasing the efficiency of multiplex genome editing in a population of therapeutics cells. Therapeutic cells with multiple genome edits are contemplated for use in the treatment or prevention of numerous conditions including, but not limited to hemoglobinopathies, cancer, infectious disease, autoimmune disease, inflammatory disease, and immunodeficiency.

In various embodiments, a DNA donor repair template that enables genome editing of one or more target sites is provided.

In various embodiments, a vector comprising a DNA donor repair template that enables genome editing of one or more target sites is provided.

In various embodiments, a cell comprising one or more engineered nucleases and a DNA donor repair template that enables genome editing of one or more target sites is provided. In particular embodiments, the cell is a hematopoietic cell, including, without limitation, hematopoietic stem cells, hematopoietic progenitor cells, CD34+ cells, immune effector cells, and T cells.

In particular embodiments, target sites suitable for multiplex genome editing contemplated herein include, but are not limited to one or more loci that contribute to repression of γ-globin gene expression, hemoglobinopathies, thalassemias, and sickle cell disease.

Genome edited hematopoietic stem cells, hematopoietic progenitor cells, or CD34+ cells with multiple genome edits, may comprise one or more edits in a gene that contributes to repression of γ-globin gene expression and HbF, including, but not limited to the BCL11A locus, the KLF1 locus, the SOX6 locus, the GATA1 locus, and the LSD1 locus; a thalassemic allele of a β-globin locus, or a sickling allele of a β-globin locus. Without wishing to be bound to any particular theory, it is contemplated that engineered nucleases designed to precisely disrupt or modify globin gene expression through genome editing can enhance production of therapeutic hemoglobin expression and treat, prevent, or ameliorate at least one symptom of a hemoglobinopathy.

In particular embodiments, target sites suitable for multiplex genome editing contemplated herein include, but are not limited to one or more loci that contribute to T cell receptor (TCR) signaling, immune system checkpoint genes, and genes encoding immunosuppressive signaling components.

Genome edited T cells with multiple genome edits, may comprise one or more edits in a gene that contributes to TCR signaling, including, but not limited to the TCR alpha (TCRα) locus and TCR beta (TCRβ) locus.

Genome edited T cells with multiple genome edits, may comprise or may further comprise one or more edits in a gene that encodes an immune system checkpoint gene or a gene encoding an immunosuppressive signaling component. T cells comprising edits that reduce the function of immune system checkpoint genes and immunosuppressive signaling components are more resistant to T cell exhaustion and have increased T cell durability and persistence in the tumor microenvironment.

Illustrative examples of immune system checkpoint genes include, but are not limited to: programmed cell death protein 1 (PD-1), lymphocyte activation gene 3 protein (LAG-3), T cell immunoglobulin domain and mucin domain protein 3 (TIM-3), cytotoxic T lymphocyte antigen-4 (CTLA-4), band T lymphocyte attenuator (BTLA), T cell immunoglobulin and immunoreceptor tyrosine-based inhibitory motif domain (TIGIT), V-domain Ig suppressor of T cell activation (VISTA), and killer cell immunoglobulin-like receptor (KIR) genes.

Illustrative examples of genes encoding immunosuppressive signaling components include, but are not limited to: interleukin 10 receptor alpha (IL-10Rα), transforming growth factor beta receptor 1 (TGFβR1), transforming growth factor beta receptor 2 (TGFβR2), ayrl hydrocarbon receptor (AHR), serum/glucocorticoid regulated kinase 1 (SGK1), tuberous sclerosis complex 2 (TSC2), adenosine A2A receptor (A2AR), von Hippel-Lindau tumor suppressor (VHL), and Cbl proto-oncogene B (CBLB).

Without wishing to be bound by any particular theory, it is contemplated that T cells comprising one or more genome edits that disrupt the function of one or more TCR signaling components will provide safer and more efficacious adoptive cell therapies because they substantially lack functional endogenous TCR expression, thereby reducing potential graft rejection and because they free up accessory singaling components to enhance the efficacy of engineered antigen receptor T cells. In addition, T cells comprising one or more genome edits in immune system checkpoint genes or immunosuppressive signaling components will provide adoptive cell therapies with reduced susceptibility to T cell exhaustion, increased T cell durability, and increased T cell persistence in the tumor microenvironment.

In various embodiments, a cell comprises a plurality of engineered nucleases that induce DSBs at multiple target sites and a DNA donor repair template that encodes one or more transgenes that are inserted into the multiple target sites through homology directed repair (HDR).

Illustrative examples of transgenes suitable for use in the DNA donor repair templates contemplated in particular embodiments include, but are not limited to: globin genes and anti-sickling globin genes.

Illustrative examples of transgenes suitable for use in the DNA donor repair templates contemplated in particular embodiments include, but are not limited to: an immunopotency enhancer, an immunosuppressive signal damper, or an engineered antigen receptor. Without wishing to be bound by any particular theory, it is contemplated that disrupting multiple target sites encoding genes that contribute to TCR signaling, immune system checkpoints, and/or immunosuppressive signaling, and introducing one or more transgenes encoding an immunopotency enhancer, an immunosuppressive signal damper, or an engineered antigen receptor into the loci, imbues the resulting adoptive cell therapies with superior safety, efficacy, durability, and/or persistence profiles compared to adoptive cell therapies comprising only gene disruptive edits or only expression of an immunopotency enhancer, an immunosuppressive signal damper, or an engineered antigen receptor.

In various embodiments, a method of editing the genome of a cell at multiple target sites by introducing one or more polynucleotides encoding one or more engineered nucleases and a DNA donor template that enables genome editing of one or more target sites is provided.

In various embodiments, a method of treating, preventing, or ameliorating at least one symptom of a hemoglobinopathy, cancer, infectious disease, autoimmune disease, inflammatory disease, and immunodeficiency, or condition associated therewith with a genome edited cell therapy contemplated herein is provided.

The practice of the particular embodiments will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); Transcription and Translation (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as *Advances in Immunology*.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, 3%, ±2%, or ±1% about a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," "a various embodiment," or "a further embodiment" or plurals or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

An "isolated cell" refers to a non-naturally occurring cell, e.g., a cell that does not exist in nature, a modified cell, an engineered cell, etc., that has been obtained from an in vivo tissue or organ and is substantially free of extracellular matrix. In one embodiment, an isolated cell comprises one or more polynucleotide sequences that are not naturally occurring in the cell.

The term "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are subclassified according to their developmental potential as totipotent, pluripotent, multipotent and oligo/unipotent. "Self-renewal" refers a cell with a unique capacity to produce unaltered daughter cells and to generate specialized cell types (potency). Self-renewal can be achieved in two ways. Asymmetric cell division produces one daughter cell that is identical to the parental cell and one daughter cell that is different from the parental cell and is a progenitor or differentiated cell. Symmetric cell division produces two identical daughter cells.

As used herein, the term "progenitor" or "progenitor cells" refers to cells have the capacity to self-renew and to differentiate into more mature cells. Many progenitor cells differentiate along a single lineage, but may have quite extensive proliferative capacity.

The term "primary cell" as used herein is known in the art to refer to a cell that has been isolated from a tissue and has been established for growth in vitro or ex vivo. Corresponding cells have undergone very few, if any, population doublings and are therefore more representative of the main functional component of the tissue from which they are derived in comparison to continuous cell lines, thus representing a more representative model to the in vivo state. Methods to obtain samples from various tissues and methods to establish primary cell lines are well-known in the art (see, e.g., Jones and Wise, Methods Mol Biol. 1997). In particular embodiments, the cell is a primary cell. Primary cells for use in the methods contemplated herein are derived from umbilical cord blood, placental blood, mobilized peripheral blood and bone marrow.

As used herein, the term "population of cells" refers to a plurality of cells that may be made up of any number and/or combination of homogenous or heterogeneous cell types, as described elsewhere herein. A population of cells may comprise about 10%, about 20%, about 30%, about 40%, about 50%, about 60%, about 70%, about 80%, about 90%, or about 100% of the target cell type to be edited.

The term "hematopoietic stem cell" or "HSC" refers to multipotent stem cells that give rise to the all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827). When transplanted into lethally irradiated animals or humans, hematopoietic stem and progenitor cells can repopulate the erythroid, neutrophil-macrophage, megakaryocyte and lymphoid hematopoietic cell pool.

The term "CD34$^+$ cell," as used herein refers to a cell expressing the CD34 protein on its cell surface. "CD34," as used herein refers to a cell surface glycoprotein (e.g., sialomucin protein) that often acts as a cell-cell adhesion factor. CD34$^+$ is a cell surface marker of both hematopoietic stem and progenitor cells. CD34$^+$ is a cell surface marker of both hematopoietic stem and progenitor cells. Hematopoietic cells suitable for use in particular embodiments contemplated herein include, but are not limited to: CD34$^+$ cells. Hematopoietic cells suitable for use in particular embodiments contemplated herein include, but are not limited to: CD34$^+$CD38$^{Lo}$CD90$^+$CD45RA$^-$ cells, CD34$^+$, CD59$^+$, Thy1/CD90$^+$, CD38$^{Lo/-}$, C-kit/CD117$^+$, and Lin$^{(-)}$ cells, and CD34$^+$, CD133$^+$ cells.

An "immune effector cell," is any cell of the immune system that has one or more effector functions (e.g., cytotoxic cell killing activity, secretion of cytokines, induction of ADCC and/or CDC). Illustrative immune effector cells contemplated in particular embodiments are T lymphocytes, in particular cytotoxic T cells (CTLs; CD8$^+$ T cells), TILs, and helper T cells (HTLs; CD4$^+$ T cells). In one embodiment, immune effector cells include natural killer (NK) cells. In one embodiment, immune effector cells include natural killer T (NKT) cells.

The terms "T cell" or "T lymphocyte" are art-recognized and are intended to include thymocytes, naïve T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4$^+$ T cell) CD4$^+$ T cell, a cytotoxic T cell (CTL; CD8$^+$ T cell), a tumor infiltrating cytotoxic T cell (TIL; CD8$^+$ T cell), CD4$^+$CD8$^+$ T cell, CD4$^-$CD8$^-$ T cell, or any other subset of T cells. In one embodiment, the T cell is an NKT cell. Other illustrative populations of T cells suitable for use in particular embodiments include naïve T cells and memory T cells.

"Potent T cells," and "young T cells," are used interchangeably in particular embodiments and refer to T cell phenotypes wherein the T cell is capable of proliferation and a concomitant decrease in differentiation. In particular embodiments, the young T cell has the phenotype of a "naïve T cell." In particular embodiments, young T cells comprise one or more of, or all of the following biological markers: CD62L, CCR7, CD28, CD27, CD122, CD127, CD197, and CD38. In one embodiment, young T cells comprise one or more of, or all of the following biological markers: CD62L, CD127, CD197, and CD38. In one embodiment, the young T cells lack expression of CD57, CD244, CD160, PD-1, CTLA4, TIM3, and LAG3.

As used herein, the term "proliferation" refers to an increase in cell division, either symmetric or asymmetric division of cells. In particular embodiments, "proliferation" refers to the symmetric or asymmetric division of hematopoietic cells. "Increased proliferation" occurs when there is an increase in the number of cells in a treated sample compared to cells in a non-treated sample.

As used herein, the term "differentiation" refers to a method of decreasing the potency or proliferation of a cell or moving the cell to a more developmentally restricted state. In particular embodiments, differentiated T cells acquire immune effector cell functions.

As used herein, the terms "T cell manufacturing" or "methods of manufacturing T cells' or comparable terms refer to the process of producing a therapeutic composition of T cells, which manufacturing methods may comprise one or more of, or all of the following steps: harvesting, stimulation, activation, genome editing, and expansion.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured or modulated in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism, such as cell self-renewal and cell proliferation or expansion. In one embodiment, the term "in vivo expansion" refers to the ability of a cell population to increase in number in vivo. In one embodiment, cells are engineered or modified in vivo.

The term "stimulation" refers to a primary response induced by binding of a stimulatory molecule (e.g., a TCR/CD3 complex) with its cognate ligand thereby mediating a signal transduction event including, but not limited to, signal transduction via the TCR/CD3 complex.

A "stimulatory molecule," refers to a molecule on a T cell that specifically binds with a cognate stimulatory ligand.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands include, but are not limited to CD3 ligands, e.g., an anti-CD3 antibody and CD2 ligands, e.g., anti-CD2 antibody, and peptides, e.g., CMV, HPV, EBV peptides.

The term, "activation" refers to the state of a T cell that has been sufficiently stimulated to induce detectable cellular proliferation. In particular embodiments, activation can also be associated with induced cytokine production, and detectable effector functions. The term "activated T cells" refers to, among other things, T cells that are proliferating. Signals generated through the TCR alone are insufficient for full activation of the T cell and one or more secondary or costimulatory signals are also required. Thus, T cell activation comprises a primary stimulation signal through the TCR/CD3 complex and one or more secondary costimulatory signals. Co-stimulation can be evidenced by proliferation and/or cytokine production by T cells that have received a primary activation signal, such as stimulation through the CD3/TCR complex or through CD2.

A "costimulatory signal," refers to a signal, which in combination with a primary signal, such as TCR/CD3 ligation, leads to T cell proliferation, cytokine production, and/or upregulation or downregulation of particular molecules (e.g., CD28).

A "costimulatory ligand," refers to a molecule that binds a costimulatory molecule. A costimulatory ligand may be soluble or provided on a surface. A "costimulatory molecule" refers to the cognate binding partner on a T cell that specifically binds with a costimulatory ligand (e.g., anti-CD28 antibody).

An "antigen (Ag)" refers to a compound, composition, or substance, e.g., lipid, carbohydrate, polysaccharide, glycoprotein, peptide, or nucleic acid, that can stimulate the production of antibodies or a T cell response in an animal, including compositions (such as one that includes a tumor-specific protein) that are injected or absorbed into an animal. An antigen reacts with the products of specific humoral or cellular immunity, including those induced by heterologous antigens, such as the disclosed antigens. A "target antigen" or "target antigen of interest" is an antigen that a binding domain of an engineered antigen receptor contemplated herein, is designed to bind. In one embodiment, the antigen is an MHC-peptide complex, such as a class I MHC-peptide complex or a class II MHC-peptide complex.

An "epitope" or "antigenic determinant" refers to the region of an antigen to which a binding agent binds.

As used herein, "isolated polynucleotide" refers to a polynucleotide that has been purified from the sequences which flank it in a naturally-occurring state, e.g., a DNA fragment that has been removed from the sequences that are normally adjacent to the fragment. An "isolated polynucleotide" also refers to a complementary DNA (cDNA), a recombinant DNA, or other polynucleotide that does not exist in nature and that has been made by the hand of man.

An "isolated protein," "isolated peptide," or "isolated polypeptide" and the like, as used herein, refer to in vitro synthesis, isolation, and/or purification of a peptide or polypeptide molecule from a cellular environment, and from association with other components of the cell, i.e., it is not significantly associated with in vivo substances.

By "enhance" or "promote" or "increase" or "expand" or "potentiate" refers generally to the ability of a composition contemplated herein to produce, elicit, or cause a greater response (i.e., physiological response) compared to the response caused by either vehicle or control. A measurable response may include an increase in catalytic activity, binding affinity, binding site specificity, binding site selectivity, persistence, cytolytic activity, and/or an increase in proinflammatory cytokines, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response produced by vehicle or control.

By "decrease" or "lower" or "lessen" or "reduce" or "abate" or "ablate" or "inhibit" or "dampen" refers generally to the ability of a composition contemplated herein to produce, elicit, or cause a lesser response (i.e., physiological response) compared to the response caused by either vehicle or control. A measurable response may include a decrease in off-target binding affinity, off-target cleavage specificity, T cell exhaustion, and the like. A "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response (reference response) produced by vehicle, or control.

By "maintain," or "preserve," or "maintenance," or "no change," or "no substantial change," or "no substantial decrease" refers generally to the ability of a composition contemplated herein to produce, elicit, or cause a substantially similar or comparable physiological response (i.e., downstream effects) in as compared to the response caused by either vehicle or control. A comparable response is one that is not significantly different or measurable different from the reference response.

The terms "specific binding affinity" or "specifically binds" or "specifically bound" or "specific binding" or "specifically targets" as used herein, describe binding of one molecule to another, e.g., DNA binding domain of a polypeptide binding to DNA, at greater binding affinity than background binding. A binding domain "specifically binds" to a target site if it binds to or associates with a target site with an affinity or $K_a$ (i.e., an equilibrium association constant of a particular binding interaction with units of 1/M) of, for example, greater than or equal to about $10^5$ $M^{-1}$. In certain embodiments, a binding domain binds to a target site with a $K_a$ greater than or equal to about $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}$ $M^{-1}$. "High affinity" binding domains refers to those binding domains with a $K_a$ of at least $10^7$ $M^{-1}$, at least $10^7$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater.

Alternatively, affinity may be defined as an equilibrium dissociation constant ($K_d$) of a particular binding interaction with units of M (e.g., $10^{-5}$ M to $10^{-13}$ M, or less). Affinities of nuclease variants comprising one or more DNA binding domains for DNA target sites contemplated in particular embodiments can be readily determined using conventional techniques, e.g., yeast cell surface display, or by binding association, or displacement assays using labeled ligands.

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

The terms "selectively binds" or "selectively bound" or "selectively binding" or "selectively targets" and describe preferential binding of one molecule to a target molecule (on-target binding) in the presence of a plurality of off-target molecules. In particular embodiments, an HE or megaTAL selectively binds an on-target DNA binding site about 5, 10, 15, 20, 25, 50, 100, or 1000 times more frequently than the HE or megaTAL binds an off-target DNA target binding site.

"On-target" refers to a target site sequence.

"Off-target" refers to a sequence similar to but not identical to a target site sequence.

A "target site" or "target sequence" is a chromosomal or extrachromosomal nucleic acid sequence that defines a portion of a nucleic acid to which a binding molecule will bind and/or cleave, provided sufficient conditions for binding and/or cleavage exist. When referring to a polynucleotide sequence or SEQ ID NO. that references only one strand of a target site or target sequence, it would be understood that the target site or target sequence bound and/or cleaved by a nuclease variant is double-stranded and comprises the reference sequence and its complement.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair (HDR) mechanisms. This process requires nucleotide sequence homology, uses a "donor" molecule as a template to repair a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"NHEJ" or "non-homologous end joining" refers to the resolution of a double-strand break in the absence of a donor repair template or homologous sequence. NHEJ can result in insertions and deletions at the site of the break. NHEJ is mediated by several sub-pathways, each of which has distinct mutational consequences. The classical NHEJ pathway (cNHEJ) requires the KU/DNA-PKcs/Lig4/XRCC4 complex, ligates ends back together with minimal processing and often leads to precise repair of the break. Alternative NHEJ pathways (altNHEJ) also are active in resolving dsDNA breaks, but these pathways are considerably more mutagenic and often result in imprecise repair of the break marked by insertions and deletions. While not wishing to be bound to any particular theory, it is contemplated that modification of dsDNA breaks by end-processing enzymes, such as, for example, exonucleases, e.g., Trex2, may bias repair towards an altNHEJ pathway.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, polypeptides and nuclease variants, e.g., homing endonuclease variants, megaTALs, etc. contemplated herein are used for targeted double-stranded DNA cleavage. Endonuclease cleavage recognition sites may be on either DNA strand.

An "exogenous" molecule is a molecule that is not normally present in a cell, but that is introduced into a cell by one or more genetic, biochemical or other methods. Exemplary exogenous molecules include, but are not limited to small organic molecules, protein, nucleic acid, carbohydrate, lipid, glycoprotein, lipoprotein, polysaccharide, any modified derivative of the above molecules, or any complex comprising one or more of the above molecules. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, biopolymer nanoparticle, calcium phosphate co-precipitation, DEAE-dextran-mediated transfer and viral vector-mediated transfer.

An "endogenous" molecule is one that is normally present in a particular cell at a particular developmental stage under particular environmental conditions. Additional endogenous molecules can include proteins.

A "gene," refers to a DNA region encoding a gene product, as well as all DNA regions which regulate the production of the gene product, whether or not such regulatory sequences are adjacent to coding and/or transcribed sequences. A gene includes, but is not limited to, promoter sequences, enhancers, silencers, insulators, boundary elements, terminators, polyadenylation sequences, post-transcription response elements, translational regulatory sequences such as ribosome binding sites and internal ribosome entry sites, replication origins, matrix attachment sites, and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

As used herein, the term "genetically engineered" or "genetically modified" refers to the chromosomal or extra-chromosomal addition of extra genetic material in the form of DNA or RNA to the total genetic material in a cell. Genetic modifications may be targeted or non-targeted to a particular site in a cell's genome. In one embodiment, genetic modification is site specific. In one embodiment, genetic modification is not site specific.

As used herein, the term "genome editing" refers to the substitution, deletion, and/or introduction of genetic material at a target site in the cell's genome, which restores, corrects, disrupts, and/or modifies expression of a gene or gene product. Genome editing contemplated in particular embodiments comprises introducing one or more nuclease variants into a cell to generate DNA lesions at or proximal to a target site in the cell's genome, optionally in the presence of a donor repair template.

As used herein, the term "gene therapy" refers to the introduction of extra genetic material into the total genetic material in a cell that restores, corrects, or modifies expression of a gene or gene product, or for the purpose of expressing a therapeutic polypeptide. In particular embodiments, introduction of genetic material into the cell's genome by genome editing that restores, corrects, disrupts, or modifies expression of a gene or gene product, or for the purpose of expressing a therapeutic polypeptide is considered gene therapy.

As used herein, the terms "individual" and "subject" are often used interchangeably and refer to any animal that exhibits a symptom of an immune disorder that can be treated with the nuclease variants, genome editing compositions, gene therapy vectors, genome editing vectors, genome edited cells, and methods contemplated elsewhere herein. Suitable subjects (e.g., patients) include laboratory animals (such as mouse, rat, rabbit, or guinea pig), farm animals, and domestic animals or pets (such as a cat or dog). Non-human primates and, preferably, human subjects, are included. Typical subjects include human patients that have, have been diagnosed with, or are at risk of having an immune disorder.

As used herein, the term "patient" refers to a subject that has been diagnosed with an immune disorder that can be treated with the nuclease variants, genome editing compositions, gene therapy vectors, genome editing vectors, genome edited cells, and methods contemplated elsewhere herein.

"Autologous," as used herein, refers to cells where the donor and recipient are the same subject.

"Allogeneic," as used herein, refers to cells wherein the donor and recipient species are the same but the cells are genetically different.

"Syngeneic," as used herein, refers to cells wherein the donor and recipient species are the same, the donor and recipient are different individuals, and the donor cells and recipient cells are genetically identical.

"Xenogeneic," as used herein, refers to cells wherein the donor and recipient species are different.

As used herein "treatment" or "treating," includes any beneficial or desirable effect on the symptoms or pathology of a disease or pathological condition, and may include even minimal reductions in one or more measurable markers of the disease or condition being treated, e.g., a hemoglobinopathy, cancer, GVHD, infectious disease, autoimmune disease, inflammatory disease, and immunodeficiency. Treatment can optionally involve delaying of the progression of the disease or condition. "Treatment" does not necessarily indicate complete eradication or cure of the disease or condition, or associated symptoms thereof.

As used herein, "prevent," and similar words such as "prevention," "prevented," "preventing" etc., indicate an approach for preventing, inhibiting, or reducing the likelihood of the occurrence or recurrence of, a disease or condition, e.g., a hemoglobinopathy, cancer, GVHD, infectious disease, autoimmune disease, inflammatory disease, and immunodeficiency. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the phrase "ameliorating at least one symptom of" refers to decreasing one or more symptoms of the disease or condition for which the subject is being treated, e.g., a hemoglobinopathy, cancer, GVHD, infectious disease, autoimmune disease, inflammatory disease, and immunodeficiency. In particular embodiments, the hemoglobinopathy or hemoglobinopathic condition being treated is β-thalassemia, wherein the one or more symptoms ameliorated include, but are not limited to, weakness, fatigue, pale appearance, jaundice, facial bone deformities, slow growth, abdominal swelling, dark urine, iron deficiency (in the absence of transfusion), requirement for frequent transfusions. In particular embodiments, the hemoglobinopathy or hemoglobinopathic condition being treated is sickle cell disease (SCD) wherein the one or more symptoms ameliorated include, but are not limited to, anemia; unexplained episodes of pain, such as pain in the abdomen, chest, bones or joints; swelling in the hands or feet; abdominal swelling; fever; frequent infections; pale skin or nail beds; jaundice; delayed growth; vision problems; signs or symptoms of stroke; iron deficiency (in the absence of transfusion), requirement for frequent transfusions. In particular embodiments, the disease or condition being treated is a cancer, wherein the one or more symptoms ameliorated include, but are not limited to, weakness, fatigue, shortness of breath, easy bruising and bleeding, frequent infections, enlarged lymph nodes, distended or painful abdomen (due to enlarged abdominal organs), bone or joint pain, fractures, unplanned weight loss, poor appetite, night sweats, persistent mild fever, and decreased urination (due to impaired kidney function).

As used herein, the term "amount" refers to "an amount effective" or "an effective amount" of a DNA donor repair template, nuclease variant, genome editing composition, or genome edited cell sufficient to achieve a beneficial or desired prophylactic or therapeutic result, including clinical results.

A "prophylactically effective amount" refers to an amount of a DNA donor repair template, nuclease variant, genome editing composition, or genome edited cell sufficient to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a DNA donor repair template, nuclease variant, genome editing composition, or genome edited cell may vary according to factors such as the disease state, age, sex, and weight of the individual, and the ability to elicit a desired response in the individual. A therapeutically effective amount is also one in which any toxic or detrimental effects are outweighed by the therapeutically beneficial effects. The term "therapeutically effective amount" includes an amount that is effective to "treat" a subject (e.g., a patient). When a therapeutic amount is indicated, the precise amount of the compositions contemplated in particular embodiments, to be administered, can be determined by a physician in view of the specification and with consideration of individual differences in age, weight, tumor size, extent of infection or metastasis, and condition of the patient (subject).

As used herein, the term "hemoglobinopathy" or "hemoglobinopathic condition" refers to a diverse group of inherited blood disorders that involve the presence of abnormal hemoglobin molecules resulting from alterations in the structure and/or synthesis of hemoglobin.

An "immune disorder" refers to a disease that evokes a response from the immune system. In particular embodiments, the term "immune disorder" refers to a cancer, graft-versus-host disease, an autoimmune disease, or an immunodeficiency. In one embodiment, immune disorders encompasses infectious disease.

As used herein, the term "cancer" relates generally to a class of diseases or conditions in which abnormal cells divide without control and can invade nearby tissues.

As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood).

As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancers form tumors, but some, e.g., leukemia, do not necessarily form tumors. For those cancers that form tumors, the terms cancer (cell) and tumor (cell) are used interchangeably. The amount of a tumor in an individual is the "tumor burden" which can be measured as the number, volume, or weight of the tumor.

"Graft-versus-host disease" or "GVHD" refers complications that can occur after cell, tissue, or solid organ transplant. GVHD can occur after a stem cell or bone marrow transplant in which the transplanted donor cells attack the transplant recipient's body. Acute GVHD in humans takes place within about 60 days post-transplantation and results in damage to the skin, liver, and gut by the action of cytolytic lymphocytes. Chronic GVHD occurs later and is a systemic autoimmune disease that affects primarily the skin, resulting in the polyclonal activation of B cells and the hyperproduction of Ig and autoantibodies. Solid-organ transplant graft-versus-host disease (SOT-GVHD) occurs in two forms. The more common type is antibody mediated, wherein antibodies from a donor with blood type O attack a recipient's red blood cells in recipients with blood type A, B, or AB, leading to mild transient, hemolytic anemias. The second form of SOT-GVHD is a cellular type associated with high mortality, wherein donor-derived T cells produce an immunological attack against immunologically disparate host tissue, most often in the skin, liver, gastrointestinal tract, and bone marrow, leading to complications in these organs.

"Graft-versus-leukemia" or "GVL" refer to an immune response to a person's leukemia cells by immune cells present in a donor's transplanted tissue, such as bone marrow or peripheral blood.

An "autoimmune disease" refers to a disease in which the body produces an immunogenic (i.e., immune system) response to some constituent of its own tissue. In other words, the immune system loses its ability to recognize some tissue or system within the body as "self" and targets and attacks it as if it were foreign. Illustrative examples of autoimmune diseases include, but are not limited to: arthritis, inflammatory bowel disease, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

An "immunodeficiency" means the state of a patient whose immune system has been compromised by disease or by administration of chemicals. This condition makes the system deficient in the number and type of blood cells needed to defend against a foreign substance. Immunodeficiency conditions or diseases are known in the art and include, for example, AIDS (acquired immunodeficiency syndrome), SCID (severe combined immunodeficiency disease), selective IgA deficiency, common variable immunodeficiency, X-linked agammaglobulinemia, chronic granulomatous disease, hyper-IgM syndrome, Wiskott-Aldrich Syndrome (WAS), and diabetes.

An "infectious disease" refers to a disease that can be transmitted from person to person or from organism to organism, and is caused by a microbial or viral agent (e.g., common cold). Infectious diseases are known in the art and include, for example, hepatitis, sexually transmitted diseases (e.g., *Chlamydia*, gonorrhea), tuberculosis, HIV/AIDS, diphtheria, hepatitis B, hepatitis C, cholera, and influenza.

C. Donor Repair Templates

The donor repair templates contemplated herein are suitable for multiplex genome editing using a single donor molecule and one or more engineered nucleases. The donor repair templates contemplated herein offer a quantum improvement compared to existing methods, which are cumbersome and often require multiple rounds of editing and separate donor templates and corresponding engineered nucleases for each locus to be edited. In particular embodiments, a plurality of engineered nucleases are used to introduce a DSB in a plurality of target sites and the DSB is repaired at each of the target sites through homology directed repair (HDR) mechanisms in the presence of a single DNA donor repair template that targets the plurality of target sites.

In particular embodiments, the DNA donor repair template is used to insert one or more sequences into multiple sites in a genome. In particular preferred embodiments, the donor repair template is used to repair or modify a plurality of target site sequence in a genome.

In various embodiments, a donor repair template is introduced into a hematopoietic cell, e.g., an HSC, a $CD34^+$ cell, a T cell, etc. by transducing the cell with an adeno-associated virus (AAV), retrovirus, e.g., lentivirus, IDLV, etc., herpes simplex virus, adenovirus, or vaccinia virus vector comprising the donor repair template.

In certain embodiments, a donor repair template is introduced into a hematopoietic cell, e.g., an HSC, a $CD34^+$ cell, a T cell, etc. by introducing a single-stranded DNA, double-stranded DNA, plasmid, or minicircle DNA comprising the donor repair template into the cell.

In various embodiments, the DNA donor repair template comprises a plurality of homology arms corresponding to a plurality of target sites in a genome.

In various embodiments, the DNA donor repair template comprises a plurality of pairs of homology arms corresponding to a plurality of target sites in a genome, wherein each pair of homology arms flanks one or more transgenes.

In some embodiments, the DNA donor repair template comprises a plurality of pairs of homology arms corresponding to a plurality of target sites in a genome, wherein each pair of homology arms flanks a different transgene.

In various embodiments, the DNA donor repair template comprises a plurality of pairs of homology arms corresponding to a plurality of target sites in a genome, wherein each pair of homology arms flanks one or more transgenes, wherein at least two of the pairs of homology arms flank the same transgene.

A "pair of homology arms" refers to a group of two homology arms. In particular embodiments a pair of homology arms comprises a 5' homology arm and a 3' homology arm. A "5' homology arm" refers to a polynucleotide sequence that is identical, or nearly identical, or homologous to a DNA sequence 5' of a target site (e.g., double strand break site). A "3' homology arm" refers to a polynucleotide sequence that is identical, or nearly identical, or homologous to a DNA sequence 3' of the target site. In particular embodiments, a pair of homology arms comprises a homology arm comprising a polynucleotide sequence that includes a target site for a double strand break with a mutation in the target site to minimize recleavage of the target site. In particular embodiments, either one of, or both, homology arms in a pair of homology arms is independently located about 100 bp, about 200 bp, about 300 bp, about 400 bp, about 500 bp, about 600 bp, about 700 bp, about 800 bp, about 900 bp, about 1000 bp, about 1100 bp, about 1200 bp, about 1300 bp, about 1400 bp, about 1500 bp, about 1600 bp, about 1700 bp, about 1800 bp, about 1900 bp, about 2000 bp, about 2100 bp, about 2200 bp, about 2300 bp, about 2400 bp, about 2500 bp, about 2600 bp, about 2700 bp, about 2800 bp, about 2900 bp, or about 3000 bp, from the target site, including all intervening distances from the target site.

Illustrative examples of suitable lengths of homology arms contemplated in particular embodiments, may be independently selected, and include but are not limited to: about 100 bp, about 200 bp, about 300 bp, about 400 bp, about 500 bp, about 600 bp, about 700 bp, about 800 bp, about 900 bp, about 1000 bp, about 1100 bp, about 1200 bp, about 1300 bp, about 1400 bp, about 1500 bp, about 1600 bp, about 1700 bp, about 1800 bp, about 1900 bp, about 2000 bp, about 2100 bp, about 2200 bp, about 2300 bp, about 2400 bp, about 2500 bp, about 2600 bp, about 2700 bp, about 2800 bp, about 2900 bp, or about 3000 bp, or longer homology arms, including all intervening lengths of homology arms.

Additional illustrative examples of suitable homology arm lengths include, but are not limited to: about 100 bp to about 600 bp, about 100 bp to about 500 bp, about 100 bp to about 400 bp, about 100 bp to about 300 bp, about 100 bp to about 200 bp, about 200 bp to about 600 bp, about 200 bp to about 500 bp, about 200 bp to about 400 bp, about 200 bp to about 300 bp, about 300 bp to about 600 bp, about 300 bp to about 500 bp, about 100 bp to about 3000 bp, about 200 bp to about 3000 bp, about 300 bp to about 3000 bp, about 400 bp to about 3000 bp, about 500 bp to about 3000 bp, about 500 bp to about 2500 bp, about 500 bp to about 2000 bp, about 750 bp to about 2000 bp, about 750 bp to about 1500 bp, or about 1000 bp to about 1500 bp, including all intervening lengths of homology arms.

In a particular embodiment, the lengths of any 5' and 3' homology arms present in a DNA donor repair template are independently selected from about 100 bp, about 200 bp, about 300 bp, about 400 bp, about 500 bp, or about 600 bp. In one embodiment, a 5' homology arm is about 300 bp and a 3' homology arm is about 300 bp. In one embodiment, each of the plurality of 5' homology arms in a DNA donor repair template is about 300 bp and each of the plurality of 3' homology arms in a DNA donor repair template is about 300 bp.

In particular embodiments, a DNA donor repair template comprises a plurality of pairs of homology arms and one or more transgenes.

In particular embodiments, a DNA donor repair template comprises a plurality of pairs of homology arms and a transgene. In certain embodiments, each of the pairs of homology arms comprises a 5' homology arm that is homologous to the DNA sequence 5' of a target site and a 3' homology arm that is homologous to the DNA sequence 3' of the target site, wherein each of the pairs of homology arms is associated with a different target site. In a particular embodiment, a DNA donor repair template comprises a first pair of homology arms that comprises a 5' homology arm that is homologous to a DNA sequence 5' of a first target site and a 3' homology arm that is homologous to a DNA sequence 3' of the first target site; and a 5' homology arm that is homologous to a DNA sequence 5' of a second target site and a 3' homology arm that is homologous to a DNA sequence 3' of the second target site, wherein the first target site is not identical to the second target site.

In particular embodiments, each of the pairs of homology arms flanks the same transgene sequence, each 5' homology arm is positioned 5' to the transgene and each 3' homology arm is positioned 3' to the transgene. In particular embodiments, a DNA donor repair templates comprises a 5' homology arm that is homologous to a DNA sequence 5' of a first target site and located 5' of a 5' homology arm that is homologous to a DNA sequence 5' of a second target site, both 5' homology arms being positioned 5' to a transgene; and a 3' homology arm that is homologous to a DNA sequence 3' to the first target site and located 3' of a 3' homology arm that is homologous to a DNA sequence 3' to the second target site, both 3' homology arms being positioned 3' of the transgene.

In particular embodiments, each of the pairs of homology arms flanks the same transgene sequence, each 5' homology arm is positioned 5' to the transgene and each 3' homology arm is positioned 3' to the transgene. In particular embodiments, a DNA donor repair templates comprises a 5' homology arm that is homologous to a DNA sequence 5' of a first target site and located 5' to a 5' homology arm that is homologous to a DNA sequence 5' of a second target site, both 5' homology arms being positioned 5' to a transgene; and a 3' homology arm that is homologous to a DNA sequence 3' to the first target site and located 5' of a 3' homology arm that is homologous to a DNA sequence 3' to the second target site, both 3' homology arms being positioned 3' of the transgene.

In particular embodiments, each of the pairs of homology arms flanks a different transgene sequence, a first pair of homology arms flanks a first transgene and a second pair of homology arms flanks a second transgene. In particular embodiments, DNA donor repair template comprises a first pair of homology arms comprising a 5' homology arm that is homologous to a DNA sequence 5' to a first target site and located 5' to a first transgene and a 3' homology arm that is homologous to a DNA sequence 3' to the first target site and located 3' the first transgene; and a second pair of homology arms comprising a 5' homology arm that is homologous to a DNA sequence 5' to a second target site and located 5' to a second transgene and a 3' homology arm that is homologous to a DNA sequence 3' to the second target site and located 3' to the second transgene.

In preferred embodiments, a DNA donor repair template encodes one or more transgenes that increases the efficacy of a cell-based gene therapy for treating or preventing a hemoglobinopathy, or ameliorating at least one symptom of a hemoglobinopathy. In particular embodiments, a DNA donor repair template comprises one or more transgenes encoding an a globin polypeptide, including but not limited to a β-globin polypeptide, an anti-sickling β-globin polypeptide (e.g., $\beta^{A-T87Q}$, $\beta^{A-K120E}$, $\beta^{A-K95E}$ or a combination thereof), or a γ-globin polypeptide.

In preferred embodiments, a DNA donor repair template encodes one or more transgenes that increases the safety, efficacy, durability, and/or persistence of an adoptive cell therapy. In particular embodiments, a DNA donor repair template comprises one or more transgenes encoding an immunopotency enhancer, an immunosuppressive signal damper, or an engineered antigen receptor. In particular embodiments, a DNA donor template is designed to insert the one or more transgenes (via HDR) into multiple loci that encode genes that contribute to TCR signaling, immune system checkpoints, and/or immunosuppressive signaling.

Donor repair templates may further comprises one or more polynucleotides such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, contemplated elsewhere herein.

1. Immunopotency Enhancers

In particular embodiments, the genome edited immune effector cells contemplated herein are made more potent by introducing a DSB into one or more genes encoding a TCR signaling component (e.g., constant region of TCRα gene), an immune system checkpoint, or an immunosuppressive signaling component in the presence of a donor repair template encoding an immunopotency enhancer. As used herein, the term "immunopotency enhancer" refers to non-naturally occurring molecules that stimulate and/or potentiate T cell activation and/or function, immunopotentiating factors, and non-naturally occurring polypeptides that convert the immunosuppressive signals from the tumor microenvironment to an immunostimulatory signal in a T cell.

In particular embodiments, a DNA donor template is designed to insert an immunopotency enhancer into one locus and one or more transgenes encoding another immunopotency enhancer, an immunosuppressive signal damper, or an engineered antigen receptor into one or more different loci.

In particular embodiments, the immunopotency enhancer is selected from the group consisting of: a bispecific T cell engager (BiTE) molecule; an immunopotentiating factor including, but not limited to, cytokines, chemokines, cytotoxins, and/or cytokine receptors; and a flip receptor.

In some embodiments, the immunopotency enhancer, immunopotentiating factor, or flip receptor are fusion polypeptides comprising a protein destabilization domain.

a. Bispecific T Cell Engager (BiTE) Molecules

In particular embodiments, the genome edited immune effector cells contemplated herein are made more potent by introducing a DSB into one or more genes encoding a TCR signaling component (e.g., constant region of TCRα gene), an immune system checkpoint, or an immunosuppressive signaling component in the presence of a donor repair template encoding a bispecific T cell engager (BiTE) molecules. BiTE molecules are bipartite molecules comprising a first binding domain that binds a target antigen, a linker or spacer as contemplated elsewhere herein, and a second binding domain that binds a stimulatory or costimulatory molecule on an immune effector cell. The first and second binding domains may be independently selected from ligands, receptors, antibodies or antigen binding fragments thereof, lectins, and carbohydrates.

In particular embodiments, the first and second binding domains are antigen binding domains.

In particular embodiments, the first and second binding domains are antibodies or antigen binding fragments thereof. In one embodiment, the first and second binding domains are single chain variable fragments (scFv).

Illustrative examples of target antigens that may be recognized and bound by the first binding domain in particular embodiments include, but are not limited to: alpha folate receptor, trophoblast glycoprotein (TPBG); αvβ6 integrin; B cell maturation antigen (BCMA); B7-H3; B7-H6; CD276; CD16; CD19; CD20; CD22; CD30; CD33; CD44; CD44v6; CD44v7/8; CD70; CD79a; CD79b; CD123; CD138; CD171; a carcinoembryonic antigen (CEA) polypeptide; chondroitin sulfate proteoglycan 4 (CSPG4); epidermal growth factor receptor (EGFR); erb-b2 receptor tyrosine kinase 2 (ERBB2); EGFR gene amplification and variant III (EGFRvIII); epithelial cell adhesion molecule (EPCAM); ephrin A2 (EphA2); fibroblast activation protein alpha (FAP); fetal acetylcholine receptor (fetal AchR); bDGalpNAc(1-4)[aNeu5Ac(2-8)aNeu5Ac(2-3)]bDGalp(1-4)bDGlcp(1-1)Cer (GD2); aNeu5Ac(2-8)aNeu5Ac(2-3)bD-Galp(1-4)bDGlcp(1-1)Cer (GD3); glypican-3 (GPC3); human leukocyte antigen A1 MAGE family member A1 (HLA-A1$^+$MAGEA1); human leukocyte antigen A2 MAGE family member A1 (HLA-A2$^+$MAGEA1); human leukocyte antigen A3 MAGE family member A1 (HLA-A3$^+$MAGEA1); MAGEA1; human leukocyte antigen A1 New York Esophageal Squamous Cell Carcinoma 1 (HLA-A1$^+$NY-ESO-1); human leukocyte antigen A2 New York Esophageal Squamous Cell Carcinoma 1 (HLA-A2$^+$NY-ESO-1); human leukocyte antigen A3 New York Esophageal Squamous Cell Carcinoma 1 (HLA-A3$^+$NY-ESO-1); interleukin receptor 11 alpha (IL-11Rα); interleukin-13 receptor subunit alpha-2 (IL-13Rα2); lambda light chain; lewis-Y; kappa light chain; mesothelin; mucin 1, cell surface associated (MUC1); mucin 16, cell surface associated (MUC16), neural cell adhesion molecule (NCAM), natural killer group 2D (NKG2D) ligands, NY-ESO-1, preferentially expressed antigen in melanoma (PRAME), prostate stem cell antigen (PSCA), prostate specific membrane antigen (PSMA), receptor tyrosine kinase like orphan receptor 1 (ROR1), synovial sarcoma X (SSX), survivin, tumor-associated glycoprotein 72 (TAG72), tumor endothelial marker 1 (TEM1), tumor endothelial marker 5 (TEM5), tumor endothelial marker 7 (TEM7), tumor endothelial marker 8 (TEM8), vascular endothelial growth factor receptor 2 (VEGFR2), and Wilm' tumor 1 (WT-1).

Other illustrative embodiments of target antigens include MHC-peptide complexes, optionally wherein the peptide is processed from: FRα, TPBG, αvβ6 integrin, BCMA, B7-H3, B7-H6, CD276, CD16, CD19, CD20, CD22, CD30, CD33, CD44, CD44v6, CD44v7/8, CD70, CD79a, CD79b, CD123, CD138, CD171, CEA, CSPG4, EGFR, ERBB2, EGFRvIII, EPCAM, EphA2, FAP, fetal AchR, GD2, GD3, GPC3, HLA-A1$^+$MAGEA1, HLA-A2$^+$MAGEA1, HLA-A3$^+$MAGEA1, MAGEA1, HLA-A1$^+$NY-ESO-1, HLA-A2$^+$NY-ESO-1, HLA-A3$^+$NY-ESO-1, IL-11Rα, IL-13Rα2, lambda light chain, lewis-Y, kappa light chain, mesothelin, MUC1, MUC16, NCAM, NKG2D ligands, NY-ESO-1, PRAME, PSCA, PSMA, ROR1, SSX, survivin, TAG72, TEM1, TEM5, TEM7, TEM8, VEGFR2, and WT-1.

Illustrative examples of stimulatory or co-stimulatory molecules on immune effector cells recognized and bound by the second binding domain in particular embodiments include, but are not limited to: CD3γ, CD3δ, CD3ε, CD3ζ, CD28, CD40, CD80, CD86, CD134, CD137, and CD278.

In particular embodiments, a plurality of engineered nucleases are used to induce a DSB in multiple target sites in a genome, and a DNA donor repair template comprising a transgene encoding a BiTE and flanked by a plurality of homology arms corresponding to a plurality of target sites in a genome is introduced into the cell and is inserted into at least one of the target sites by homologous recombination.

In particular embodiments, a plurality of engineered nucleases are used to induce a DSB in multiple target sites in a genome, and a DNA donor repair template comprising a transgene encoding a BiTE and flanked by a plurality of homology arms corresponding to a plurality of target sites in a genome is introduced into the cell and is inserted into two or more of the target sites by homologous recombination.

In particular embodiments, a plurality of engineered nucleases are used to induce a DSB in multiple target sites in a genome, and a DNA donor repair template comprising a transgene encoding a BiTE and flanked by a plurality of homology arms corresponding to a plurality of target sites in a genome is introduced into the cell and is inserted into each of the target sites by homologous recombination.

b. Immunopotentiating Factors

In particular embodiments, the genome edited immune effector cells contemplated herein are made more potent by introducing a DSB into one or more genes encoding a TCR signaling component (e.g., constant region of TCRα gene), an immune system checkpoint, or an immunosuppressive signaling component in the presence of a donor repair template encoding an immunopotentiating factor. Immunopotentiating factors refer to particular cytokines, chemokines, cytotoxins, and cytokine receptors that potentiate the immune response in immune effector cells.

In particular embodiments, the donor repair template encodes a cytokine selected from the group consisting of: IL-2, insulin, IFN-γ, IL-7, IL-21, IL-10, IL-12, IL-15, and TNF-α.

In particular embodiments, the donor repair template encodes a chemokine selected from the group consisting of: MIP-1α, MIP-1β, MCP-1, MCP-3, and RANTES.

In particular embodiments, the donor repair template encodes a cytotoxin selected from the group consisting of Perforin, Granzyme A, and Granzyme B.

In particular embodiments, the donor repair template encodes a cytokine receptor selected from the group consisting of: an IL-2 receptor, an IL-7 receptor, an IL-12 receptor, an IL-15 receptor, and an IL-21 receptor.

In particular embodiments, a plurality of engineered nucleases are used to induce a DSB in multiple target sites in a genome, and a DNA donor repair template comprising a transgene encoding an immunopotentiating factor and flanked by a plurality of homology arms corresponding to a plurality of target sites in a genome is introduced into the cell and is inserted into at least one of the target sites by homologous recombination.

In particular embodiments, a plurality of engineered nucleases are used to induce a DSB in multiple target sites in a genome, and a DNA donor repair template comprising a transgene encoding an immunopotentiating factor and flanked by a plurality of homology arms corresponding to a plurality of target sites in a genome is introduced into the cell and is inserted into two or more of the target sites by homologous recombination.

In particular embodiments, a plurality of engineered nucleases are used to induce a DSB in multiple target sites in a genome, and a DNA donor repair template comprising a transgene encoding an immunopotentiating factor and flanked by a plurality of homology arms corresponding to a plurality of target sites in a genome is introduced into the cell and is inserted into each of the target sites by homologous recombination.

c. Flip Receptors

In particular embodiments, the genome edited immune effector cells contemplated herein are made more resistant to exhaustion by "flipping" or "reversing" the immunosuppressive signal elicited by immunosuppressive factors elicited by the tumor microenvironment to a positive immunostimulatory signal. In one embodiment, T cells are engineered by introducing a DSB into one or more genes encoding a TCR signaling component (e.g., constant region of TCRα gene), an immune system checkpoint, or an immunosuppressive signaling component in the presence of a donor repair template encoding a flip receptor. As used herein, the term "flip receptor" refers to a non-naturally occurring polypeptide that converts the immunosuppressive signals from the tumor microenvironment to an immunostimulatory signal in a T cell. In preferred embodiments, a flip receptor refers to a polypeptide that comprises an exodomain that binds an immunosuppressive factor, a transmembrane domain, and an endodomain that transduces an immunostimulatory signal to a T cell.

In one embodiment, the donor repair template comprises a flip receptor comprising an exodomain or extracellular binding domain that binds an immunosuppressive cytokine, a transmembrane domain, and an endodomain of an immunopotentiating cytokine receptor.

In particular embodiments, a flip receptor comprises an exodomain that binds an immunosuppressive cytokine is the extracellular cytokine binding domain of an IL-4 receptor, IL-6 receptor, IL-8 receptor, IL-10 receptor, IL-13 receptor, or TGFβ receptor; a transmembrane isolated from CD4, CD8α, CD27, CD28, CD134, CD137, a CD3 polypeptide, IL-2 receptor, IL-7 receptor, IL-12 receptor, IL-15 receptor, or IL-21 receptor; and an endodomain isolated from an IL-2 receptor, IL-7 receptor, IL-12 receptor, IL-15 receptor, or IL-21 receptor.

In particular embodiments, a flip receptor comprises an exodomain that binds an immunosuppressive cytokine is an antibody or antigen binding fragment thereof that binds IL-4, IL-6, IL-8, IL-10, IL-13, or TGFβ; a transmembrane isolated from CD4, CD8α, CD27, CD28, CD134, CD137, a CD3 polypeptide, IL-2 receptor, IL-7 receptor, IL-12 receptor, IL-15 receptor, or IL-21 receptor; and an endodomain isolated from an IL-2 receptor, IL-7 receptor, IL-12 receptor, IL-15 receptor, or IL-21 receptor.

In one embodiment, the donor repair template comprises a flip receptor comprising an exodomain that binds an immunosuppressive factor, a transmembrane domain, and one or more intracellular co-stimulatory signaling domains and/or primary signaling domains.

Illustrative examples of exodomains suitable for use in particular embodiments of flip receptors contemplated in particular embodiments include, but are not limited to: an extracellular ligand binding domain of a receptor that comprises an ITIM and/or an ITSM.

Further illustrative examples of exodomains suitable for use in particular embodiments of flip receptors contemplated in particular embodiments include, but are not limited to an extracellular ligand binding domain of: PD-1, LAG-3, TIM-3, CTLA-4, BTLA, CEACAM1, TIGIT, TGFβRII, IL4R, IL6R, CXCR1, CXCR2, IL10R, IL13Rα2, TRAILR1, RCAS1R, and FAS.

In one embodiment, the exodomain comprises an extracellular ligand binding domain of a receptor selected from the group consisting of: PD-1, LAG-3, TIM-3, CTLA-4, IL10R, TIGIT, and TGFβRII.

In one embodiment, the donor repair template comprises a flip receptor comprising an exodomain that binds an immunosuppressive cytokine, a transmembrane domain, and one or more intracellular co-stimulatory signaling domains and/or primary signaling domains.

Illustrative examples of transmembrane domains suitable for use in particular embodiments of flip receptors contemplated in particular embodiments include, but are not limited to transmembrane domains of the following proteins: PD-1, LAG-3, TIM-3, CTLA-4, IL10R, TIGIT, and TGFβRII alpha or beta chain of the T-cell receptor, CDδ, CD3ε, CDγ, CD3ζ, CD4, CD5, CD8α, CD9, CD 16, CD22, CD27, CD28, CD33, CD37, CD45, CD64, CD80, CD86, CD 134, CD137, or CD154. In particular embodiments, it may be preferred to select a transmembrane domain that associates with the TCR signaling complex, e.g., CD3, to increase the immunostimulatory signal.

In various embodiments, the flip receptor comprises an endodomain that elicits an immunostimulatory signal. As used herein, the term "endodomain" refers to an immunostimulatory motif or domain, including but not limited to an immunoreceptor tyrosine activation motif (ITAM), a costimulatory signaling domain, a primary signaling domain, or another intracellular domain that is associated with eliciting immunostimulatory signals in T cells.

Illustrative examples of endodomains suitable for use in particular embodiments of flip receptors contemplated in particular embodiments include, but are not limited to domains comprising an ITAM motif.

Additional illustrative examples of endodomains suitable for use in particular embodiments of flip receptors contemplated in particular embodiments include, but are not limited to co-stimulatory signaling domains is isolated from: TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, or ZAP70.

Additional illustrative examples of endodomains suitable for use in particular embodiments of flip receptors contemplated in particular embodiments include, but are not limited to: an endodomain isolated from an IL-2 receptor, IL-7 receptor, IL-12 receptor, IL-15 receptor, or IL-21 receptor.

Further illustrative examples of endodomains suitable for use in particular embodiments of flip receptors contemplated in particular embodiments include, but are not limited to primary signaling domains is isolated from: FcRγ, FcRβ, CD3γ, CD3δ, CD3ε, CD3ζ, CD22, CD79a, CD79b, and CD66d.

In particular embodiments, the flip receptor comprises an exodomain that comprises an extracellular domain from PD-1, LAG-3, TIM-3, CTLA-4, IL10R, TIGIT, or TGFβRII; a transmembrane domain from a CD3 polypeptide, CD4, CD8α, CD28, CD134, CD137, PD-1, LAG-3, TIM-3, CTLA-4, IL10R, and TGFβRII; and endodomain from CD28, CD134, CD137, CD278, and/or CD3ζ.

In particular embodiments, the flip receptor comprises an exodomain that comprises an extracellular domain from PD-1, LAG-3, TIM-3, CTLA-4, IL10R, TIGIT, or TGFβRII; a transmembrane domain from a CD3 polypeptide, CD4, CD8α, CD28, CD134, or CD137; and endodomain from CD28, CD134, CD137, CD278, and/or CD3ζ.

In particular embodiments, a plurality of engineered nucleases are used to induce a DSB in multiple target sites in a genome, and a DNA donor repair template comprising a transgene encoding a flip receptor and flanked by a plurality of homology arms corresponding to a plurality of target sites in a genome is introduced into the cell and is inserted into at least one of the target sites by homologous recombination.

In particular embodiments, a plurality of engineered nucleases are used to induce a DSB in multiple target sites in a genome, and a DNA donor repair template comprising a transgene encoding a flip receptor and flanked by a plurality of homology arms corresponding to a plurality of target sites in a genome is introduced into the cell and is inserted into two or more of the target sites by homologous recombination.

In particular embodiments, a plurality of engineered nucleases are used to induce a DSB in multiple target sites in a genome, and a DNA donor repair template comprising a transgene encoding a flip receptor and flanked by a plurality of homology arms corresponding to a plurality of target sites in a genome is introduced into the cell and is inserted into each of the target sites by homologous recombination.

i. PD-1 Flip Receptor

PD-1 is expressed on T cells and is subject to immunosuppression by immunosuppressive factors present in the tumor microenvironment. The expression of PD-L1 and PD-L2 correlates with prognosis in some human malignancies. The PD-L1/PD-1 signaling pathway is one important regulatory pathway of T cell exhaustion. PD-L1 is abundantly expressed in cancer cells and stromal cells, and blockade of PD-L1/PD-1 using monoclonal antibodies enhances T cell anti-tumor function. PD-L2 also binds to PD-1 and negatively regulates T cell function.

In one embodiment, a DSB is introduced in one or more genes encoding a TCR signaling component (e.g., constant region of TCRα gene), an immune system checkpoint, or an immunosuppressive signaling component by an engineered nuclease in the presence of a donor repair template comprising one or more pairs of homology arms flanking a transgene encoding a PD-1 flip receptor that is inserted into the one or more genes at the DSB by homologous recombination.

PD-1 flip receptors contemplated in particular embodiments comprise the extracellular ligand binding domain of the human PD-1 receptor, a transmembrane domain from PD-1, a CD3 polypeptide, CD4, CD8α, CD28, CD134, or CD137, and an endodomain from CD28, CD134, CD137, CD278, and/or CD3ζ.

ii. LAG-3 Flip Receptor

Lymphocyte activation gene-3 (LAG-3) is a cell-surface molecule with diverse biologic effects on T cell function. LAG-3 signaling is associated with CD4$^+$ regulatory T cell suppression of autoimmune responses. In addition, LAG-3 expression increases upon antigen stimulation of CD8$^+$ T cells and is associated with T cell exhaustion in the tumor microenvironment. In vivo antibody blockade of LAG-3 is associated with increased accumulation and effector function of antigen-specific CD8$^+$ T cells. One group showed that administration of anti-LAG-3 antibodies in combination with specific antitumor vaccination resulted in a significant increase in activated CD8$^+$ T cells in the tumor and disruption of the tumor parenchyma. Grosso et al. (2007). *J Clin Invest.* 117(11):3383-3392.

In one embodiment, a DSB is introduced in one or more genes encoding a TCR signaling component (e.g., constant region of TCRα gene), an immune system checkpoint, or an immunosuppressive signaling component by an engineered nuclease in the presence of a donor repair template comprising one or more pairs of homology arms flanking a transgene encoding a LAG-3 flip receptor that is inserted into the one or more genes at the DSB by homologous recombination.

LAG-3 flip receptors contemplated in particular embodiments comprise the extracellular ligand binding domain of the human LAG-3 receptor, a transmembrane domain from LAG-3, a CD3 polypeptide, CD4, CD8α, CD28, CD134, or CD137, and an endodomain from CD28, CD134, CD137, CD278, and/or CD3ζ.

iii. TIM-3 Flip Receptor

T cell immunoglobulin-3 (TIM-3) has been established as a negative regulatory molecule and plays a role in immune tolerance. TIM-3 expression identifies exhausted T cells in cancers and during chronic infection. TIM-3-expressing CD4$^+$ and CD8$^+$ T cells produce reduced amounts of cytokine or are less proliferative in response to antigen. Increased TIM-3 expression is associated with decreased T cell proliferation and reduced production of IL-2, TNF, and IFN-γ. Blockade of the TIM-3 signaling pathway restores proliferation and enhances cytokine production in antigen specific T cells.

TIM-3 is co-expressed and forms a heterodimer with carcinoembryonic antigen cell adhesion molecule 1 (CEACAM1), another well-known molecule expressed on activated T cells and involved in T-cell inhibition. The presence of CEACAM1 endows TIM-3 with inhibitory function. CEACAM1 facilitates the maturation and cell surface expression of TIM-3 by forming a heterodimeric interaction in cis through the highly related membrane-distal N-terminal domains of each molecule. CEACAM1 and TIM-3 also bind in trans through their N-terminal domains.

In one embodiment, a DSB is introduced in one or more genes encoding a TCR signaling component (e.g., constant region of TCRα gene), an immune system checkpoint, or an immunosuppressive signaling component by an engineered nuclease in the presence of a donor repair template comprising one or more pairs of homology arms flanking a transgene encoding a TIM-3 flip receptor that is inserted into the one or more genes at the DSB by homologous recombination.

TIM-3 flip receptors contemplated in particular embodiments comprise the extracellular ligand binding domain of the human TIM-3 receptor, a transmembrane domain from TIM-3, a CD3 polypeptide, CD4, CD8α, CD28, CD134, or CD137, and an endodomain from CD28, CD134, CD137, CD278, and/or CD3ζ.

iv. CTLA-4 Flip Receptor

CTLA4 is expressed primarily on T cells, where it regulates the amplitude of the early stages of T cell activation. CTLA4 counteracts the activity of the T cell co-stimulatory receptor, CD28. CD28 does not affect T cell activation unless the TCR is first engaged by cognate antigen. Once antigen recognition occurs, CD28 signaling strongly amplifies TCR signaling to activate T cells. CD28 and CTLA4 share identical ligands: CD80 (also known as B7.1) and CD86 (also known as B7.2). CTLA4 has a much higher overall affinity for both ligands and dampens the activation of T cells by outcompeting CD28 in binding CD80 and CD86, as well as actively delivering inhibitory signals to the T cell. CTLA4 also confers signaling-independent T cell inhibition through the sequestration of CD80 and CD86 from CD28 engagement, as well as active removal of CD80 and CD86 from the antigen-presenting cell (APC) surface.

In one embodiment, a DSB is introduced in one or more genes encoding a TCR signaling component (e.g., constant region of TCRα gene), an immune system checkpoint, or an immunosuppressive signaling component by an engineered nuclease in the presence of a donor repair template comprising one or more pairs of homology arms flanking a transgene encoding a CTLA-4 flip receptor that is inserted into the one or more genes at the DSB by homologous recombination.

CTLA-4 flip receptors contemplated in particular embodiments comprise the extracellular ligand binding domain of the human CTLA-4 receptor, a transmembrane domain from CTLA-4, a CD3 polypeptide, CD4, CD8α, CD28, CD134, or CD137, and an endodomain from CD28, CD134, CD137, CD278, and/or CD3ζ.

v. TIGIT Flip Receptor

T cell immunoglobulin and immunoreceptor tyrosine-based inhibitory motif [ITIM] domain (TIGIT) is a T cell coinhibitory receptor that was identified as consistently highly expressed across multiple solid tumor types. TIGIT limits antitumor and other CD8$^+$ T cell-dependent chronic immune responses. TIGIT is highly expressed on human and murine tumor-infiltrating T cells. Genetic ablation or antibody blockade of TIGIT has been shown to enhance NK cell killing and CD4$^+$ T cell priming in vitro and in vivo and can exacerbate the severity of CD4$^+$ T cell-dependent autoimmune diseases such as experimental autoimmune encephalitis (Goding et al., 2013, Joller et al., 2011, Levin et al., 2011, Lozano et al., 2012, Stanietsky et al., 2009, Stanietsky et al., 2013, Stengel et al., 2012, Yu et al., 2009). Conversely, administration of TIGIT-Fc fusion proteins or agonistic anti-TIGIT antibodies suppressed T cell activation in vitro and CD4$^+$ T cell-dependent delayed-type hypersensitivity in vivo (Yu et al., 2009). TIGIT likely exerts its immunosuppressive effects by outcompeting it countercostimulatory receptor CD226 for binding to CD155.

In models of both cancer and chronic viral infection, antibody coblockade of TIGIT and PD-L1 synergistically and specifically enhanced CD8$^+$ T cell effector function, resulting in significant tumor and viral clearance, respectively.

In one embodiment, a DSB is introduced in one or more genes encoding a TCR signaling component (e.g., constant region of TCRα gene), an immune system checkpoint, or an immunosuppressive signaling component by an engineered nuclease in the presence of a donor repair template comprising one or more pairs of homology arms flanking a transgene encoding a TIGIT flip receptor that is inserted into the one or more genes at the DSB by homologous recombination.

TIGIT flip receptors contemplated in particular embodiments comprise the extracellular ligand binding domain of the human TIGIT receptor, a transmembrane domain from TIGIT, a CD3 polypeptide, CD4, CD8α, CD28, CD134, or CD137, and an endodomain from CD28, CD134, CD137, CD278, and/or CD3ζ.

vi. TGFβRII Flip Receptor

Transforming growth factor-β (TGFβ) is an immunosuppressive cytokine produced by tumor cells and immune cells that can polarize many arms of the immune system. The overproduction of immunosuppressive cytokines, including TGFβ, by tumor cells and tumor-infiltrating lymphocytes contributes to an immunosuppressive tumor microenvironment. TGFβ is frequently associated with tumor metastasis and invasion, inhibiting the function of immune cells, and poor prognosis in patients with cancer. TGFβ signaling through TGFβRII in tumor-specific CTLs dampens their function and frequency in the tumor, and blocking TGFβ signaling on CD8$^+$ T cells with monoclonal antibodies results in more rapid tumor surveillance and the presence of many more CTLs at the tumor site.

In one embodiment, a DSB is introduced in one or more genes encoding a TCR signaling component (e.g., constant region of TCRα gene), an immune system checkpoint, or an immunosuppressive signaling component by an engineered nuclease in the presence of a donor repair template comprising one or more pairs of homology arms flanking a transgene encoding a TGFβRII flip receptor that is inserted into the one or more genes at the DSB by homologous recombination.

TGFβRII flip receptors contemplated in particular embodiments comprise the extracellular ligand binding domain of the human TGFβRII receptor, a transmembrane domain from TGFβRII, a CD3 polypeptide, CD4, CD8α, CD28, CD134, or CD137, and an endodomain from CD28, CD134, CD137, CD278, and/or CD3ζ.

2. Immunosuppressive Signal Dampers

One limitation or problem that vexes existing adoptive cell therapy is hyporesponsiveness of immune effector cells due to exhaustion mediated by the tumor microenvironment. Exhausted T cells have a unique molecular signature that is markedly distinct from naive, effector or memory T cells. They are defined as T cells with decreased cytokine expression and effector function.

In particular embodiments, genome edited immune effector cells contemplated herein are made more resistant to exhaustion by decreasing or damping signaling by immunosuppressive factors. In one embodiment, T cells are engineered by introducing a DSB into one or more genes encoding a TCR signaling component (e.g., constant region of TCRα gene), an immune system checkpoint, or an immunosuppressive signaling component in the presence of a donor repair template encoding an immunosuppressive signal damper.

In particular embodiments, a DNA donor template is designed to insert an immunosuppressive signal damper into one locus and one or more transgenes encoding an immunopotency enhancer, another immunosuppressive signal damper, or an engineered antigen receptor into one or more different loci.

As used herein, the term "immunosuppressive signal damper" refers to a non-naturally occurring polypeptide that decreases the transduction of immunosuppressive signals from the tumor microenvironment to a T cell. In one embodiment, the immunosuppressive signal damper is an antibody or antigen binding fragment thereof that binds an immunosuppressive factor. In preferred embodiments, an immunosuppressive signal damper refers to a polypeptide that elicits a suppressive, dampening, or dominant negative effect on a particular immunosuppressive factor or signaling pathway because the damper comprises and exodomain that binds an immunosuppressive factor, and optionally, a transmembrane domain, and optionally, a modified endodomain (e.g., intracellular signaling domain).

In particular embodiments, the exodomain is an extracellular binding domain that recognizes and binds an immunosuppressive factor.

In particular embodiments, the modified endodomain is mutated to decrease or inhibit immunosuppressive signals. Suitable mutation strategies include, but are not limited to amino acid substitution, addition, or deletion. Suitable mutations further include, but are not limited to endodomain truncation to remove signaling domains, mutating endodomains to remove residues important for signaling motif activity, and mutating endodomains to block receptor cycling. In particular embodiments, the endodomain, when present does not transduce immunosuppressive signals, or has substantially reduced signaling.

Thus, in some embodiments, an immunosuppressive signal damper acts as sink for one or more immunosuppressive factors from the tumor microenvironment and inhibits the corresponding immunosuppressive signaling pathways in the T cell.

One immunosuppressive signal is mediated by tryptophan catabolism. Tryptophan catabolism by indoleamine 2,3-dioxygenase (IDO) in cancer cells leads to the production of kynurenines which have been shown to have an immunosuppressive effect on T cells in the tumor microenvironment. See e.g., Platten et al. (2012) Cancer Res. 72(21):5435-40.

In one embodiment, a donor repair template comprises an enzyme with kynureninase activity.

Illustrative examples of enzymes having kynureninase activity suitable for use in particular embodiments include, but are not limited to, L-Kynurenine hydrolase.

In one embodiment, the donor repair template comprises one or more polynucleotides that encodes an immunosuppressive signal damper that decrease or block immunosuppressive signaling mediated by an immunosuppressive factor.

Illustrative examples of immunosuppressive factors targeted by the immunosuppressive signal dampers contemplated in particular embodiments include, but are not limited to: programmed death ligand 1 (PD-L1), programmed death ligand 2 (PD-L2), transforming growth factor 3 (TGFβ), macrophage colony-stimulating factor 1 (M-CSF1), tumor necrosis factor related apoptosis inducing ligand (TRAIL), receptor-binding cancer antigen expressed on SiSo cells ligand (RCAS1), Fas ligand (FasL), CD47, interleukin-4 (IL-4), interleukin-6 (IL-6), interleukin-8 (IL-8), interleukin-10 (IL-10), and interleukin-13 (IL-13).

In various embodiments, the immunosuppressive signal damper comprises an antibody or antigen binding fragment thereof that binds an immunosuppressive factor.

In various embodiments, the immunosuppressive signal damper comprises an exodomain that binds an immunosuppressive factor.

In particular embodiments, the immunosuppressive signal damper comprises an exodomain that binds an immunosuppressive factor and a transmembrane domain.

In another embodiment, the immunosuppressive signal damper comprises an exodomain that binds an immunosuppressive factor, a transmembrane domain, and a modified endodomain that does not transduce or that has substantially reduced ability to transduce immunosuppressive signals.

As used herein, the term "exodomain" refers to an antigen binding domain. In one embodiment, the exodomain is an extracellular ligand binding domain of an immunosuppressive receptor that transduces immunosuppressive signals from the tumor microenvironment to a T cell. In particular embodiments, an exodomain refers to an extracellular ligand binding domain of a receptor that comprises an immunoreceptor tyrosine inhibitory motif (ITIM) and/or an immunoreceptor tyrosine switch motif (ITSM).

Illustrative examples of exodomains suitable for use in particular embodiments of immunosuppressive signal dampers include, but are not limited to antibodies or antigen binding fragments thereof, or extracellular ligand binding domains isolated from the following polypeptides: programmed cell death protein 1 (PD-1), lymphocyte activation gene 3 protein (LAG-3), T cell immunoglobulin domain and mucin domain protein 3 (TIM-3), cytotoxic T lymphocyte antigen-4 (CTLA-4), band T lymphocyte attenuator (BTLA), T cell immunoglobulin and immunoreceptor tyrosine-based inhibitory motif domain (TIGIT), transforming growth factor 3 receptor II (TGFβRII), macrophage colony-stimulating factor 1 receptor (CSF1R), interleukin 4 receptor (IL4R), interleukin 6 receptor (IL6R), chemokine (C-X-C motif) receptor 1 (CXCR1), chemokine (C-X-C motif) receptor 2 (CXCR2), interleukin 10 receptor subunit alpha (IL10R), interleukin 13 receptor subunit alpha 2 (IL13Rα2), tumor necrosis factor related apoptosis inducing ligand (TRAILR1), receptor-binding cancer antigen expressed on SiSo cells (RCAS1R), and Fas cell surface death receptor (FAS).

In one embodiment, the exodomain comprises an extracellular ligand binding domain of a receptor selected from the group consisting of: PD-1, LAG-3, TIM-3, CTLA-4, IL10R, TIGIT, CSF1R, and TGFβRII.

A number of transmembrane domains may be used in particular embodiments. Illustrative examples of transmembrane domains suitable for use in particular embodiments of immunosuppressive signal dampers contemplated in particular embodiments include, but are not limited to transmembrane domains of the following proteins: alpha or beta chain of the T-cell receptor, CDδ, CD3ε, CDγ, CD3ζ, CD4, CD5, CD8α, CD9, CD 16, CD22, CD27, CD28, CD33, CD37, CD45, CD64, CD80, CD86, CD 134, CD137, CD152, CD154, and PD-1.

In particular embodiments, the adoptive cell therapies contemplated herein comprise an immunosuppressive signal damper that inhibits or blocks the transduction of immunosuppressive TGFβ signals from the tumor microenvironment through TGFβRII. In one embodiment, the immunosuppressive signal damper comprises an exodomain that comprises a TGFβRII extracellular ligand binding, a TGFβRII transmembrane domain, and a truncated, non-functional TGFβRII endodomain. In another embodiment, the immunosuppressive signal damper comprises an exodomain that comprises a TGFβRII extracellular ligand binding, a TGFβRII transmembrane domain, and lacks an endodomain.

In particular embodiments, a plurality of engineered nucleases are used to induce a DSB in multiple target sites in a genome, and a DNA donor repair template comprising a transgene encoding an immunosuppressive signal damper and flanked by a plurality of homology arms corresponding to a plurality of target sites in a genome is introduced into the cell and is inserted into at least one of the target sites by homologous recombination.

In particular embodiments, a plurality of engineered nucleases are used to induce a DSB in multiple target sites in a genome, and a DNA donor repair template comprising a transgene encoding an immunosuppressive signal damper and flanked by a plurality of homology arms corresponding to a plurality of target sites in a genome is introduced into the cell and is inserted into two or more of the target sites by homologous recombination.

In particular embodiments, a plurality of engineered nucleases are used to induce a DSB in multiple target sites in a genome, and a DNA donor repair template comprising a transgene encoding an immunosuppressive signal damper and flanked by a plurality of homology arms corresponding to a plurality of target sites in a genome is introduced into the cell and is inserted into each of the target sites by homologous recombination.

3. Engineered Antigen Receptors

In particular embodiments, the genome edited immune effector cells contemplated herein comprise an engineered antigen receptor. In one embodiment, T cells are engineered by introducing a DSB into one or more genes encoding a TCR signaling component (e.g., constant region of TCRα gene), an immune system checkpoint, or an immunosuppressive signaling component in the presence of a donor repair template encoding an engineered antigen receptor.

In particular embodiments, a DNA donor template is designed to insert an engineered antigen receptor into one locus and one or more transgenes encoding an immunopotency enhancer, an immunosuppressive signal damper, or another engineered antigen receptor into one or more different loci.

In particular embodiments, the engineered antigen receptor is an engineered T cell receptor (TCR), a chimeric antigen receptor (CAR), a DARIC receptor or components thereof, or a chimeric cytokine receptor receptor.

In particular embodiments, a plurality of engineered nucleases are used to induce a DSB in multiple target sites in a genome, and a DNA donor repair template comprising a transgene encoding an engineered antigen receptor and flanked by a plurality of homology arms corresponding to a plurality of target sites in a genome is introduced into the cell and is inserted into at least one of the target sites by homologous recombination.

In particular embodiments, a plurality of engineered nucleases are used to induce a DSB in multiple target sites in a genome, and a DNA donor repair template comprising a transgene encoding an engineered antigen receptor and flanked by a plurality of homology arms corresponding to a plurality of target sites in a genome is introduced into the cell and is inserted into two or more of the target sites by homologous recombination.

In particular embodiments, a plurality of engineered nucleases are used to induce a DSB in multiple target sites in a genome, and a DNA donor repair template comprising a transgene encoding an engineered antigen receptor and flanked by a plurality of homology arms corresponding to a plurality of target sites in a genome is introduced into the cell and is inserted into each of the target sites by homologous recombination.

a. Engineered TCRs

In particular embodiments, the genome edited immune effector cells contemplated herein comprise an engineered TCR. In one embodiment, T cells are engineered by introducing a DSB into one or more genes encoding a TCR signaling component (e.g., constant region of TCRα gene), an immune system checkpoint, or an immunosuppressive signaling component in the presence of a donor repair template encoding an engineered TCR.

In one embodiment, the engineered T cells contemplated herein comprise an engineered TCR that is inserted at a TCRα allele and one or more of an immunosuppressive signal damper, a flip receptor, a chimeric antigen receptor (CAR), a DARIC receptor or components thereof, or a chimeric cytokine receptor receptor is inserted into a DSB in one or more genes encoding another TCR signaling component, an immune system checkpoint, or an immunosuppressive signaling component.

Naturally occurring T cell receptors comprise two subunits, an alpha chain and a beta chain subunit, each of which is a unique protein produced by recombination event in each T cell's genome. Libraries of TCRs may be screened for their selectivity to particular target antigens. In this manner, natural TCRs, which have a high-avidity and reactivity toward target antigens may be selected, cloned, and subsequently introduced into a population of T cells used for adoptive immunotherapy.

In one embodiment, T cells are modified by introducing a donor repair template comprising a polynucleotide encoding a subunit of a TCR at a DSB in one or more TCRα alleles, wherein the TCR subunit has the ability to form TCRs that confer specificity to T cells for tumor cells expressing a target antigen. In particular embodiments, the subunits have one or more amino acid substitutions, deletions, insertions, or modifications compared to the naturally occurring subunit, so long as the subunits retain the ability to form TCRs and confer upon transfected T cells the ability to home to target cells, and participate in immunologically-relevant cytokine signaling. The engineered TCRs preferably also bind target cells displaying the relevant tumor-associated peptide with high avidity, and optionally mediate efficient killing of target cells presenting the relevant peptide in vivo.

The nucleic acids encoding engineered TCRs are preferably isolated from their natural context in a (naturally-occurring) chromosome of a T cell, and can be incorporated into suitable vectors as described elsewhere herein. Both the nucleic acids and the vectors comprising them can be transferred into a cell, preferably a T cell in particular embodiments. The modified T cells are then able to express one or more chains of a TCR encoded by the transduced nucleic acid or nucleic acids. In preferred embodiments, the engineered TCR is an exogenous TCR because it is introduced into T cells that do not normally express the particular TCR. The essential aspect of the engineered TCRs is that it has high avidity for a tumor antigen presented by a major histocompatibility complex (MHC) or similar immunological component. In contrast to engineered TCRs, CARs are engineered to bind target antigens in an MHC independent manner.

The TCR can be expressed with additional polypeptides attached to the amino-terminal or carboxyl-terminal portion of the inventive alpha chain or beta chain of a TCR so long as the attached additional polypeptide does not interfere with the ability of the alpha chain or beta chain to form a functional T cell receptor and the MHC dependent antigen recognition.

Antigens that are recognized by the engineered TCRs contemplated in particular embodiments include, but are not limited to cancer antigens, including antigens on both hematological cancers and solid tumors. Illustrative antigens include, but are not limited to FRα, TPBG, αvβ6 integrin, BCMA, B7-H3, B7-H6, CD276, CD16, CD19, CD20, CD22, CD30, CD33, CD44, CD44v6, CD44v7/8, CD70, CD79a, CD79b, CD123, CD138, CD171, CEA, CSPG4, EGFR, ERBB2, EGFRvIII, EPCAM, EphA2, FAP, fetal AchR, GD2, GD3, GPC3, HLA-A1+MAGEA1, HLA-A2+ MAGEA1, HLA-A3+MAGEA1, MAGEA1, HLA-A1+NY-ESO-1, HLA-A2+NY-ESO-1, HLA-A3+NY-ESO-1, IL-11Rα, IL-13Rα2, lambda light chain, lewis-Y, kappa light chain, mesothelin, MUC1, MUC16, NCAM, NKG2D ligands, NY-ESO-1, PRAME, PSCA, PSMA, ROR1, SSX, survivin, TAG72, TEM1, TEM5, TEM7, TEM8, VEGFR2, and WT-1.

In one embodiment, a donor repair template comprises a polynucleotide encoding an RNA polymerase II promoter or a first self-cleaving viral peptide and a polynucleotide encoding the alpha chain and/or the beta chain of the engineered TCR integrated into one modified and/or non-functional TCRα allele.

In one embodiment, a donor repair template comprises a polynucleotide encoding an RNA polymerase II promoter or a first self-cleaving viral peptide and a polynucleotide encoding the alpha chain and the beta chain of the engineered TCR integrated into one modified and/or non-functional TCRα allele.

In a particular embodiment, the donor repair template comprises from 5' to 3', a 5' homology arm homologous to a TCRα allele, a polynucleotide encoding a first self-cleaving viral peptide, a polynucleotide encoding the alpha chain of the engineered TCR, a polynucleotide encoding a second self-cleaving viral peptide, and a polynucleotide encoding the beta chain of the engineered TCR, and a 3' homology arm homologous to a TCRα allele. In such a case, the other TCRα allele may be functional or may have decreased function or been rendered non-functional by a DSB and repair by NHEJ. In one embodiment, the other TCRα allele has been modified by an engineered nuclease contemplated herein and may have decreased function or been rendered non-functional.

In a certain embodiment, both TCRα alleles are modified and have decreased function or are non-functional.

b. Chimeric Antigen Receptors (CARs)

In particular embodiments, the engineered immune effector cells contemplated herein comprise one or more chimeric antigen receptors (CARs) that redirect cytotoxicity toward tumor cells. CARs are molecules that combine antibody-based specificity for a target antigen (e.g., tumor antigen) with a T cell receptor-activating intracellular domain to generate a chimeric protein that exhibits a specific anti-tumor cellular immune activity. As used herein, the term, "chimeric," describes being composed of parts of different proteins or DNAs from different origins. In one embodiment, T cells are engineered by introducing a DSB into one or more genes encoding a TCR signaling component (e.g., constant region of TCRα gene), an immune system checkpoint, or an immunosuppressive signaling component in the presence of a donor repair template encoding a CAR.

In one embodiment, the engineered T cells contemplated herein comprise a CAR that is inserted at a TCRα allele and one or more of an immunosuppressive signal damper, a flip receptor, an alpha and/or beta chain of an engineered T cell receptor (TCR), a chimeric antigen receptor (CAR), a DARIC receptor or components thereof, or a chimeric cytokine receptor receptor is inserted into a DSB in one or more genes encoding a TCR signaling component, an immune system checkpoint, or an immunosuppressive signaling component.

In various embodiments, the genome edited T cells express one or more CARs in two of more genetic loci. The CARs may be identical or different. In one embodiment, the same CAR is inserted in various genomic locations by virtue of the DNA donor repair template comprising pairs of homology arms homologous to the various genomic locations flanking a transgene encoding a CAR.

In particular embodiments, a DNA donor template is designed to insert a CAR into one locus and one or more transgenes encoding an immunopotency enhancer, an immunosuppressive signal damper, or another engineered antigen receptor into one or more different loci.

In various embodiments, a CAR comprises an extracellular domain that binds to a specific target antigen (also referred to as a binding domain or antigen-specific binding domain), a transmembrane domain and an intracellular signaling domain. The main characteristic of CARs are their ability to redirect immune effector cell specificity, thereby triggering proliferation, cytokine production, phagocytosis or production of molecules that can mediate cell death of the target antigen expressing cell in a major histocompatibility (MHC) independent manner, exploiting the cell specific targeting abilities of monoclonal antibodies, soluble ligands or cell specific coreceptors.

In particular embodiments, CARs comprise an extracellular binding domain that specifically binds to a target polypeptide, e.g., target antigen, expressed on tumor cell. As used herein, the terms, "binding domain," "extracellular domain," "extracellular binding domain," "antigen binding domain," "antigen-specific binding domain," and "extracellular antigen specific binding domain," are used interchangeably and provide a chimeric receptor, e.g., a CAR or DARIC, with the ability to specifically bind to the target antigen of interest. A binding domain may comprise any protein, polypeptide, oligopeptide, or peptide that possesses the ability to specifically recognize and bind to a biological molecule (e.g., a cell surface receptor or tumor protein, lipid, polysaccharide, or other cell surface target molecule, or component thereof). A binding domain includes any naturally occurring, synthetic, semi-synthetic, or recombinantly produced binding partner for a biological molecule of interest.

In particular embodiments, the extracellular binding domain comprises an antibody or antigen binding fragment thereof.

An "antibody" refers to a binding agent that is a polypeptide comprising at least a light chain or heavy chain immunoglobulin variable region which specifically recognizes and binds an epitope of a target antigen, such as a peptide, lipid, polysaccharide, or nucleic acid containing an antigenic determinant, such as those recognized by an immune cell. Antibodies include antigen binding fragments, e.g., Camel Ig (a camelid antibody or VHH fragment thereof), Ig NAR, DARPins, FN3-fragments, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody) or other antibody fragments thereof. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, Ill.); Kuby, J., Immunology, 3rd Ed., W. H. Freeman & Co., New York, 1997.

In one preferred embodiment, the binding domain is an scFv.

In another preferred embodiment, the binding domain is a camelid antibody.

In particular embodiments, the CAR comprises an extracellular domain that binds an antigen selected from the group consisting of: FRα, TPBG, αvβ6 integrin, BCMA, B7-H3, B7-H6, CD276, CD16, CD19, CD20, CD22, CD30, CD33, CD44, CD44v6, CD44v7/8, CD70, CD79a, CD79b, CD123, CD138, CD171, CEA, CSPG4, EGFR, ERBB2, EGFRvIII, EPCAM, EphA2, FAP, fetal AchR, GD2, GD3, GPC3, HLA-A1+MAGEA1, HLA-A2+MAGEA1, HLA-A3+MAGEA1, MAGEA1, HLA-A1+NY-ESO-1, HLA-A2+NY-ESO-1, HLA-A3+NY-ESO-1, IL-11Rα, IL-13Rα2, lambda light chain, lewis-Y, kappa light chain, mesothelin, MUC1, MUC16, NCAM, NKG2D ligands, NY-ESO-1, PRAME, PSCA, PSMA, ROR1, SSX, survivin, TAG72, TEM1, TEM5, TEM7, TEM8, VEGFR2, and WT-1.

In particular embodiments, the CARs comprise an extracellular binding domain, e.g., antibody or antigen binding fragment thereof that binds an antigen, wherein the antigen is an MHC-peptide complex, such as a class I MHC-peptide complex or a class II MHC-peptide complex.

In certain embodiments, the CARs comprise linker residues between the various domains. A "variable region linking sequence," is an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. In particular embodiments, CARs comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

In particular embodiments, the binding domain of the CAR is followed by one or more "spacer domains," which refers to the region that moves the antigen binding domain away from the effector cell surface to enable proper cell/cell contact, antigen binding and activation (Patel et al., Gene Therapy, 1999; 6: 412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

In one embodiment, the spacer domain comprises the CH2 and CH3 of IgG1, IgG4, or IgD.

In one embodiment, the binding domain of the CAR is linked to one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region.

Illustrative hinge domains suitable for use in the CARs described herein include the hinge region derived from the extracellular regions of type 1 membrane proteins such as CD8α, and CD4, which may be wild-type hinge regions from these molecules or may be altered. In another embodiment, the hinge domain comprises a CD8a hinge region.

In one embodiment, the hinge is a PD-1 hinge or CD152 hinge.

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source.

Illustrative TM domains may be derived from (i.e., comprise at least the transmembrane region(s) of the alpha or beta chain of the T-cell receptor, CD3δ, CD3ε, CD3γ, CD3ζ, CD4, CD5, CD8α, CD9, CD 16, CD22, CD27, CD28, CD33, CD37, CD45, CD64, CD80, CD86, CD 134, CD137, CD152, CD154, and PD-1.

In one embodiment, a CAR comprises a TM domain derived from CD8α. In another embodiment, a CAR contemplated herein comprises a TM domain derived from CD8a and a short oligo- or polypeptide linker, preferably between 1, 2, 3, 4, 5, 6, 7, 8, 9, or 10 amino acids in length that links the TM domain and the intracellular signaling domain of the CAR. A glycine-serine linker provides a particularly suitable linker.

In particular embodiments, a CAR comprises an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain.

The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

It is known that signals generated through the TCR alone are insufficient for full activation of the T cell and that a secondary or costimulatory signal is also required. Thus, T cell activation can be said to be mediated by two distinct classes of intracellular signaling domains: primary signaling domains that initiate antigen-dependent primary activation through the TCR (e.g., a TCR/CD3 complex) and costimulatory signaling domains that act in an antigen-independent manner to provide a secondary or costimulatory signal. In preferred embodiments, a CAR comprises an intracellular signaling domain that comprises one or more "costimulatory signaling domains" and a "primary signaling domain."

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs.

Illustrative examples of ITAM containing primary signaling domains suitable for use in CARs contemplated in particular embodiments include those derived from FcRγ, FcRβ, CD3γ, CD3δ, CD3ε, CD3ζ, CD22, CD79a, CD79b, and CD66d. In particular preferred embodiments, a CAR comprises a CD3ζ primary signaling domain and one or more costimulatory signaling domains. The intracellular primary signaling and costimulatory signaling domains may be linked in any order in tandem to the carboxyl terminus of the transmembrane domain.

In particular embodiments, a CAR comprises one or more costimulatory signaling domains to enhance the efficacy and expansion of T cells expressing CAR receptors. As used herein, the term, "costimulatory signaling domain," or "costimulatory domain", refers to an intracellular signaling domain of a costimulatory molecule.

Illustrative examples of such costimulatory molecules suitable for use in CARs contemplated in particular embodiments include TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In one embodiment, a CAR comprises one or more costimulatory signaling domains selected from the group consisting of CD28, CD137, and CD134, and a CD3ζ primary signaling domain.

In various embodiments, the CAR comprises: an extracellular domain that binds an antigen selected from the group consisting of: BCMA, CD19, CSPG4, PSCA, ROR1, and TAG72; a transmembrane domain isolated from a polypeptide selected from the group consisting of CD4, CD8α, CD154, and PD-1; one or more intracellular costimulatory signaling domains isolated from a polypeptide selected from the group consisting of: CD28, CD134, and CD137; and a signaling domain isolated from a polypeptide selected from the group consisting of: FcRγ, FcRβ, CD3γ, CD3δ, CD3ε, CD3ζ, CD22, CD79a, CD79b, and CD66d.

c. DARIC Receptors

In particular embodiments, the engineered immune effector cells comprise one or more DARIC receptors. As used herein, the terms "DARIC" or "DARIC receptor" refer to a multichain engineered antigen receptor. In one embodiment, T cells are engineered by introducing a DSB into one or more genes encoding a TCR signaling component (e.g., constant region of TCRα gene), an immune system checkpoint, or an immunosuppressive signaling component in the presence of a donor repair template encoding one or more components of a DARIC.

In one embodiment, the engineered T cells comprise a DARIC that is not inserted at a TCRα allele and one or more of an immunosuppressive signal damper, a flip receptor, an alpha and/or beta chain of an engineered T cell receptor (TCR), a chimeric antigen receptor (CAR), or a DARIC receptor or components thereof is inserted into a DSB in one or more TCRα alleles.

In particular embodiments, a DNA donor template is designed to insert a DARIC into one locus and one or more transgenes encoding an immunopotency enhancer, an immunosuppressive signal damper, or another engineered antigen receptor into one or more different loci.

Illustrative examples of DARIC architectures and components are disclosed in PCT Publication No. WO2015/017214 and U.S. Patent Publication No. 20150266973, each of which is incorporated here by reference in its entirety.

In one embodiment, a donor repair template comprises the following DARIC components: a signaling polypeptide comprising a first multimerization domain, a first transmembrane domain, and one or more intracellular co-stimulatory signaling domains and/or primary signaling domains; and a binding polypeptide comprising a binding domain, a second multimerization domain, and optionally a second transmembrane domain. A functional DARIC comprises abridging factor that promotes the formation of a DARIC receptor complex on the cell surface with the bridging factor associated with and disposed between the multimerization domains of the signaling polypeptide and the binding polypeptide.

In particular embodiments, the first and second multimerization domains associate with a bridging factor selected from the group consisting of: rapamycin or a rapalog thereof, coumermycin or a derivative thereof, gibberellin or a derivative thereof, abscisic acid (ABA) or a derivative thereof, methotrexate or a derivative thereof, cyclosporin A or a derivative thereof, FKCsA or a derivative thereof, trimethoprim (Tmp)-synthetic ligand for FKBP (SLF) or a derivative thereof, and any combination thereof.

Illustrative examples of rapamycin analogs (rapalogs) include those disclosed in U.S. Pat. No. 6,649,595, which rapalog structures are incorporated herein by reference in their entirety. In certain embodiments, a bridging factor is a rapalog with substantially reduced immunosuppressive effect as compared to rapamycin. A "substantially reduced immunosuppressive effect" refers to a rapalog having at least less than 0.1 to 0.005 times the immunosuppressive effect observed or expected for an equimolar amount of rapamycin, as measured either clinically or in an appropriate in vitro (e.g., inhibition of T cell proliferation) or in vivo surrogate of human immunosuppressive activity. In one embodiment, "substantially reduced immunosuppressive effect" refers to a rapalog having an $EC_{50}$ value in such an in vitro assay that is at least 10 to 250 times larger than the $EC_{50}$ value observed for rapamycin in the same assay.

Other illustrative examples of rapalogs include, but are not limited to everolimus, novolimus, pimecrolimus, ridaforolimus, tacrolimus, temsirolimus, umirolimus, and zotarolimus.

In certain embodiments, multimerization domains will associate with a bridging factor being a rapamycin or rapalog thereof. For example, the first and second multimerization domains are a pair selected from FKBP and FRB. FRB domains are polypeptide regions (protein "domains") that are capable of forming a tripartite complex with an FKBP protein and rapamycin or rapalog thereof. FRB domains are present in a number of naturally occurring proteins, including mTOR proteins (also referred to in the literature as FRAP, RAPT1, or RAFT) from human and other species; yeast proteins including Tor1 and Tor2; and a Candida FRAP homolog. Information concerning the nucleotide sequences, cloning, and other aspects of these proteins is already known in the art. For example, a protein sequence accession number for a human mTOR is GenBank Accession No. L34075.1 (Brown et al., Nature 369:756, 1994).

FRB domains suitable for use in particular embodiments contemplated herein generally contain at least about 85 to about 100 amino acid residues. In certain embodiments, an FRB amino acid sequence for use in fusion proteins of this disclosure will comprise a 93 amino acid sequence Ile-2021 through Lys-2113 and a mutation of T2098L, based the amino acid sequence of GenBank Accession No. L34075.1. An FRB domain for use in DARICs contemplated in particular embodiments will be capable of binding to a complex of an FKBP protein bound to rapamycin or a rapalog thereof. In certain embodiments, a peptide sequence of an FRB domain comprises (a) a naturally occurring peptide sequence spanning at least the indicated 93 amino acid region of human mTOR or corresponding regions of homologous proteins; (b) a variant of a naturally occurring FRB in which up to about ten amino acids, or about 1 to about 5 amino acids or about 1 to about 3 amino acids, or in some embodiments just one amino acid, of the naturally-occurring peptide have been deleted, inserted, or substituted; or (c) a peptide encoded by a nucleic acid molecule capable of selectively hybridizing to a DNA molecule encoding a naturally occurring FRB domain or by a DNA sequence which would be capable, but for the degeneracy of the genetic code, of selectively hybridizing to a DNA molecule encoding a naturally occurring FRB domain.

FKBPs (FK506 binding proteins) are the cytosolic receptors for macrolides, such as FK506, FK520 and rapamycin, and are highly conserved across species lines. FKBPs are proteins or protein domains that are capable of binding to rapamycin or to a rapalog thereof and further forming a tripartite complex with an FRB-containing protein or fusion protein. An FKBP domain may also be referred to as a "rapamycin binding domain." Information concerning the nucleotide sequences, cloning, and other aspects of various FKBP species is known in the art (see, e.g., Staendart et al., Nature 346:671, 1990 (human FKBP12); Kay, Biochem. J. 314:361, 1996). Homologous FKBP proteins in other mammalian species, in yeast, and in other organisms are also known in the art and may be used in the fusion proteins disclosed herein. An FKBP domain contemplated in particular embodiments will be capable of binding to rapamycin or a rapalog thereof and participating in a tripartite complex with an FRB-containing protein (as may be determined by any means, direct or indirect, for detecting such binding).

Illustrative examples of FKBP domains suitable for use in a DARIC contemplated in particular embodiments include, but are not limited to: a naturally occurring FKBP peptide sequence, preferably isolated from the human FKBP12 protein (GenBank Accession No. AAA58476.1) or a peptide sequence isolated therefrom, from another human FKBP, from a murine or other mammalian FKBP, or from some other animal, yeast or fungal FKBP; a variant of a naturally occurring FKBP sequence in which up to about ten amino acids, or about 1 to about 5 amino acids or about 1 to about 3 amino acids, or in some embodiments just one amino acid, of the naturally-occurring peptide have been deleted, inserted, or substituted; or a peptide sequence encoded by a nucleic acid molecule capable of selectively hybridizing to a DNA molecule encoding a naturally occurring FKBP or by a DNA sequence which would be capable, but for the degeneracy of the genetic code, of selectively hybridizing to a DNA molecule encoding a naturally occurring FKBP.

Other illustrative examples of multimerization domain pairs suitable for use in a DARIC contemplated in particular embodiments include, but are not limited to include from FKBP and FRB, FKBP and calcineurin, FKBP and cyclophilin, FKBP and bacterial DHFR, calcineurin and cyclophilin, PYL1 and ABI1, or GIB1 and GAI, or variants thereof.

In yet other embodiments, an anti-bridging factor blocks the association of a signaling polypeptide and a binding polypeptide with the bridging factor. For example, cyclosporin or FK506 could be used as anti-bridging factors to titrate out rapamycin and, therefore, stop signaling since only one multimerization domain is bound. In certain embodiments, an anti-bridging factor (e.g., cyclosporine, FK506) is an immunosuppressive agent. For example, an immunosuppressive anti-bridging factor may be used to block or minimize the function of the DARIC components contemplated in particular embodiments and at the same time inhibit or block an unwanted or pathological inflammatory response in a clinical setting.

In one embodiment, the first multimerization domain comprises FRB T2098L, the second multimerization domain comprises FKBP12, and the bridging factor is rapalog AP21967.

In another embodiment, the first multimerization domain comprises FRB, the second multimerization domain comprises FKBP12, and the bridging factor is Rapamycin, temsirolimus or everolimus.

In particular embodiments, a signaling polypeptide a first transmembrane domain and a binding polypeptide comprises a second transmembrane domain or GPI anchor. Illustrative examples of the first and second transmembrane domains are isolated from a polypeptide independently selected from the group consisting of: CD3δ, CD3ε, CD3γ, CD3ζ, CD4, CD5, CD8α, CD9, CD 16, CD22, CD27, CD28, CD33, CD37, CD45, CD64, CD80, CD86, CD 134, CD137, CD152, CD154, and PD-1.

In one embodiment, a signaling polypeptide comprises one or more intracellular co-stimulatory signaling domains and/or primary signaling domains.

Illustrative examples of primary signaling domains suitable for use in DARIC signaling components contemplated in particular embodiments include those derived from FcRγ, FcRβ, CD3γ, CD3δ, CD3ε, CD3ζ, CD22, CD79a, CD79b, and CD66d. In particular preferred embodiments, a DARIC signaling component comprises a CD3ζ primary signaling domain and one or more costimulatory signaling domains. The intracellular primary signaling and costimulatory signaling domains may be linked in any order in tandem to the carboxyl terminus of the transmembrane domain.

Illustrative examples of such costimulatory molecules suitable for use in DARIC signaling components contemplated in particular embodiments include TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70. In one embodiment, a DARIC signaling component comprises one or more costimulatory signaling domains selected from the group consisting of CD28, CD137, and CD134, and a CD3ζ primary signaling domain.

In particular embodiments, a DARIC binding component comprises a binding domain. In one embodiment, the binding domain is an antibody or antigen binding fragment thereof.

The antibody or antigen binding fragment thereof comprises at least a light chain or heavy chain immunoglobulin variable region which specifically recognizes and binds an epitope of a target antigen, such as a peptide, lipid, polysaccharide, or nucleic acid containing an antigenic determinant, such as those recognized by an immune cell. Antibodies include antigen binding fragments, e.g., Camel Ig (a camelid antibody or VHH fragment thereof), Ig NAR, DARPins, FN3-fragments, Fab fragments, Fab' fragments, F(ab)'2 fragments, F(ab)'3 fragments, Fv, single chain Fv antibody ("scFv"), bis-scFv, (scFv)2, minibody, diabody, triabody, tetrabody, disulfide stabilized Fv protein ("dsFv"), and single-domain antibody (sdAb, Nanobody) or other antibody fragments thereof. The term also includes genetically engineered forms such as chimeric antibodies (for example, humanized murine antibodies), heteroconjugate antibodies (such as, bispecific antibodies) and antigen binding fragments thereof. See also, Pierce Catalog and Handbook, 1994-1995 (Pierce Chemical Co., Rockford, Ill.); Kuby, J., Immunology, 3rd Ed., W. H. Freeman & Co., New York, 1997.

In one preferred embodiment, the binding domain is an scFv.

In another preferred embodiment, the binding domain is a camelid antibody.

In particular embodiments, the DARIC binding component comprises an extracellular domain that binds an antigen selected from the group consisting of: FRα, TPBG, αvβ6 integrin, BCMA, B7-H3, B7-H6, CD276, CD16, CD19, CD20, CD22, CD30, CD33, CD44, CD44v6, CD44v7/8, CD70, CD79a, CD79b, CD123, CD138, CD171, CEA, CSPG4, EGFR, ERBB2, EGFRvIII, EPCAM, EphA2, FAP, fetal AchR, GD2, GD3, GPC3, HLA-A1$^+$MAGEA1, HLA-A2$^+$MAGEA1, HLA-A3$^+$MAGEA1, MAGEA1, HLA-A1$^+$NY-ESO-1, HLA-A2$^+$NY-ESO-1, HLA-A3$^+$NY-ESO-1, IL-11Rα, IL-13Rα2, lambda light chain, lewis-Y, kappa light chain, mesothelin, MUC1, MUC16, NCAM, NKG2D ligands, NY-ESO-1, PRAME, PSCA, PSMA, ROR1, SSX, survivin, TAG72, TEM1, TEM5, TEM7, TEM8, VEGFR2, and WT-1.

In one embodiment, the DARIC binding component comprises an extracellular domain, e.g., antibody or antigen binding fragment thereof that binds an MHC-peptide complex, such as a class I MHC-peptide complex or class II MHC-peptide complex.

In particular embodiments, the DARIC components contemplated herein comprise a linker or spacer that connects two proteins, polypeptides, peptides, domains, regions, or motifs. In certain embodiments, a linker comprises about two to about 35 amino acids, or about four to about 20 amino acids or about eight to about 15 amino acids or about 15 to about 25 amino acids. In other embodiments, a spacer may have a particular structure, such as an antibody CH2CH3 domain, hinge domain or the like. In one embodiment, a spacer comprises the CH2 and CH3 domains of IgG1, IgG4, or IgD.

In particular embodiments, the DARIC components contemplated herein comprise one or more "hinge domains," which plays a role in positioning the domains to enable proper cell/cell contact, antigen binding and activation. A DARIC may comprise one or more hinge domains between the binding domain and the multimerization domain and/or the transmembrane domain (TM) or between the multimerization domain and the transmembrane domain. The hinge domain may be derived either from a natural, synthetic, semi-synthetic, or recombinant source. The hinge domain can include the amino acid sequence of a naturally occurring immunoglobulin hinge region or an altered immunoglobulin hinge region. In particular embodiment, the hinge is a CD8a hinge or a CD4 hinge.

In one embodiment, a DARIC comprises a signaling polypeptide comprises a first multimerization domain of FRB T2098L, a CD8 transmembrane domain, a 4-1BB costimulatory domain, and a CD3ζ primary signaling domain; the binding polypeptide comprises an scFv that binds CD19, a second multimerization domain of FKBP12 and a CD4 transmembrane domain; and the bridging factor is rapalog AP21967.

In one embodiment, a DARIC comprises a signaling polypeptide comprises a first multimerization domain of FRB, a CD8 transmembrane domain, a 4-1BB costimulatory domain, and a CD3ζ primary signaling domain; the binding polypeptide comprises an scFv that binds CD19, a second multimerization domain of FKBP12 and a CD4 transmembrane domain; and the bridging factor is Rapamycin, temsirolimus or everolimus.

d. Zetakines

In particular embodiments, the engineered immune effector cells contemplated herein comprise one or more chimeric cytokine receptors. In one embodiment, T cells are engineered by introducing a DSB into one or more genes encoding a TCR signaling component (e.g., constant region of TCRα gene), an immune system checkpoint, or an immunosuppressive signaling component in the presence of a donor repair template encoding a zetakine.

In one embodiment, the engineered T cells contemplated herein a chimeric cytokine receptor that is not inserted at a TCRα allele and one or more of an immunosuppressive signal damper, a flip receptor, an alpha and/or beta chain of an engineered T cell receptor (TCR), a chimeric antigen receptor (CAR), a DARIC receptor or components thereof, or a chimeric cytokine receptor receptor is inserted into a DSB in one or more TCRα alleles.

In particular embodiments, a DNA donor template is designed to insert a zetakine into one locus and one or more transgenes encoding an immunopotency enhancer, an immunosuppressive signal damper, or another engineered antigen receptor into one or more different loci.

In various embodiments, the genome edited T cell s express chimeric cytokine receptor that redirect cytotoxicity toward tumor cells. Zetakines are chimeric transmembrane immunoreceptors that comprise an extracellular domain comprising a soluble receptor ligand linked to a support region capable of tethering the extracellular domain to a cell surface, a transmembrane region and an intracellular signaling domain. Zetakines, when expressed on the surface of T lymphocytes, direct T cell activity to those cells expressing a receptor for which the soluble receptor ligand is specific. Zetakine chimeric immunoreceptors redirect the antigen specificity of T cells, with application to treatment of a variety of cancers, particularly via the autocrine/paracrine cytokine systems utilized by human malignancy.

In particular embodiments, the chimeric cytokine receptor comprises an immunosuppressive cytokine or cytokine receptor binding variant thereof, a linker, a transmembrane domain, and an intracellular signaling domain.

In particular embodiments, the cytokine or cytokine receptor binding variant thereof is selected from the group consisting of: interleukin-4 (IL-4), interleukin-6 (IL-6), interleukin-8 (IL-8), interleukin-10 (IL-10), and interleukin-13 (IL-13).

In certain embodiments, the linker comprises a CH2CH3 domain, hinge domain, or the like. In one embodiment, a linker comprises the CH2 and CH3 domains of IgG1, IgG4, or IgD. In one embodiment, a linker comprises a CD8α or CD4 hinge domain.

In particular embodiments, the transmembrane domain is selected from the group consisting of: the alpha or beta chain of the T-cell receptor, CD3δ, CD3ε, CD3γ, CD3ζ, CD4, CD5, CD8α, CD9, CD 16, CD22, CD27, CD28, CD33, CD37, CD45, CD64, CD80, CD86, CD 134, CD137, CD152, CD154, and PD-1.

In particular embodiments, the intracellular signaling domain is selected from the group consisting of: an ITAM containing primary signaling domain and/or a costimulatory domain.

In particular embodiments, the intracellular signaling domain is selected from the group consisting of: FcRγ, FcRβ, CD3γ, CD3δ, CD3ε, CD3ζ, CD22, CD79a, CD79b, and CD66d.

In particular embodiments, the intracellular signaling domain is selected from the group consisting of TLR1, TLR2, TLR3, TLR4, TLR5, TLR6, TLR7, TLR8, TLR9, TLR10, CARD11, CD2, CD7, CD27, CD28, CD30, CD40, CD54 (ICAM), CD83, CD134 (OX40), CD137 (4-1BB), CD278 (ICOS), DAP10, LAT, NKD2C, SLP76, TRIM, and ZAP70.

In one embodiment, a chimeric cytokine receptor comprises one or more costimulatory signaling domains selected from the group consisting of CD28, CD137, and CD134, and a CD3ζ primary signaling domain.

4. Globin Genes

In particular embodiments, the genome edited hematopoietic cells contemplated herein comprise a globin gene or anti-sickling variant thereof. In one embodiment, hematopoietic cells are engineered by introducing a DSB into one or more genes encoding a gene that contributes to repression of γ-globin gene expression and HbF, including, but not limited to the BCL11A locus, the KLF1 locus, the SOX6 locus, the GATA1 locus, and the LSD1 locus; a thalassemic allele of a β-globin locus, or a sickling allele of a β-globin locus in the presence of a donor repair template encoding a globin gene or anti-sickling variant thereof.

In particular embodiments, the globin or anti-sickling variant thereof includes, but is not limited to is β-globin, δ-globin, γ-globin, β-globin$^{A-T87Q}$, β-globin$^{A-T87Q/K120E/K95E}$, or β-globin$^{A-T87Q/G16D/E22A}$.

In particular embodiments, a plurality of engineered nucleases are used to induce a DSB in multiple target sites in a genome, and a DNA donor repair template comprising a transgene encoding a globin or anti-sickling variant thereof and flanked by a plurality of homology arms corresponding to a plurality of target sites in a genome is introduced into the cell and is inserted into at least one of the target sites by homologous recombination.

In particular embodiments, a plurality of engineered nucleases are used to induce a DSB in multiple target sites in a genome, and a DNA donor repair template comprising a transgene encoding a globin or anti-sickling variant thereof and flanked by a plurality of homology arms corresponding to a plurality of target sites in a genome is introduced into the cell and is inserted into two or more of the target sites by homologous recombination.

D. Nucleases

Immune effector cell compositions contemplated in particular embodiments are generated by multiplex genome editing accomplished with engineered nucleases targeting a plurality of loci. In particular embodiments, engineered nucleases are introduced into an immune effector cell to induce a DSB in a plurality of genome target sites including, but not limited to genes encoding a TCR signaling component (e.g., constant region of TCRα gene), an immune system checkpoint, or an immunosuppressive signaling component.

Illustrative examples of immune system checkpoint genes include, but are not limited to: PD-1, LAG-3, TIM-3, CTLA-4, BTLA, TIGIT, VISTA, and KIRs.

Illustrative examples of genes encoding immunosuppressive signaling components include, but are not limited to: IL-10Rα, TGFβR1, TGFβR2, AHR, SGK1, TSC2, VHL, A2AR, and CBLB.

Hematopoeitic cell compositions contemplated in particular embodiments are generated by multiplex genome editing accomplished with engineered nucleases targeting a plurality of loci. In particular embodiments, engineered nucleases are introduced into a hematopoietic cell to induce a DSB in a plurality of genome target sites including, but not limited to genes encoding a polypeptide that contributes to repression of γ-globin gene expression and HbF.

Illustrative examples of polypeptides that repress γ-globin gene expression and HbF include, but are not limited to: BCL11A, KLF1, SOX6, GATA1, and LSD1.

The engineered nucleases contemplated in particular embodiments generate single-stranded DNA nicks or double-stranded DNA breaks (DSB) in a target sequence. Furthermore, a DSB can be achieved in the target DNA by the use of two nucleases generating single-stranded micks (nickases). Each nickase cleaves one strand of the DNA and the use of two or more nickases can create a double strand break (e.g., a staggered double-stranded break) in a target DNA sequence. In preferred embodiments, the nucleases are used in combination with a donor repair template, which is introduced into the target sequence at the DNA break-site via homologous recombination at a DSB.

Engineered nucleases contemplated in particular embodiments herein that are suitable for genome editing comprise one or more DNA binding domains and one or more DNA cleavage domains (e.g., one or more endonuclease and/or exonuclease domains), and optionally, one or more linkers contemplated herein. An "engineered nuclease" refers to a nuclease comprising one or more DNA binding domains and one or more DNA cleavage domains, wherein the nuclease has been designed and/or modified to bind a DNA binding target sequence adjacent to a DNA cleavage target sequence. The engineered nuclease may be designed and/or modified from a naturally occurring nuclease or from a previously engineered nuclease. Engineered nucleases contemplated in particular embodiments may further comprise one or more additional functional domains, e.g., an end-processing enzymatic domain of an end-processing enzyme that exhibits 5-3' exonuclease, 5-3' alkaline exonuclease, 3-5' exonuclease (e.g., Trex2), 5' flap endonuclease, helicase or template-independent DNA polymerases activity.

Illustrative examples of nucleases that may be engineered to bind and cleave a target sequence include, but are not limited to homing endonucleases (meganucleases), mega-TALs, transcription activator-like effector nucleases (TAL-ENs), zinc finger nucleases (ZFNs), and clustered regularly-interspaced short palindromic repeats (CRISPR)/Cas nuclease systems.

In particular embodiments, the nucleases contemplated herein comprise one or more heterologous DNA-binding and cleavage domains (e.g., ZFNs, TALENs, megaTALs), (Boissel et al., 2014; Christian et al., 2010). In other embodiments, the DNA-binding domain of a naturally-occurring nuclease may be altered to bind to a selected target site (e.g., a meganuclease that has been engineered to bind to site different than the cognate binding site). For example, meganucleases have been designed to bind target sites different from their cognate binding sites (Boissel et al., 2014). In particular embodiments, a nuclease requires a nucleic acid sequence to target the nuclease to a target site (e.g., CRISPR/Cas).

1. Homing Endonucleases/Meganucleases

In various embodiments, a plurality of homing endonucleases or meganucleases are introduced into a cell and engineered to bind to, and to introduce single-stranded nicks or double-strand breaks (DSBs) in a plurality of genome target sites including, but not limited to genes encoding a TCR signaling component (e.g., constant region of TCRα gene), an immune system checkpoint, or an immunosuppressive signaling component. "Homing endonuclease" and "meganuclease" are used interchangeably and refer to naturally-occurring nucleases or engineered meganucleases that recognize 12-45 base-pair cleavage sites and are commonly grouped into five families based on sequence and structure motifs: LAGLIDADG (SEQ ID NO: 40), GIY-YIG, HNH, His-Cys box, and PD-(D/E)XK.

Engineered HEs do not exist in nature and can be obtained by recombinant DNA technology or by random mutagenesis. Engineered HEs may be obtained by making one or more amino acid alterations, e.g., mutating, substituting, adding, or deleting one or more amino acids, in a naturally occurring HE or previously engineered HE. In particular embodiments, an engineered HE comprises one or more amino acid alterations to the DNA recognition interface.

Engineered HEs contemplated in particular embodiments may further comprise one or more linkers and/or additional functional domains, e.g., an end-processing enzymatic domain of an end-processing enzyme that exhibits 5-3' exonuclease, 5-3' alkaline exonuclease, 3-5' exonuclease (e.g., Trex2), 5' flap endonuclease, helicase or template-independent DNA polymerases activity. In particular embodiments, engineered HEs are introduced into a T cell with an end-processing enzyme that exhibits 5-3' exonuclease, 5-3' alkaline exonuclease, 3-5' exonuclease (e.g., Trex2), 5' flap endonuclease, helicase or template-independent DNA polymerases activity. The HE and 3' processing enzyme may be introduced separately, e.g., in different vectors or separate mRNAs, or together, e.g., as a fusion protein, or in a polycistronic construct separated by a viral self-cleaving peptide or an IRES element.

A "DNA recognition interface" refers to the HE amino acid residues that interact with nucleic acid target bases as well as those residues that are adjacent. For each HE, the DNA recognition interface comprises an extensive network of side chain-to-side chain and side chain-to-DNA contacts, most of which is necessarily unique to recognize a particular nucleic acid target sequence. Thus, the amino acid sequence of the DNA recognition interface corresponding to a particular nucleic acid sequence varies significantly and is a feature of any natural or engineered HE. By way of non-limiting example, an engineered HE contemplated in particular embodiments may be derived by constructing libraries of HE variants in which one or more amino acid residues localized in the DNA recognition interface of the natural HE (or a previously engineered HE) are varied. The libraries may be screened for target cleavage activity against each predicted TCRα locus target sites using cleavage assays (see e.g., Jarjour et al., 2009. *Nuc. Acids Res.* 37(20): 6871-6880).

LAGLIDADG (SEQ ID NO: 40) homing endonucleases (LHE) are the most well studied family of meganucleases, are primarily encoded in archaea and in organellar DNA in green algae and fungi, and display the highest overall DNA recognition specificity. LHEs comprise one or two LAGLIDADG (SEQ ID NO: 40) catalytic motifs per protein chain and function as homodimers or single chain monomers, respectively. Structural studies of LAGLIDADG (SEQ ID NO: 40) proteins identified a highly conserved core structure (Stoddard 2005), characterized by an αββαββα fold, with the LAGLIDADG (SEQ ID NO: 40) motif belonging to the first helix of this fold. The highly efficient and specific cleavage of LHE's represent a protein scaffold to derive novel, highly specific endonucleases. However, engineering LHEs to bind and cleave a non-natural or non-canonical target site requires selection of the appropriate LHE scaffold, examination of the target locus, selection of putative target sites, and extensive alteration of the LHE to alter its DNA contact points and cleavage specificity, at up to two-thirds of the base-pair positions in a target site.

Illustrative examples of LHEs from which engineered LHEs may be designed include, but are not limited to I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I.

Other illustrative examples of LHEs from which engineered LHEs may be designed include, but are not limited to I-CreI and I-SceI.

In one embodiment, the engineered LHE is selected from the group consisting of: I-CpaMI, I-HjeMI, I-OnuI, I-PanMI, and SmaMI.

In one embodiment, the engineered LHE is I-OnuI.

In one embodiment, engineered I-OnuI LHEs targeting the human TCRα gene were generated from a natural I-OnuI. In a preferred embodiment, engineered I-OnuI LHEs targeting the human TCRα gene were generated from a previously engineered I-OnuI.

In a particular embodiment, the engineered I-OnuI LHE comprises one or more amino acid substitutions in the DNA recognition interface. In particular embodiments, the I-OnuI LHE comprises at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the DNA recognition interface of I-OnuI (Taekuchi et al. 2011. *Proc Natl Acad Sci U.S.A* 2011 Aug. 9; 108(32): 13077-13082) or an engineered variant of I-OnuI.

In one embodiment, the I-OnuI LHE comprises at least 70%, more preferably at least 80%, more preferably at least 85%, more preferably at least 90%, more preferably at least 95%, more preferably at least 97%, more preferably at least 99% sequence identity with the DNA recognition interface of I-OnuI (Taekuchi et al. 2011. *Proc Natl Acad Sci U.S.A* 2011 Aug. 9; 108(32): 13077-13082) or an engineered variant of I-OnuI.

In a particular embodiment, an engineered I-OnuI LHE comprises one or more amino acid substitutions or modifications in the DNA recognition interface, particularly in the subdomains situated from positions 24-50, 68 to 82, 180 to 203 and 223 to 240 of I-OnuI.

In one embodiment, an engineered I-OnuI LHE comprises one or more amino acid substitutions or modifications at additional positions situated anywhere within the entire I-OnuI sequence. The residues which may be substituted and/or modified include but are not limited to amino acids that contact the nucleic acid target or that interact with the nucleic acid backbone or with the nucleotide bases, directly or via a water molecule. In one non-limiting example an engineered I-OnuI LHE contemplated herein comprises one or more substitutions and/or modifications, preferably at least 5, preferably at least 10, preferably at least 15, more preferably at least 20, even more preferably at least 25 in at least one position selected from the position group consisting of positions: 19, 24, 26, 28, 30, 32, 34, 35, 36, 37, 38, 40, 42, 44, 46, 48, 68, 70, 72, 75, 76 77, 78, 80, 82, 168, 180, 182, 184, 186, 188, 189, 190, 191, 192, 193, 195, 197, 199, 201, 203, 223, 225, 227, 229, 231, 232, 234, 236, 238, 240 of I-OnuI.

2. MegaTALs

In various embodiments, a plurality of megaTALs are introduced into a cell and engineered to bind and introduce DSBs in a plurality of genome target sites including, but not limited to genes encoding a polypeptide that suppresses γ-globin gene expression, a TCR signaling component (e.g., constant region of TCRα gene), an immune system checkpoint, or an immunosuppressive signaling component. A "megaTAL" refers to an engineered nuclease comprising an engineered TALE DNA binding domain and an engineered meganuclease, and optionally comprise one or more linkers and/or additional functional domains, e.g., an end-processing enzymatic domain of an end-processing enzyme that exhibits 5-3' exonuclease, 5-3' alkaline exonuclease, 3-5' exonuclease (e.g., Trex2), 5' flap endonuclease, helicase or template-independent DNA polymerases activity. In particular embodiments, a megaTAL can be introduced into a T cell with an end-processing enzyme that exhibits 5-3' exonuclease, 5-3' alkaline exonuclease, 3-5' exonuclease (e.g., Trex2), 5' flap endonuclease, helicase or template-independent DNA polymerases activity. The megaTAL and 3' processing enzyme may be introduced separately, e.g., in different vectors or separate mRNAs, or together, e.g., as a fusion protein, or in a polycistronic construct separated by a viral self-cleaving peptide or an IRES element.

A "TALE DNA binding domain" is the DNA binding portion of transcription activator-like effectors (TALE or TAL-effectors), which mimics plant transcriptional activators to manipulate the plant transcriptome (see e.g., Kay et al., 2007. *Science* 318:648-651). TALE DNA binding domains contemplated in particular embodiments are engineered de novo or from naturally occurring TALEs, e.g., AvrBs3 from *Xanthomonas campestris* pv. *vesicatoria*, *Xanthomonas gardneri*, *Xanthomonas translucens*, *Xanthomonas axonopodis*, *Xanthomonas perforans*, *Xanthomonas alfalfa*, *Xanthomonas citri*, *Xanthomonas euvesicatoria*, and *Xanthomonas oryzae* and brg11 and hpx17 from *Ralstonia solanacearum*. Illustrative examples of TALE proteins for deriving and designing DNA binding domains are disclosed in U.S. Pat. No. 9,017,967, and references cited therein, all of which are incorporated herein by reference in their entireties.

In particular embodiments, a megaTAL comprises a TALE DNA binding domain comprising one or more repeat units that are involved in binding of the TALE DNA binding domain to its corresponding target DNA sequence. A single "repeat unit" (also referred to as a "repeat") is typically 33-35 amino acids in length. Each TALE DNA binding domain repeat unit includes 1 or 2 DNA-binding residues making up the Repeat Variable Di-Residue (RVD), typically at positions 12 and/or 13 of the repeat. The natural (canonical) code for DNA recognition of these TALE DNA binding domains has been determined such that an HD sequence at positions 12 and 13 leads to a binding to cytosine (C), NG binds to T, NI to A, NN binds to G or A, and NG binds to T. In certain embodiments, non-canonical (atypical) RVDs are contemplated.

Illustrative examples of non-canonical RVDs suitable for use in particular megaTALs contemplated in particular embodiments include, but are not limited to HH, KH, NH, NK, NQ, RH, RN, SS, NN, SN, KN for recognition of guanine (G); NI, KI, RI, HI, SI for recognition of adenine (A); NG, HG, KG, RG for recognition of thymine (T); RD, SD, HD, ND, KD, YG for recognition of cytosine (C); NV, HN for recognition of A or G; and H*, HA, KA, N*, NA, NC, NS, RA, S* for recognition of A or T or G or C, wherein (*) means that the amino acid at position 13 is absent. Additional illustrative examples of RVDs suitable for use in particular megaTALs contemplated in particular embodiments further include those disclosed in U.S. Pat. No. 8,614,092, which is incorporated herein by reference in its entirety.

In particular embodiments, a megaTAL contemplated herein comprises a TALE DNA binding domain comprising 3 to 30 repeat units. In certain embodiments, a megaTAL comprises 3, 4, 5, 6, 7, 8, 9, 10, 11, 12, 13, 14, 15, 16, 17, 18, 19, 20, 21, 22, 23, 24, 25, 26, 27, 28, 29, or 30 TALE DNA binding domain repeat units. In a preferred embodiment, a megaTAL contemplated herein comprises a TALE DNA binding domain comprising 5-16 repeat units, more preferably 7-15 repeat units, more preferably 9-12 patents are not obvious repeat units, and more preferably 9, 10, or 11 repeat units.

In particular embodiments, a megaTAL contemplated herein comprises a TALE DNA binding domain comprising 3 to 30 repeat units and an additional single truncated TALE repeat unit comprising 20 amino acids located at the C-terminus of a set of TALE repeat units, i.e., an additional C-terminal half-TALE DNA binding domain repeat unit (amino acids −20 to −1 of the C-cap disclosed elsewhere herein, infra). Thus, in particular embodiments, a megaTAL contemplated herein comprises a TALE DNA binding domain comprising 3.5 to 30.5 repeat units. In certain embodiments, a megaTAL comprises 3.5, 4.5, 5.5, 6.5, 7.5, 8.5, 9.5, 10.5, 11.5, 12.5, 13.5, 14.5, 15.5, 16.5, 17.5, 18.5, 19.5, 20.5, 21.5, 22.5, 23.5, 24.5, 25.5, 26.5, 27.5, 28.5, 29.5, or 30.5 TALE DNA binding domain repeat units. In a preferred embodiment, a megaTAL contemplated herein comprises a TALE DNA binding domain comprising 5.5-13.5 repeat units, more preferably 7.5-12.5 repeat units, more preferably 9.5-11.5 repeat units, and more preferably 9.5, 10.5, or 11.5 repeat units.

In particular embodiments, a megaTAL comprises an "N-terminal domain (NTD)" polypeptide, one or more TALE repeat domains/units, a "C-terminal domain (CTD)" polypeptide, and an engineered meganuclease.

As used herein, the term "N-terminal domain (NTD)" polypeptide refers to the sequence that flanks the N-terminal portion or fragment of a naturally occurring TALE DNA binding domain. The NTD sequence, if present, may be of any length as long as the TALE DNA binding domain repeat units retain the ability to bind DNA. In particular embodiments, the NTD polypeptide comprises at least 120 to at least 140 or more amino acids N-terminal to the TALE DNA binding domain (0 is amino acid 1 of the most N-terminal repeat unit). In particular embodiments, the NTD polypeptide comprises at least about 120, 121, 122, 123, 124, 125, 126, 127, 128, 129, 130, 131, 132, 133, 134, 135, 136, 137, 138, 139, or at least 140 amino acids N-terminal to the TALE DNA binding domain. In one embodiment, a megaTAL contemplated herein comprises an NTD polypeptide of at least about amino acids +1 to +122 to at least about +1 to +137 of a *Xanthomonas* TALE protein (0 is amino acid 1 of the most N-terminal repeat unit). In particular embodiments, the NTD polypeptide comprises at least about 122, 123, 124, 125, 126, 127, 128, 129, 130, 131, 132, 133, 134, 135, 136, or 137 amino acids N-terminal to the TALE DNA binding domain of a *Xanthomonas* TALE protein. In one embodiment, a megaTAL contemplated herein comprises an NTD polypeptide of at least amino acids +1 to +121 of a *Ralstonia* TALE protein (0 is amino acid 1 of the most N-terminal repeat unit). In particular embodiments, the NTD polypeptide comprises at least about 121, 122, 123, 124, 125, 126, 127, 128, 129, 130, 131, 132, 133, 134, 135, 136, or 137 amino acids N-terminal to the TALE DNA binding domain of a *Ralstonia* TALE protein.

As used herein, the term "C-terminal domain (CTD)" polypeptide refers to the sequence that flanks the C-terminal portion or fragment of a naturally occurring TALE DNA binding domain. The CTD sequence, if present, may be of any length as long as the TALE DNA binding domain repeat units retain the ability to bind DNA. In particular embodiments, the CTD polypeptide comprises at least 20 to at least 85 or more amino acids C-terminal to the last full repeat of the TALE DNA binding domain (the first 20 amino acids are the half-repeat unit C-terminal to the last C-terminal full repeat unit). In particular embodiments, the CTD polypeptide comprises at least about 20, 21, 22, 23, 24, 25, 26, 27, 28, 29, 30, 31, 32, 33, 34, 35, 36, 37, 38, 39, 40, 41, 42, 443, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or at least 85 amino acids C-terminal to the last full repeat of the TALE DNA binding domain. In one embodiment, a megaTAL contemplated herein comprises a CTD polypeptide of at least about amino acids −20 to −1 of a *Xanthomonas* TALE protein (−20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a *Xanthomonas* TALE protein. In one embodiment, a megaTAL contemplated herein comprises a CTD polypeptide of at least about amino acids −20 to −1 of a *Ralstonia* TALE protein (−20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a *Ralstonia* TALE protein.

In particular embodiments, a megaTAL contemplated herein, comprises a fusion polypeptide comprising a TALE DNA binding domain engineered to bind a target sequence, a meganuclease engineered to bind and cleave a target sequence, and optionally an NTD and/or CTD polypeptide, optionally joined to each other with one or more linker polypeptides contemplated elsewhere herein. Without wishing to be bound by any particular theory, it is contemplated that a megaTAL comprising TALE DNA binding domain, and optionally an NTD and/or CTD polypeptide is fused to a linker polypeptide which is further fused to an engineered meganuclease. Thus, the TALE DNA binding domain binds a DNA target sequence that is within about 1, 2, 3, 4, 5, 6, 7, 8, 9, 10, 11, 12, 13, 14, or 15 nucleotides away from the target sequence bound by the DNA binding domain of the meganuclease. In this way, the megaTALs contemplated herein, increase the specificity and efficiency of genome editing.

In particular embodiments, a megaTAL contemplated herein, comprises one or more TALE DNA binding repeat units and an engineered LHE selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-CreI, I-SceI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I, or preferably I-CpaMI, I-HjeMI, I-OnuI, I-PanMI, and SmaMI, or more preferably I-OnuI.

In particular embodiments, a megaTAL contemplated herein, comprises an NTD, one or more TALE DNA binding repeat units, a CTD, and an engineered LHE selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-CreI, I-SceI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I, or preferably I-CpaMI, I-HjeMI, I-OnuI, I-PanMI, and SmaMI, or more preferably I-OnuI.

In particular embodiments, a megaTAL contemplated herein, comprises an NTD, about 9.5 to about 11.5 TALE DNA binding repeat units, and an engineered I-OnuI LHE selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-CreI, I-SceI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I, or preferably I-CpaMI, I-HjeMI, I-OnuI, I-PanMI, and SmaMI, or more preferably I-OnuI.

In particular embodiments, a megaTAL contemplated herein, comprises an NTD of about 122 amino acids to 137 amino acids, about 9.5, about 10.5, or about 11.5 binding repeat units, a CTD of about 20 amino acids to about 85 amino acids, and an engineered I-OnuI LHE selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-CreI, I-SceI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdi141I, or preferably I-CpaMI, I-HjeMI, I-OnuI, I-PanMI, and SmaMI, or more preferably I-OnuI.

3. Talens

In various embodiments, a plurality of transcription activator-like effector nucleases (TALENs) are introduced into a cell and engineered to bind to, and to introduce single-stranded nicks or double-strand breaks (DSBs) in a plurality of genome target sites including, but not limited to genes encoding a polypeptide that suppresses γ-globin gene expression, a TCR signaling component (e.g., constant region of TCRα gene), an immune system checkpoint, or an immunosuppressive signaling component. A "TALEN" refers to an engineered nuclease comprising an engineered TALE DNA binding domain contemplated elsewhere herein and an endonuclease domain (or endonuclease half-domain thereof), and optionally comprise one or more linkers and/or additional functional domains, e.g., an end-processing enzymatic domain of an end-processing enzyme that exhibits 5-3' exonuclease, 5-3' alkaline exonuclease, 3-5' exonuclease (e.g., Trex2), 5' flap endonuclease, helicase or template-independent DNA polymerases activity. In particular embodiments, a TALEN can be introduced into a T cell with an end-processing enzyme that exhibits 5-3' exonuclease, 5-3' alkaline exonuclease, 3-5' exonuclease (e.g., Trex2), 5' flap endonuclease, helicase or template-independent DNA polymerases activity. The TALEN and 3' processing enzyme may be introduced separately, e.g., in different vectors or separate mRNAs, or together, e.g., as a fusion protein, or in a polycistronic construct separated by a viral self-cleaving peptide or an IRES element.

In one embodiment, targeted double-stranded cleavage is achieved with two TALENs, each comprising am endonuclease half-domain can be used to reconstitute a catalytically active cleavage domain. In another embodiment, targeted double-stranded cleavage is achieved using a single polypeptide comprising a TALE DNA binding domain and two endonuclease half-domains.

TALENs contemplated in particular embodiments comprise an NTD, a TALE DNA binding domain comprising about 3 to 30 repeat units, e.g., about 3, 4, 5, 6, 7, 8, 9, 10, 11, 12, 13, 14, 15, 16, 17, 18, 19, 20, 21, 22, 23, 24, 25, 26, 27, 28, 29, or 30 repeat units, and an endonuclease domain or half-domain.

TALENs contemplated in particular embodiments comprise an NTD, a TALE DNA binding domain comprising about 3.5 to 30.5 repeat units, e.g., about 3.5, 4.5, 5.5, 6.5, 7.5, 8.5, 9.5, 10.5, 11.5, 12.5, 13.5, 14.5, 15.5, 16.5, 17.5, 18.5, 19.5, 20.5, 21.5, 22.5, 23.5, 24.5, 25.5, 26.5, 27.5, 28.5, 29.5, or 30.5 repeat units, a CTD, and an endonuclease domain or half-domain.

TALENs contemplated in particular embodiments comprise an NTD of about 121 amino acids to about 137 amino acids as disclosed elsewhere herein, a TALE DNA binding domain comprising about 9.5 to about 11.5 repeat units (i.e., about 9.5, about 10.5, or about 11.5 repeat units), a CTD of about 20 amino acids to about 85 amino acids, and an endonuclease domain or half domain.

In particular embodiments, a TALEN comprises an endonuclease domain of a type restriction endonuclease. Restriction endonucleases (restriction enzymes) are present in many species and are capable of sequence-specific binding to DNA (at a recognition site), and cleaving DNA at or near the site of binding. Certain restriction enzymes (e.g., Type-IIS) cleave DNA at sites removed from the recognition site and have separable binding and endonuclease domains. In one embodiment, TALENs comprise the endonuclease domain (or endonuclease half-domain) from at least one Type-IIS restriction enzyme and one or more TALE DNA-binding domains contemplated elsewhere herein.

Illustrative examples of Type-IIS restriction endonuclease domains suitable for use in TALENs contemplated in particular embodiments include endonuclease domains of the at least 1633 Type-IIS restriction endonucleases disclosed at "rebase.neb.com/cgi-bin/sublist?S."

Additional illustrative examples of Type-IIS restriction endonuclease domains suitable for use in TALENs contemplated in particular embodiments include those of endonucleases selected from the group consisting of: Aar I, Ace III, Aci I, Alo I, Alw26 I, Bae I, Bbr7 I, Bbv I, Bbv II, BbvC I, Bcc I, Bce83 I, BceA I, Bcef I, Bcg I, BciV I, Bfi I, Bin I, Bmg I, Bpu10 I, BsaX I, Bsb I, BscA I, BscG I, BseR I, BseY I, Bsi I, Bsm I, BsmA I, BsmF I, Bsp24 I, BspG I, BspM I, BspNC I, Bsr I, BsrB I, BsrD I, BstF5 I, Btr I, Bts I, Cdi I, CjeP I, Drd II, Earl, Eci I, Eco31 I, Eco57 I, Eco57M I, Esp3 I, Fau I, Fin I, Fok I, Gdi II, Gsu I, Hga I, Hin4 II, Hph I, Ksp632 I, Mbo II, Mly I, Mme I, Mnl I, Pfl1108, I Ple I, Ppi I Psr I, RleA I, Sap I, SfaN I, Sim I, SspD5 I, Sth132 I, Sts I, TspDT I, TspGW I, Tth111 II, UbaP I, Bsa I, and BsmB I.

In one embodiment, a TALEN contemplated herein comprises an endonuclease domain of the Fok I Type-IIS restriction endonuclease.

In one embodiment, a TALEN contemplated herein comprises a TALE DNA binding domain and an endonuclease half-domain from at least one Type-IIS restriction endonuclease to enhance cleavage specificity, optionally wherein the endonuclease half-domain comprises one or more amino acid substitutions or modifications that minimize or prevent homodimerization.

Illustrative examples of cleavage half-domains suitable for use in particular embodiments contemplated in particular embodiments include those disclosed in U.S. Patent Publication Nos. 20050064474; 20060188987, 20080131962, 20090311787; 20090305346; 20110014616, and 20110201055, each of which are incorporated by reference herein in its entirety.

4. Zinc Finger Nucleases

In various embodiments, a plurality of zinc finger nucleases (ZFNs) are introduced into a cell and engineered to bind to, and to introduce single-stranded nicks or double-strand breaks (DSBs) in a plurality of genome target sites including, but not limited to genes encoding a polypeptide that suppresses 7-globin gene expression, a TCR signaling component (e.g., constant region of TCRα gene), an immune system checkpoint, or an immunosuppressive signaling component. A "ZFN" refers to an engineered nuclease comprising one or more zinc finger DNA binding domains and an endonuclease domain (or endonuclease half-domain thereof), and optionally comprise one or more linkers and/or additional functional domains, e.g., an end-processing enzymatic domain of an end-processing enzyme that exhibits 5-3' exonuclease, 5-3' alkaline exonuclease, 3-5' exonuclease (e.g., Trex2), 5' flap endonuclease, helicase or template-independent DNA polymerases activity. In particular embodiments, a ZFN can be introduced into a T cell with an end-processing enzyme that exhibits 5-3' exonuclease, 5-3' alkaline exonuclease, 3-5' exonuclease (e.g., Trex2), 5' flap endonuclease, helicase or template-independent DNA polymerases activity. The ZFN and 3' processing enzyme may be introduced separately, e.g., in different vectors or separate mRNAs, or together, e.g., as a fusion protein, or in a polycistronic construct separated by a viral self-cleaving peptide or an IRES element.

In one embodiment, targeted double-stranded cleavage is achieved using two ZFNs, each comprising an endonuclease half-domain can be used to reconstitute a catalytically active cleavage domain. In another embodiment, targeted double-stranded cleavage is achieved with a single polypeptide comprising one or more zinc finger DNA binding domains and two endonuclease half-domains.

In one embodiment, a ZNF comprises a TALE DNA binding domain contemplated elsewhere herein, a zinc finger DNA binding domain, and an endonuclease domain (or endonuclease half-domain) contemplated elsewhere herein.

In one embodiment, a ZNF comprises a zinc finger DNA binding domain, and a meganuclease contemplated elsewhere herein.

In particular embodiments, the ZFN comprises a zinger finger DNA binding domain that has one, two, three, four, five, six, seven, or eight or more zinger finger motifs and an endonuclease domain (or endonuclease half-domain). Typically, a single zinc finger motif is about 30 amino acids in length. Zinc fingers motifs include both canonical $C_2H_2$ zinc fingers, and non-canonical zinc fingers such as, for example, $C_3H$ zinc fingers and $C_4$ zinc fingers.

Zinc finger binding domains can be engineered to bind any DNA sequence. Candidate zinc finger DNA binding domains for a given 3 bp DNA target sequence have been identified and modular assembly strategies have been devised for linking a plurality of the domains into a multi-finger peptide targeted to the corresponding composite DNA target sequence. Other suitable methods known in the art can also be used to design and construct nucleic acids encoding zinc finger DNA binding domains, e.g., phage display, random mutagenesis, combinatorial libraries, computer/rational design, affinity selection, PCR, cloning from cDNA or genomic libraries, synthetic construction and the like. (See, e.g., U.S. Pat. No. 5,786,538; Wu et al., *PNAS* 92:344-348 (1995); Jamieson et al., *Biochemistry* 33:5689-5695 (1994); Rebar & Pabo, *Science* 263:671-673 (1994); Choo & Klug, *PNAS* 91:11163-11167 (1994); Choo & Klug, *PNAS* 91: 11168-11172 (1994); Desjarlais & Berg, *PNAS* 90:2256-2260 (1993); Desjarlais & Berg, *PNAS* 89:7345-7349 (1992); Pomerantz et al., *Science* 267:93-96 (1995); Pomerantz et al., *PNAS* 92:9752-9756 (1995); Liu et al., *PNAS* 94:5525-5530 (1997); Griesman & Pabo, *Science* 275:657-661 (1997); Desjarlais & Berg, *PNAS* 91:11-99-11103 (1994)).

Individual zinc finger motifs bind to a three or four nucleotide sequence. The length of a sequence to which a zinc finger binding domain is engineered to bind (e.g., a target sequence) will determine the number of zinc finger motifs in an engineered zinc finger binding domain. For example, for ZFNs in which the zinc finger motifs do not bind to overlapping subsites, a six-nucleotide target sequence is bound by a two-finger binding domain; a nine-nucleotide target sequence is bound by a three-finger binding domain, etc. In particular embodiments, DNA binding sites for individual zinc fingers motifs in a target site need not be contiguous, but can be separated by one or several nucleotides, depending on the length and nature of the linker sequences between the zinc finger motifs in a multi-finger binding domain.

In particular embodiments, ZNFs contemplated herein comprise, a zinc finger DNA binding domain comprising two, three, four, five, six, seven or eight or more zinc finger motifs, and an endonuclease domain or half-domain from at least one Type-IIS restriction enzyme and one or more TALE DNA-binding domains contemplated elsewhere herein.

In particular embodiments, ZNFs contemplated herein comprise, a zinc finger DNA binding domain comprising three, four, five, six, seven or eight or more zinc finger motifs, and an endonuclease domain or half-domain from at least one Type-IIS restriction enzyme selected from the group consisting of: Aar I, Ace III, Aci I, Alo I, Alw26 I, Bae I, Bbr7 I, Bbv I, Bbv II, BbvC I, Bcc I, Bce83 I, BceA I, Bcef I, Bcg I, BciV I, Bfi I, Bin I, Bmg I, Bpu10 I, BsaX I, Bsb I, BscA I, BscG I, BseR I, BseY I, Bsi I, Bsm I, BsmA I, BsmF I, Bsp24 I, BspG I, BspM I, BspNC I, Bsr I, BsrB I, BsrD I, BstF5 I, Btr I, Bts I, Cdi I, CjeP I, Drd II, Earl, Eci I, Eco31 I, Eco57 I, Eco57M I, Esp3 I, Fau I, Fin I, Fok I, Gdi II, Gsu I, Hga I, Hin4 II, Hph I, Ksp632 I, Mbo II, Mly I, Mme I, Mnl I, Pfl1108, I Ple I, Ppi I Psr I, RleA I, Sap I, SfaN I, Sim I, SspD5 I, Sth132 I, Sts I, TspDT I, TspGW I, Tth111 II, UbaP I, Bsa I, and BsmB I.

In particular embodiments, ZNFs contemplated herein comprise, a zinc finger DNA binding domain comprising three, four, five, six, seven or eight or more zinc finger motifs, and an endonuclease domain or half-domain from the Fok I Type-IIS restriction endonuclease.

In one embodiment, a ZFN contemplated herein comprises a zinc finger DNA binding domain and an endonuclease half-domain from at least one Type-IIS restriction endonuclease to enhance cleavage specificity, optionally wherein the endonuclease half-domain comprises one or more amino acid substitutions or modifications that minimize or prevent homodimerization.

5. CRISPR/Cas Nuclease System

In various embodiments, a CRISPR (Clustered Regularly Interspaced Short Palindromic Repeats)/Cas (CRISPR Associated) nuclease system is introduced into a cell and engineered to bind to, and to introduce single-stranded nicks or double-strand breaks (DSBs) in a plurality of genome target sites including, but not limited to genes encoding a polypeptide that suppresses γ-globin gene expression, a TCR signaling component (e.g., constant region of TCRα gene), an immune system checkpoint, or an immunosuppressive signaling component. The CRISPR/Cas nuclease system is a recently engineered nuclease system based on a bacterial system that can be used for mammalian genome engineering. See, e.g., Jinek et al. (2012) *Science* 337:816-821; Cong et al. (2013) *Science* 339:819-823; Mali et al. (2013) *Science* 339:823-826; Qi et al. (2013) *Cell* 152:1173-1183; Jinek et al. (2013), *eLife* 2:e00471; David Segal (2013) *eLife* 2:e00563; Ran et al. (2013) *Nature Protocols* 8(11):2281-2308; Zetsche et al. (2015) *Cell* 163(3):759-771, each of which is incorporated herein by reference in its entirety.

In one embodiment, the CRISPR/Cas nuclease system comprises Cas nuclease and one or more RNAs that recruit the Cas nuclease to the target site, e.g., a transactivating cRNA (tracrRNA) and a CRISPR RNA (crRNA), or a single guide RNA (sgRNA). crRNA and tracrRNA can engineered into one polynucleotide sequence referred to herein as a "single guide RNA" or "sgRNA."

In one embodiment, the Cas nuclease is engineered as a double-stranded DNA endonuclease or a nickase or catalytically dead Cas, and forms a target complex with a crRNA and a tracrRNA, or sgRNA, for site specific DNA recognition and site-specific cleavage of the protospacer target sequence located within genes encoding a polypeptide that suppresses γ-globin gene expression, a TCR signaling component (e.g., constant region of TCRα gene), an immune system checkpoint, or an immunosuppressive signaling component. The protospacer motif abuts a short protospacer adjacent motif (PAM), which plays a role in recruiting a Cas/RNA complex. Cas polypeptides recognize PAM motifs specific to the Cas polypeptide. Accordingly, the CRISPR/Cas system can be used to target and cleave either or both strands of a double-stranded polynucleotide sequence flanked by particular 3' PAM sequences specific to a particular Cas polypeptide. PAMs may be identified using bioinformatics or using experimental approaches. Esvelt et al., 2013, *Nature Methods*. 10(11):1116-1121, which is hereby incorporated by reference in its entirety.

In one embodiment, the Cas nuclease comprises one or more heterologous DNA binding domains, e.g., a TALE DNA binding domain or zinc finger DNA binding domain. Fusion of the Cas nuclease to TALE or zinc finger DNA binding domains increases the DNA cleavage efficiency and specificity. In a particular embodiment, a Cas nuclease optionally comprises one or more linkers and/or additional functional domains, e.g., an end-processing enzymatic domain of an end-processing enzyme that exhibits 5-3' exonuclease, 5-3' alkaline exonuclease, 3-5' exonuclease (e.g., Trex2), 5' flap endonuclease, helicase or template-independent DNA polymerases activity. In particular embodiments, a Cas nuclease can be introduced into a T cell with an end-processing enzyme that exhibits 5-3' exonuclease, 5-3' alkaline exonuclease, 3-5' exonuclease (e.g., Trex2), 5' flap endonuclease, helicase or template-independent DNA polymerases activity. The Cas nuclease and 3' processing enzyme may be introduced separately, e.g., in different vectors or separate mRNAs, or together, e.g., as a fusion protein, or in a polycistronic construct separated by a viral self-cleaving peptide or an IRES element.

In various embodiments, the Cas nuclease is Cas9 or Cpf1.

Illustrative examples of Cas9 polypeptides suitable for use in particular embodiments contemplated in particular embodiments may be obtained from bacterial species including, but not limited to: *Enterococcus faecium, Enterococcus italicus, Listeria innocua, Listeria monocytogenes, Listeria seeligeri, Listeria ivanovii, Streptococcus agalactiae, Streptococcus anginosus, Streptococcus bovis, Streptococcus dysgalactiae, Streptococcus equinus, Streptococcus gallolyticus, Streptococcus macacae, Streptococcus mutans, Streptococcus pseudoporcinus, Streptococcus pyogenes, Streptococcus thermophilus, Streptococcus gordonii, Streptococcus infantarius, Streptococcus macedonicus, Streptococcus mitis, Streptococcus pasteurianus, Streptococcus suis, Streptococcus vestibularis, Streptococcus sanguinis, Streptococcus downei, Neisseria bacilliformis, Neisseria cinerea, Neisseria flavescens, Neisseria lactamica, Neisseria meningitidis, Neisseria subflava, Lactobacillus brevis, Lactobacillus buchneri, Lactobacillus casei, Lactobacillus paracasei, Lactobacillus fermentum, Lactobacillus gasseri, Lactobacillus jensenii, Lactobacillus johnsonii, Lactobacillus rhamnosus, Lactobacillus ruminis, Lactobacillus salivarius, Lactobacillus sanfranciscensis, Corynebacterium accolens, Corynebacterium diphtheriae, Corynebacterium matruchotii, Campylobacter jejuni, Clostridium perfringens, Treponema vincentii, Treponema phagedenis,* and *Treponema denticola*.

Illustrative examples of Cpf1 polypeptides suitable for use in particular embodiments contemplated in particular embodiments may be obtained from bacterial species including, but not limited to: *Francisella* spp., *Acidaminococcus* spp., *Prevotella* spp., *Lachnospiraceae* spp., among others.

Conserved regions of Cas9 orthologs include a central HNH endonuclease domain and a split RuvC/RNase H domain. Cpf1 orthologs possess a RuvC/RNase H domain but no discernable HNH domain. The HNH and RuvC-like domains are each responsible for cleaving one strand of the double-stranded DNA target sequence. The HNH domain of the Cas9 nuclease polypeptide cleaves the DNA strand complementary to the tracrRNA:crRNA or sgRNA. The RuvC-like domain of the Cas9 nuclease cleaves the DNA strand that is not-complementary to the tracrRNA:crRNA or sgRNA. Cpf1 is predicted to act as a dimer wherein each RuvC-like domain of Cpf1 cleaves either the complementary or non-complementary strand of the target site. In particular embodiments, a Cas9 nuclease variant (e.g., Cas9 nickase) is contemplated comprising one or more amino acids additions, deletions, mutations, or substitutions in the HNH or RuvC-like endonuclease domains that decreases or eliminates the nuclease activity of the variant domain.

Illustrative examples of Cas9 HNH mutations that decrease or eliminate the nuclease activity in the domain include, but are not limited to: *S. pyogenes* (D10A); *S. thermophilis* (D9A); *T. denticola* (D13A); and *N. meningitidis* (D16A).

Illustrative examples of Cas9 RuvC-like domain mutations that decrease or eliminate the nuclease activity in the domain include, but are not limited to: *S. pyogenes* (D839A, H840A, or N863A); *S. thermophilis* (D598A, H599A, or N622A); *T. denticola* (D878A, H879A, or N902A); and *N. meningitidis* (D587A, H588A, or N611A).

E. Polypeptides

Various polypeptides are contemplated herein, including, but not limited to, immunopotency enhancers, immunosuppressive signal dampers, engineered antigen receptors, and engineered nucleases. "Polypeptide," "polypeptide fragment," "peptide" and "protein" are used interchangeably, unless specified to the contrary, and according to conventional meaning, i.e., as a sequence of amino acids. In one embodiment, a "polypeptide" includes fusion polypeptides and other variants. Polypeptides can be prepared using any of a variety of well-known recombinant and/or synthetic techniques. Polypeptides are not limited to a specific length, e.g., they may comprise a full length protein sequence, a fragment of a full length protein, or a fusion protein, and may include post-translational modifications of the polypeptide, for example, glycosylations, acetylations, phosphorylations and the like, as well as other modifications known in the art, both naturally occurring and non-naturally occurring.

Illustrative examples of polypeptides contemplated in particular embodiments include, but are not limited to homing endonuclease variants, megaTALs, globins, anti-sickling globins, BiTEs, cytokines, chemokines, cytotoxins, and cytokine receptors, flip receptors, immunosuppressive signal dampers, CARs, DARICs, TCRs, and zetakines.

Polypeptides include "polypeptide variants." Polypeptide variants may differ from a naturally occurring polypeptide in one or more amino acid substitutions, deletions, additions and/or insertions. Such variants may be naturally occurring or may be synthetically generated, for example, by modifying one or more amino acids of the above polypeptide sequences. For example, in particular embodiments, it may be desirable to improve the biological properties of a polypeptide by introducing one or more substitutions, deletions, additions and/or insertions into the polypeptide. In particular embodiments, polypeptides include polypeptides having at least about 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity to any of the reference sequences contemplated herein, typically where the variant maintains at least one biological activity of the reference sequence.

Polypeptides variants include biologically active "polypeptide fragments." Illustrative examples of biologically active polypeptide fragments include DNA binding domains, nuclease domains, and the like. As used herein, the term "biologically active fragment" or "minimal biologically active fragment" refers to a polypeptide fragment that retains at least 100%, at least 90%, at least 80%, at least 70%, at least 60%, at least 50%, at least 40%, at least 30%, at least 20%, at least 10%, or at least 5% of the naturally occurring polypeptide activity. In preferred embodiments, the biological activity is binding affinity and/or cleavage activity for a target sequence. In certain embodiments, a polypeptide fragment can comprise an amino acid chain at least 5 to about 1700 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more amino acids long. In particular embodiments, a polypeptide comprises a biologically active fragment of a homing endonuclease variant. In particular embodiments, the polypeptides set forth herein may comprise one or more amino acids denoted as "X." "X" if present in an amino acid SEQ ID NO, refers to any amino acid. One or more "X" residues may be present at the N- and C-terminus of an amino acid sequence set forth in particular SEQ ID NOs contemplated herein. If the "X" amino acids are not present the remaining amino acid sequence set forth in a SEQ ID NO may be considered a biologically active fragment.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., (*Molecular Biology of the Gene,* Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure (Natl. Biomed Res. Found,* Washington, D.C.).

In certain embodiments, a variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides contemplated in particular embodiments, polypeptides include polypeptides having at least about and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence, e.g., according to Table 1.

TABLE 1

Amino Acid Codons

| Amino Acids | One letter code | Three letter code | Codons |
| --- | --- | --- | --- |
| Alanine | A | Ala | GCA GCC GCG GCU |
| Cysteine | C | Cys | UGC UGU |
| Aspartic acid | D | Asp | GAC GAU |
| Glutamic acid | E | Glu | GAA GAG |
| Phenylalanine | F | Phe | UUC UUU |
| Glycine | G | Gly | GGA GGC GGG GGU |
| Histidine | H | His | CAC CAU |
| Isoleucine | I | Iso | AUA AUC AUU |
| Lysine | K | Lys | AAA AAG |
| Leucine | L | Leu | UUA UUG CUA CUC CUG CUU |
| Methionine | M | Met | AUG |
| Asparagine | N | Asn | AAC AAU |
| Proline | P | Pro | CCA CCC CCG CCU |
| Glutamine | Q | Gln | CAA CAG |
| Arginine | R | Arg | AGA AGG CGA CGC CGG CGU |
| Serine | S | Ser | AGC AGU UCA UCC UCG UCU |
| Threonine | T | Thr | ACA ACC ACG ACU |
| Valine | V | Val | GUA GUC GUG GUU |
| Tryptophan | W | Trp | UGG |
| Tyrosine | Y | Tyr | UAC UAU |

Guidance in determining which amino acid residues can be substituted, inserted, or deleted without abolishing biological activity can be found using computer programs well known in the art, such as DNASTAR, DNA Strider, Geneious, Mac Vector, or Vector NTI software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224).

In one embodiment, where expression of two or more polypeptides is desired, the polynucleotide sequences encoding them can be separated by and IRES sequence as disclosed elsewhere herein.

Polypeptides contemplated in particular embodiments include fusion polypeptides. In particular embodiments, fusion polypeptides and polynucleotides encoding fusion polypeptides are provided. Fusion polypeptides and fusion proteins refer to a polypeptide having at least two, three, four, five, six, seven, eight, nine, or ten polypeptide segments.

In another embodiment, two or more polypeptides can be expressed as a fusion protein that comprises one or more self-cleaving polypeptide sequences as disclosed elsewhere herein.

In one embodiment, a fusion protein contemplated herein comprises one or more DNA binding domains and one or more nucleases, and one or more linker and/or self-cleaving polypeptides.

In one embodiment, a fusion protein contemplated herein comprises nuclease variant; a linker or self-cleaving peptide; and an end-processing enzyme including but not limited to a 5'-3' exonuclease, a 5'-3' alkaline exonuclease, and a 3'-5' exonuclease (e.g., Trex2).

Fusion polypeptides can comprise one or more polypeptide domains or segments including, but are not limited to signal peptides, cell permeable peptide domains (CPP), DNA binding domains, nuclease domains, etc., epitope tags (e.g., maltose binding protein ("MBP"), glutathione S transferase (GST), HIS6, MYC, FLAG, V5, VSV-G, and HA), polypeptide linkers, and polypeptide cleavage signals. Fusion polypeptides are typically linked C-terminus to N-terminus, although they can also be linked C-terminus to C-terminus, N-terminus to N-terminus, or N-terminus to C-terminus. In particular embodiments, the polypeptides of the fusion protein can be in any order. Fusion polypeptides or fusion proteins can also include conservatively modified variants, polymorphic variants, alleles, mutants, subsequences, and interspecies homologs, so long as the desired activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as disclosed elsewhere herein.

Fusion polypeptides may optionally comprises a linker that can be used to link the one or more polypeptides or domains within a polypeptide. A peptide linker sequence may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. Linker sequences are not required when a particular fusion polypeptide segment contains non-essential N-terminal amino acid regions that can be used to separate the functional domains and prevent steric interference. Preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between.

Exemplary linkers include, but are not limited to the following amino acid sequences: glycine polymers $(G)_n$; glycine-serine polymers $(G_{1-5}S_{1-5})_n$, where n is an integer of at least one, two, three, four, or five; glycine-alanine polymers; alanine-serine polymers; GGG (SEQ ID NO: 3); DGGGS (SEQ ID NO: 4); TGEKP (SEQ ID NO: 5) (see e.g., Liu et al., *PNAS* 5525-5530 (1997)); GGRR (SEQ ID NO: 6) (Pomerantz et al. 1995, supra); $(GGGGS)_n$ wherein n=1, 2, 3, 4 or 5 (SEQ ID NO: 7) (Kim et al., PNAS 93, 1156-1160 (1996.); EGKSSGSGSESKVD (SEQ ID NO: 8) (Chaudhary et al., 1990, *Proc. Natl. Acad. Sci. U.S.A.* 87:1066-1070); KESGSVSSEQLAQFRSLD (SEQ ID NO: 9) (Bird et al., 1988, *Science* 242:423-426), GGRRGGGS (SEQ ID NO: 10); LRQRDGERP (SEQ ID NO: 11); LRQKDGGGSERP (SEQ ID NO: 12); LRQKD$(GGGS)_2$ERP (SEQ ID NO: 13). Alternatively, flexible linkers can be rationally designed using a computer program capable of modeling both DNA-binding sites and the peptides themselves (Desjarlais & Berg, *PNAS* 90:2256-2260 (1993), *PNAS* 91:11099-11103 (1994) or by phage display methods.

Fusion polypeptides may further comprise a polypeptide cleavage signal between each of the polypeptide domains described herein or between an endogenous open reading frame and a polypeptide encoded by a donor repair template. In addition, a polypeptide cleavage site can be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic,* 5(8); 616-26).

Suitable protease cleavages sites and self-cleaving peptides are known to the skilled person (see, e.g., in Ryan et al., 1997. *J Gener. Virol.* 78, 699-722; Scymczak et al. (2004) Nature Biotech. 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S) (SEQ ID NO: 14), for example, ENLYFQG (SEQ ID NO: 15) and ENLYFQS (SEQ ID NO: 16), wherein X represents any amino acid (cleavage by TEV occurs between Q and G or Q and S).

In certain embodiments, the self-cleaving polypeptide site comprises a 2A or 2A-like site, sequence or domain (Donnelly et al., 2001. *J Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

Illustrative examples of 2A sites are provided in Table 2.

TABLE 2

Exemplary 2A sites include the following sequences:

| | |
|---|---|
| SEQ ID NO: 17 | GSGATNFSLLKQAGDVEENPGP |
| SEQ ID NO: 18 | ATNFSLLKQAGDVEENPGP |
| SEQ ID NO: 19 | LLKQAGDVEENPGP |
| SEQ ID NO: 20 | GSGEGRGSLLTCGDVEENPGP |
| SEQ ID NO: 21 | EGRGSLLTCGDVEENPGP |
| SEQ ID NO: 22 | LLTCGDVEENPGP |
| SEQ ID NO: 23 | GSGQCTNYALLKLAGDVESNPGP |
| SEQ ID NO: 24 | QCTNYALLKLAGDVESNPGP |
| SEQ ID NO: 25 | LLKLAGDVESNPGP |
| SEQ ID NO: 26 | GSGVKQTLNFDLLKLAGDVESNPGP |
| SEQ ID NO: 27 | VKQTLNFDLLKLAGDVESNPGP |
| SEQ ID NO: 28 | LLKLAGDVESNPGP |
| SEQ ID NO: 29 | LLNFDLLKLAGDVESNPGP |
| SEQ ID NO: 30 | TLNFDLLKLAGDVESNPGP |
| SEQ ID NO: 31 | LLKLAGDVESNPGP |
| SEQ ID NO: 32 | NFDLLKLAGDVESNPGP |
| SEQ ID NO: 33 | QLLNFDLLKLAGDVESNPGP |
| SEQ ID NO: 34 | APVKQTLNFDLLKLAGDVESNPGP |
| SEQ ID NO: 35 | VTELLYRMKRAETYCPRPLLAIHPTEARHKQKIVAPVKQT |
| SEQ ID NO: 36 | LNFDLLKLAGDVESNPGP |
| SEQ ID NO: 37 | LLAIHPTEARHKQKIVAPVKQTLNFDLLKLAGDVESNPGP |
| SEQ ID NO: 38 | EARHKQKIVAPVKQTLNFDLLKLAGDVESNPGP |

F. Polynucleotides

In particular embodiments, DNA donor repair template polynucleotides and polynucleotides encoding immunopotency enhancers, immunosuppressive signal dampers, engineered antigen receptors, and engineered nucleases contemplated herein are provided. As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, short interfering RNA (siRNA), short hairpin RNA (shRNA), microRNA (miRNA), ribozymes, genomic RNA (gRNA), plus strand RNA (RNA(+)), minus strand RNA (RNA(−)), tracrRNA, crRNA, single guide RNA (sgRNA), synthetic RNA, synthetic mRNA, genomic DNA (gDNA), PCR amplified DNA, complementary DNA (cDNA), synthetic DNA, or recombinant DNA. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

In particular embodiments, polynucleotides may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of: (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

As used herein the term "nucleotide" refers to a heterocyclic nitrogenous base in N-glycosidic linkage with a phosphorylated sugar. Nucleotides are understood to include natural bases, and a wide variety of art-recognized modified bases. Such bases are generally located at the 1′ position of a nucleotide sugar moiety. Nucleotides generally comprise a base, sugar and a phosphate group. In ribonucleic acid (RNA), the sugar is a ribose, and in deoxyribonucleic acid (DNA) the sugar is a deoxyribose, i.e., a sugar lacking a hydroxyl group that is present in ribose. Exemplary natural nitrogenous bases include the purines, adenosine (A) and guanidine (G), and the pyrimidines, cytidine (C) and thymidine (T) (or in the context of RNA, uracil (U)). The C-1 atom of deoxyribose is bonded to N-1 of a pyrimidine or N-9 of a purine. Nucleotides are usually mono, di- or triphosphates. The nucleotides can be unmodified or modified at the sugar, phosphate and/or base moiety, (also referred to interchangeably as nucleotide analogs, nucleotide derivatives, modified nucleotides, non-natural nucleotides, and non-standard nucleotides; see for example, WO 92/07065 and WO 93/15187). Examples of modified nucleic acid bases are summarized by Limbach et al., (1994, *Nucleic Acids Res.* 22, 2183-2196).

A nucleotide may also be regarded as a phosphate ester of a nucleoside, with esterification occurring on the hydroxyl group attached to C-5 of the sugar. As used herein, the term "nucleoside" refers to a heterocyclic nitrogenous base in N-glycosidic linkage with a sugar. Nucleosides are recognized in the art to include natural bases, and also to include well known modified bases. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, nucleoside derivatives, modified nucleosides, non-natural nucleosides, or non-standard nucleosides). As also noted above, examples of modified nucleic acid bases are summarized by Limbach et al., (1994, *Nucleic Acids Res.* 22, 2183-2196).

In various illustrative embodiments, polynucleotides contemplated herein include, but are not limited to DNA donor repair template polynucleotides and polynucleotides encoding immunopotency enhancers, immunosuppressive signal dampers, engineered antigen receptors, and engineered nucleases, and expression vectors, viral vectors, and transfer plasmids comprising polynucleotides contemplated herein.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide.

In one embodiment, a polynucleotide comprises a nucleotide sequence that hybridizes to a target nucleic acid sequence under stringent conditions. To hybridize under "stringent conditions" describes hybridization protocols in which nucleotide sequences at least 60% identical to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., *Current Protocols in Molecular Biology*, John Wiley & Sons Inc., 1994-1998, Chapter 15.

In various embodiments, a polynucleotide comprises an mRNA encoding a polypeptide contemplated herein. In certain embodiments, the mRNA comprises a cap, one or more nucleotides, and a poly(A) tail.

As used herein, the terms "5' cap" or "5' cap structure" or "5' cap moiety" refer to a chemical modification, which has been incorporated at the 5' end of an mRNA. The 5' cap is involved in nuclear export, mRNA stability, and translation.

In particular embodiments, a mRNA contemplated herein comprises a 5' cap comprising a 5'-ppp-5'-triphosphate linkage between a terminal guanosine cap residue and the 5'-terminal transcribed sense nucleotide of the mRNA molecule. This 5'-guanylate cap may then be methylated to generate an N7-methyl-guanylate residue.

Illustrative examples of 5' cap suitable for use in particular embodiments of the mRNA polynucleotides contemplated herein include, but are not limited to: unmethylated 5' cap analogs, e.g., G(5')ppp(5')G, G(5')ppp(5')C, G(5')ppp(5')A; methylated 5' cap analogs, e.g., m$^7$G(5')ppp(5')G, m$^7$G(5')ppp(5')C, and m$^7$G(5')ppp(5')A; dimethylated 5' cap analogs, e.g., m$^{2,7}$G(5')ppp(5')G, m$^{2,7}$G(5')ppp(5')C, and m$^{2,7}$G(5')ppp(5')A; trimethylated 5' cap analogs, e.g., m$^{2,2,7}$G(5')ppp(5')G, m$^{2,2,7}$G(5')ppp(5')C, and m$^{2,2,7}$G(5')ppp(5')A; dimethylated symmetrical 5' cap analogs, e.g., m$^7$G(5')pppm$^7$(5')G, m$^7$G(5')pppm$^7$(5')C, and m$^7$G(5')pppm$^7$(5')A; and anti-reverse 5' cap analogs, e.g, Anti-Reverse Cap Analog (ARCA) cap, designated 3'O-Me-m$^7$G(5')ppp(5')G, 2'O-Me-m$^7$G(5')ppp(5')G, 2'O-Me-m$^7$G(5')ppp(5')C, 2'O-Me-m$^7$G(5')ppp(5')A, m$^7$2'd(5')ppp(5')G, m$^7$2'd(5')ppp(5')C, m$^7$2'd(5')ppp(5')A, 3'O-Me-m$^7$G(5')ppp(5')C, 3'O-Me-m$^7$G(5')ppp(5')A, m$^7$3'd(5')ppp(5')G, m$^7$3'd(5')ppp(5')C, m$^7$3'd(5')ppp(5')A and their tetraphosphate derivatives) (see, e.g., Jemielity et al., RNA, 9: 1108-1122 (2003)).

In particular embodiments, mRNAs comprise a 5' cap that is a 7-methyl guanylate ("m$^7$G") linked via a triphosphate bridge to the 5'-end of the first transcribed nucleotide, resulting in m$^7$G(5')ppp(5')N, where N is any nucleoside.

In some embodiments, mRNAs comprise a 5' cap wherein the cap is a Cap0 structure (Cap0 structures lack a 2'-O-methyl residue of the ribose attached to bases 1 and 2), a Cap1 structure (Cap1 structures have a 2'-O-methyl residue at base 2), or a Cap2 structure (Cap2 structures have a 2'-O-methyl residue attached to both bases 2 and 3).

In one embodiment, an mRNA comprises a m$^7$G(5')ppp (5')G cap.

In one embodiment, an mRNA comprises an ARCA cap.

In particular embodiments, an mRNA contemplated herein comprises one or more modified nucleosides.

In one embodiment, an mRNA comprises one or more modified nucleosides selected from the group consisting of: pseudouridine, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methyl-guanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In one embodiment, an mRNA comprises one or more modified nucleosides selected from the group consisting of: pseudouridine, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In one embodiment, an mRNA comprises one or more modified nucleosides selected from the group consisting of 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In one embodiment, an mRNA comprises one or more modified nucleosides selected from the group consisting of 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In one embodiment, an mRNA comprises one or more modified nucleosides selected from the group consisting of inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxoguanosine, 7-methyl-8-oxo-guanosine, 1-methyl-6-thio-guanosine, N2-methyl-6-thio-guanosine, and N2,N2-dimethyl-6-thio-guanosine.

In one embodiment, an mRNA comprises one or more pseudouridines, one or more 5-methyl-cytosines, and/or one or more 5-methyl-cytidines.

In one embodiment, an mRNA comprises one or more pseudouridines.

In one embodiment, an mRNA comprises one or more 5-methyl-cytidines.

In one embodiment, an mRNA comprises one or more 5-methyl-cytosines.

In particular embodiments, an mRNA contemplated herein comprises a poly(A) tail to help protect the mRNA from exonuclease degradation, stabilize the mRNA, and facilitate translation. In certain embodiments, an mRNA comprises a 3' poly(A) tail structure.

In particular embodiments, the length of the poly(A) tail is at least about 10, 25, 50, 75, 100, 150, 200, 250, 300, 350, 400, 450, or at least about 500 or more adenine nucleotides or any intervening number of adenine nucleotides. In particular embodiments, the length of the poly(A) tail is at least about 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 202, 203, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, or 275 or more adenine nucleotides.

In particular embodiments, the length of the poly(A) tail is about 10 to about 500 adenine nucleotides, about 50 to about 500 adenine nucleotides, about 100 to about 500 adenine nucleotides, about 150 to about 500 adenine nucleotides, about 200 to about 500 adenine nucleotides, about 250 to about 500 adenine nucleotides, about 300 to about 500 adenine nucleotides, about 50 to about 450 adenine nucleotides, about 50 to about 400 adenine nucleotides, about 50 to about 350 adenine nucleotides, about 100 to about 500 adenine nucleotides, about 100 to about 450 adenine nucleotides, about 100 to about 400 adenine nucleotides, about 100 to about 350 adenine nucleotides, about 100 to about 300 adenine nucleotides, about 150 to about 500 adenine nucleotides, about 150 to about 450 adenine nucleotides, about 150 to about 400 adenine nucleotides, about 150 to about 350 adenine nucleotides, about 150 to about 300 adenine nucleotides, about 150 to about 250 adenine nucleotides, about 150 to about 200 adenine nucleotides, about 200 to about 500 adenine nucleotides, about 200 to about 450 adenine nucleotides, about 200 to about 400 adenine nucleotides, about 200 to about 350 adenine nucleotides, about 200 to about 300 adenine nucleotides, about 250 to about 500 adenine nucleotides, about 250 to about 450 adenine nucleotides, about 250 to about 400 adenine nucleotides, about 250 to about 350 adenine nucleotides, or about 250 to about 300 adenine nucleotides or any intervening range of adenine nucleotides.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the pre-messenger (pre-mRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' A G T C A T G 3' is 3' T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

The term "nucleic acid cassette" or "expression cassette" as used herein refers to genetic sequences within the vector which can express an RNA, and subsequently a polypeptide. In one embodiment, the nucleic acid cassette contains a gene(s)-of-interest, e.g., a polynucleotide(s)-of-interest. In another embodiment, the nucleic acid cassette contains one or more expression control sequences, e.g., a promoter, enhancer, poly(A) sequence, and a gene(s)-of-interest, e.g., a polynucleotide(s)-of-interest. Vectors may comprise 1, 2, 3, 4, 5, 6, 7, 8, 9 or 10 or more nucleic acid cassettes. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In a preferred embodiment, the nucleic acid cassette contains the sequence of a therapeutic gene used to treat, prevent, or ameliorate a genetic disorder. The cassette can be removed and inserted into a plasmid or viral vector as a single unit.

Polynucleotides include polynucleotide(s)-of-interest. As used herein, the term "polynucleotide-of-interest" refers to a polynucleotide encoding a polypeptide or fusion polypeptide or a polynucleotide that serves as a template for the transcription of an inhibitory polynucleotide, as contemplated herein.

Moreover, it will be appreciated by those of ordinary skill in the art that, as a result of the degeneracy of the genetic code, there are many nucleotide sequences that may encode a polypeptide, or fragment of variant thereof, as contemplated herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. In one embodiment, polynucleotides comprising particular allelic sequences are provided. Alleles are endogenous polynucleotide sequences that are altered as a result of one or more mutations, such as deletions, additions and/or substitutions of nucleotides.

In a certain embodiment, a polynucleotide-of-interest comprises a donor repair template.

In a certain embodiment, a polynucleotide-of-interest comprises an inhibitory polynucleotide including, but not limited to, an siRNA, an miRNA, an shRNA, a ribozyme or another inhibitory RNA.

In one embodiment, a donor repair template comprising an inhibitory RNA comprises one or more regulatory sequences, such as, for example, a strong constitutive pol III, e.g., human or mouse U6 snRNA promoter, the human and mouse H1 RNA promoter, or the human tRNA-val promoter, or a strong constitutive pol II promoter, as described elsewhere herein.

The polynucleotides contemplated in particular embodiments, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, post-transcription response elements, and polynucleotides encoding self-cleaving polypeptides, epitope tags, as disclosed elsewhere herein or as known in the art, such that their overall length may vary considerably. It is therefore contemplated in particular embodiments that a polynucleotide fragment of almost any length may be employed, with the total length preferably being limited by the ease of preparation and use in the intended recombinant DNA protocol.

Polynucleotides can be prepared, manipulated, expressed and/or delivered using any of a variety of well-established techniques known and available in the art. In order to express a desired polypeptide, a nucleotide sequence encoding the polypeptide, can be inserted into appropriate vector. A desired polypeptide can also be expressed by delivering an mRNA encoding the polypeptide into the cell.

Illustrative examples of vectors include, but are not limited to plasmid, autonomously replicating sequences, and transposable elements, e.g., Sleeping Beauty, PiggyBac.

Additional illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include, but are not limited to pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally.

"Expression control sequences," "control elements," or "regulatory sequences" present in an expression vector are those non-translated regions of the vector-origin of replication, selection cassettes, promoters, enhancers, translation initiation signals (Shine Dalgarno sequence or Kozak sequence) introns, post-transcriptional regulatory elements, a polyadenylation sequence, 5' and 3' untranslated regions-which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In particular embodiments, a polynucleotide comprises a vector, including but not limited to expression vectors and viral vectors. A vector may comprise one or more exogenous, endogenous, or heterologous control sequences such as promoters and/or enhancers. An "endogenous control sequence" is one which is naturally linked with a given gene in the genome. An "exogenous control sequence" is one which is placed in juxtaposition to a gene by means of genetic manipulation (i.e., molecular biological techniques) such that transcription of that gene is directed by the linked enhancer/promoter. A "heterologous control sequence" is an exogenous sequence that is from a different species than the cell being genetically manipulated. A "synthetic" control sequence may comprise elements of one more endogenous and/or exogenous sequences, and/or sequences determined in vitro or in silico that provide optimal promoter and/or enhancer activity for the particular therapy.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, a short elongation factor 1-alpha (EF1a-short) promoter, a long elongation factor 1-alpha (EF1a-long) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., *Nature Biotechnology* 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted (MND) promoter (Challita et al., *J Virol.* 69(2):748-55 (1995)).

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene*, 323:67), the cumate inducible gene switch (WO 2002/088346), tetracycline-dependent regulatory systems, etc.

Conditional expression can also be achieved by using a site specific DNA recombinase.

According to certain embodiments, polynucleotides comprise at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, six, seven, eight, nine, ten or more.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments include, but are not limited to: Cre, Int, IHF, Xis, Flp, Fis, Hin, Gin, ΦC31, Cin, Tn3 resolvase, TndX, XerC, XerD, TnpX, Hjc, Gin, SpCCE1, and ParA.

The polynucleotides may comprise one or more recombination sites for any of a wide variety of site specific recombinases. It is to be understood that the target site for a site specific recombinase is in addition to any site(s) required for integration of a vector, e.g., a retroviral vector or lentiviral vector. As used herein, the terms "recombination sequence," "recombination site," or "site specific recombination site" refer to a particular nucleic acid sequence to which a recombinase recognizes and binds.

For example, one recombination site for Cre recombinase is loxP which is a 34 base pair sequence comprising two 13 base pair inverted repeats (serving as the recombinase binding sites) flanking an 8 base pair core sequence (see FIG. 1 of Sauer, B., *Current Opinion in Biotechnology* 5:521-527 (1994)). Other exemplary loxP sites include, but are not limited to: lox511 (Hoess et al., 1996; Bethke and Sauer, 1997), lox5171 (Lee and Saito, 1998), lox2272 (Lee and Saito, 1998), m2 (Langer et al., 2002), lox71 (Albert et al., 1995), and lox66 (Albert et al., 1995).

Suitable recognition sites for the FLP recombinase include, but are not limited to: FRT (McLeod, et al., 1996), $F_1$, $F_2$, $F_3$ (Schlake and Bode, 1994), $F_4$, $F_5$ (Schlake and Bode, 1994), FRT(LE) (Senecoff et al., 1988), FRT(RE) (Senecoff et al., 1988).

Other examples of recognition sequences are the attB, attP, attL, and attR sequences, which are recognized by the recombinase enzyme X Integrase, e.g., phi-c31. The φC31 SSR mediates recombination only between the heterotypic sites attB (34 bp in length) and attP (39 bp in length) (Groth et al., 2000). attB and attP, named for the attachment sites for the phage integrase on the bacterial and phage genomes, respectively, both contain imperfect inverted repeats that are likely bound by φC31 homodimers (Groth et al., 2000). The product sites, attL and attR, are effectively inert to further φC31-mediated recombination (Belteki et al., 2003), making the reaction irreversible. For catalyzing insertions, it has been found that attB-bearing DNA inserts into a genomic attP site more readily than an attP site into a genomic attB site (Thyagarajan et al., 2001; Belteki et al., 2003). Thus, typical strategies position by homologous recombination an attP-bearing "docking site" into a defined locus, which is then partnered with an attB-bearing incoming sequence for insertion.

In one embodiment, a polynucleotide contemplated herein comprises a donor repair template polynucleotide flanked by a pair of recombinase recognition sites. In particular embodiments, the repair template polynucleotide is flanked by LoxP sites, FRT sites, or att sites.

In particular embodiments, polynucleotides contemplated herein, include one or more polynucleotides-of-interest that encode one or more polypeptides. In particular embodiments, to achieve efficient translation of each of the plurality of polypeptides, the polynucleotide sequences can be separated by one or more IRES sequences or polynucleotide sequences encoding self-cleaving polypeptides.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. *RNA* 1(10):985-1000. Examples of IRES generally employed by those of skill in the art include those described in U.S. Pat. No. 6,692,736. Further examples of "IRES" known in the art include, but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. 1998. *Mol. Cell. Biol.* 18(11):6178-6190), the fibroblast growth factor 2 (FGF-2), and insulin-like growth factor (IGFII), the translational initiation factor eIF4G and yeast transcription factors TFIID and HAP4, the encephelomycarditis virus (EMCV) which is commercially available from Novagen (Duke et al., 1992. J. Virol 66(3):1602-9) and the VEGF IRES (Huez et al., 1998. Mol Cell Biol 18(11):6178-90). IRES have also been reported in viral genomes of Picornaviridae, Dicistroviridae and Flaviviridae species and in HCV, Friend murine leukemia virus (FrMLV) and Moloney murine leukemia virus (MoMLV).

In one embodiment, the IRES used in polynucleotides contemplated herein is an EMCV IRES.

In particular embodiments, the polynucleotides comprise polynucleotides that have a consensus Kozak sequence and that encode a desired polypeptide. As used herein, the term "Kozak sequence" refers to a short nucleotide sequence that greatly facilitates the initial binding of mRNA to the small subunit of the ribosome and increases translation. The consensus Kozak sequence is (GCC)RCCATGG, where R is a purine (A or G) (Kozak, 1986. *Cell.* 44(2):283-92, and Kozak, 1987. *Nucleic Acids Res.* 15(20):8125-48).

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The terms "polyA site," "polyA sequence," "poly(A) site" or "poly(A) sequence" as used herein denote a DNA sequence which directs both the termination and polyadenylation of the nascent RNA transcript by RNA polymerase II. Polyadenylation sequences can promote mRNA stability by addition of a poly(A) tail to the 3' end of the coding sequence and thus, contribute to increased translational efficiency. Efficient polyadenylation of the recombinant transcript is desirable as transcripts lacking a poly(A) tail are unstable and are rapidly degraded. Illustrative examples of poly(A) signals that can be used in a vector, includes an ideal poly(A) sequence (e.g., AATAAA, ATTAAA, AGTAAA), a bovine growth hormone poly(A) sequence (BGHpA), a rabbit β-globin poly(A) sequence (rβgpA), or another suitable heterologous or endogenous poly(A) sequence known in the art.

In some embodiments, a polynucleotide or cell harboring the polynucleotide utilizes a suicide gene, including an inducible suicide gene to reduce the risk of direct toxicity and/or uncontrolled proliferation. In specific embodiments, the suicide gene is not immunogenic to the host harboring the polynucleotide or cell. A certain example of a suicide gene that may be used is caspase-9 or caspase-8 or cytosine deaminase. Caspase-9 can be activated using a specific chemical inducer of dimerization (CID).

In certain embodiments, polynucleotides comprise gene segments that cause the genetically modified cells contemplated herein to be susceptible to negative selection in vivo. "Negative selection" refers to an infused cell that can be eliminated as a result of a change in the in vivo condition of the individual. The negative selectable phenotype may result from the insertion of a gene that confers sensitivity to an administered agent, for example, a compound. Negative selection genes are known in the art, and include, but are not limited to: the Herpes simplex virus type I thymidine kinase (HSV-I TK) gene which confers ganciclovir sensitivity; the cellular hypoxanthine phosphribosyltransferase (HPRT) gene, the cellular adenine phosphoribosyltransferase (APRT) gene, and bacterial cytosine deaminase.

In some embodiments, genetically modified cells comprise a polynucleotide further comprising a positive marker that enables the selection of cells of the negative selectable phenotype in vitro. The positive selectable marker may be a gene, which upon being introduced into the host cell, expresses a dominant phenotype permitting positive selection of cells carrying the gene. Genes of this type are known in the art, and include, but are not limited to hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

In one embodiment, the positive selectable marker and the negative selectable element are linked such that loss of the negative selectable element necessarily also is accompanied by loss of the positive selectable marker. In a particular embodiment, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See also the publications of PCT US91/08442 and PCT/US94/05601, by S. D. Lupton, describing the use of bifunctional selectable fusion genes derived from fusing a dominant positive selectable marker with a negative selectable marker.

Preferred positive selectable markers are derived from genes selected from the group consisting of hph, neo, and gpt, and preferred negative selectable markers are derived from genes selected from the group consisting of cytosine deaminase, HSV-I TK, VZV TK, HPRT, APRT and gpt. Exemplary bifunctional selectable fusion genes contemplated in particular embodiments include, but are not limited to genes wherein the positive selectable marker is derived from hph or neo, and the negative selectable marker is derived from cytosine deaminase or a TK gene or selectable marker.

In particular embodiments, polynucleotides may be introduced into hematopoietic cells, e.g., T cells, by both non-viral and viral methods. In particular embodiments, delivery of one or more polynucleotides may be provided by the same method or by different methods, and/or by the same vector or by different vectors.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. In particular embodiments, non-viral vectors are used to deliver one or more polynucleotides contemplated herein to a T cell.

Illustrative examples of non-viral vectors include, but are not limited to plasmids (e.g., DNA plasmids or RNA plasmids), transposons, cosmids, and bacterial artificial chromosomes.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

Illustrative examples of polynucleotide delivery systems suitable for use in particular embodiments contemplated in particular embodiments include, but are not limited to those provided by Amaxa Biosystems, Maxcyte, Inc., BTX Molecular Delivery Systems, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) *Gene Therapy.* 10:180-187; and Balazs et al. (2011) *Journal of Drug Delivery.* 2011:1-12. Antibody-targeted, bacterially derived, non-living nanocell-based delivery is also contemplated in particular embodiments.

Viral vectors comprising polynucleotides contemplated in particular embodiments can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., mobilized peripheral blood, lymphocytes, bone marrow aspirates, tissue biopsy, etc.) or universal donor hematopoietic stem cells, followed by reimplantation of the cells into a patient.

In one embodiment, viral vectors encoding a DNA donor repair template is administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Illustrative examples of viral vector systems suitable for use in particular embodiments contemplated herein include, but are not limited to adeno-associated virus (AAV), retrovirus, herpes simplex virus, adenovirus, and vaccinia virus vectors.

In various embodiments, a polynucleotide encoding a DNA donor repair template is introduced into a hematopoietic cell, e.g., a T cell, by transducing the cell with a recombinant adeno-associated virus (rAAV), comprising the polynucleotide.

AAV is a small (~26 nm) replication-defective, primarily episomal, non-enveloped virus. AAV can infect both dividing and non-dividing cells and may incorporate its genome into that of the host cell. Recombinant AAV (rAAV) are typically composed of, at a minimum, a transgene and its regulatory sequences, and 5' and 3' AAV inverted terminal repeats (ITRs). The ITR sequences are about 145 bp in length. In particular embodiments, the rAAV comprises ITRs and capsid sequences isolated from AAV1, AAV2, AAV3, AAV4, AAV5, AAV6, AAV7, AAV8, AAV9, or AAV10.

In some embodiments, a chimeric rAAV is used the ITR sequences are isolated from one AAV serotype and the capsid sequences are isolated from a different AAV serotype. For example, a rAAV with ITR sequences derived from AAV2 and capsid sequences derived from AAV6 is referred to as AAV2/AAV6. In particular embodiments, the rAAV vector may comprise ITRs from AAV2, and capsid proteins from any one of AAV1, AAV2, AAV3, AAV4, AAV5, AAV6, AAV7, AAV8, AAV9, or AAV10. In a preferred embodiment, the rAAV comprises ITR sequences derived from AAV2 and capsid sequences derived from AAV6. In a preferred embodiment, the rAAV comprises ITR sequences derived from AAV2 and capsid sequences derived from AAV2.

In some embodiments, engineering and selection methods can be applied to AAV capsids to make them more likely to transduce cells of interest.

Construction of rAAV vectors, production, and purification thereof have been disclosed, e.g., in U.S. Pat. Nos. 9,169,494; 9,169,492; 9,012,224; 8,889,641; 8,809,058; and 8,784,799, each of which is incorporated by reference herein, in its entirety.

In various embodiments, polynucleotides encoding a plurality of nuclease variants are introduced into a hematopoietic cell by electroporation and a donor repair template contemplated herein is introduced into a hematopoietic cell by transducing the cell with a retrovirus, e.g., lentivirus, comprising the donor repair template.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in particular embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

In various embodiments, a lentiviral vector contemplated herein comprises one or more LTRs, and one or more, or all, of the following accessory elements: a cPPT/FLAP, a Psi (Ψ) packaging signal, an export element, poly (A) sequences, and may optionally comprise a WPRE or HPRE, an insulator element, a selectable marker, and a cell suicide gene, as discussed elsewhere herein.

In particular embodiments, lentiviral vectors contemplated herein may be integrative or non-integrating or integration defective lentivirus. As used herein, the term "integration defective lentivirus" or "IDLV" refers to a lentivirus having an integrase that lacks the capacity to integrate the viral genome into the genome of the host cells. Integration-incompetent viral vectors have been described in patent application WO 2006/010834, which is herein incorporated by reference in its entirety.

Illustrative mutations in the HIV-1 pol gene suitable to reduce integrase activity include, but are not limited to: H12N, H12C, H16C, H16V, S81 R, D41A, K42A, H51A, Q53C, D55V, D64E, D64V, E69A, K71A, E85A, E87A, D116N, D116I, D116A, N120G, N120I, N120E, E152G, E152A, D35E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221 L, W235F, W235E, K236S, K236A, K246A, G247W, D253A, R262A, R263A and K264H.

In one embodiment, the HIV-1 integrase deficient pol gene comprises a D64V, D116I, D116A, E152G, or E152A mutation; D64V, D116I, and E152G mutations; or D64V, D116A, and E152A mutations.

In one embodiment, the HIV-1 integrase deficient pol gene comprises a D64V mutation.

The term "long terminal repeat (LTR)" refers to domains of base pairs located at the ends of retroviral DNAs which, in their natural sequence context, are direct repeats and contain U3, R and U5 regions.

As used herein, the term "FLAP element" or "cPPT/FLAP" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, *Cell*, 101:173. In another embodiment, a lentiviral vector contains a FLAP element with one or more mutations in the cPPT and/or CTS elements. In yet another embodiment, a lentiviral vector comprises either a cPPT or CTS element. In yet another embodiment, a lentiviral vector does not comprise a cPPT or CTS element.

As used herein, the term "packaging signal" or "packaging sequence" refers to psi [Ψ] sequences located within the retroviral genome which are required for insertion of the viral RNA into the viral capsid or particle, see e.g., Clever et al., 1995. *J. of Virology*, Vol. 69, No. 4; pp. 2101-2109.

The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. *J. Virol.* 65: 1053; and Cullen et al., 1991. *Cell* 58: 423), and the hepatitis B virus post-transcriptional regulatory element (HPRE).

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, *J. Virol.*, 73:2886); the posttranscriptional regulatory element present in hepatitis B virus (HPRE) (Huang et al., *Mol. Cell. Biol.*, 5:3864); and the like (Liu et al., 1995, *Genes Dev.*, 9:1766).

Lentiviral vectors preferably contain several safety enhancements as a result of modifying the LTRs. "Self-inactivating" (SIN) vectors refers to replication-defective vectors, e.g., in which the right (3') LTR enhancer-promoter region, known as the U3 region, has been modified (e.g., by deletion or substitution) to prevent viral transcription beyond the first round of viral replication. An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters.

The terms "pseudotype" or "pseudotyping" as used herein, refer to a virus whose viral envelope proteins have been substituted with those of another virus possessing preferable characteristics. For example, HIV can be pseudotyped with vesicular stomatitis virus G-protein (VSV-G) envelope proteins, which allows HIV to infect a wider range of cells because HIV envelope proteins (encoded by the env gene) normally target the virus to $CD4^+$ presenting cells.

In certain embodiments, lentiviral vectors are produced according to known methods. See e.g., Kutner et al., *BMC Biotechnol.* 2009; 9:10. doi: 10.1186/1472-6750-9-10; Kutner et al. *Nat. Protoc.* 2009; 4(4):495-505. doi: 10.1038/nprot.2009.22.

According to certain specific embodiments contemplated herein, most or all of the viral vector backbone sequences are derived from a lentivirus, e.g., HIV-1. However, it is to be understood that many different sources of retroviral and/or lentiviral sequences can be used, or combined and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, many of which may be adapted to produce a viral vector or transfer plasmid contemplated herein.

In various embodiments, polynucleotides encoding a plurality of nuclease variants are introduced into a hematopoietic cell by electroporation and a donor repair template contemplated herein is introduced into a hematopoietic cell by transducing the cell with an adenovirus comprising the donor repair template.

Adenoviral based vectors are capable of very high transduction efficiency in many cell types and do not require cell division. With such vectors, high titer and high levels of expression have been obtained. This vector can be produced in large quantities in a relatively simple system. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity.

Generation and propagation of the current adenovirus vectors, which are replication deficient, may utilize a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones & Shenk, 1978), the current adenovirus vectors, with the help of 293 cells, carry foreign DNA in either the E1, the D3 or both regions (Graham & Prevec, 1991). Adenovirus vectors have been used in eukaryotic gene expression (Levrero et al., 1991; Gomez-Foix et al., 1992) and vaccine development (Grunhaus & Horwitz, 1992; Graham & Prevec, 1992). Studies in administering recombinant adenovirus to different tissues include trachea instillation (Rosenfeld et al., 1991; Rosenfeld et al., 1992), muscle injection (Ragot et al., 1993), peripheral intravenous injections (Herz & Gerard, 1993) and stereotactic inoculation into the brain (Le Gal La Salle et al., 1993). An example of the use of an Ad vector in a clinical trial involved polynucleotide therapy for antitumor immunization with intramuscular injection (Sterman et al., *Hum. Gene Ther.* 7:1083-9 (1998)).

In various embodiments, polynucleotides encoding a plurality of nuclease variants are introduced into a hematopoietic cell by electroporation and a donor repair template contemplated herein is introduced into a hematopoietic cell by transducing the cell with a herpes simplex virus, e.g., HSV-1, HSV-2, comprising the donor repair template.

The mature HSV virion consists of an enveloped icosahedral capsid with a viral genome consisting of a linear double-stranded DNA molecule that is 152 kb. In one embodiment, the HSV based viral vector is deficient in one or more essential or non-essential HSV genes. In one embodiment, the HSV based viral vector is replication deficient. Most replication deficient HSV vectors contain a deletion to remove one or more intermediate-early, early, or late HSV genes to prevent replication. For example, the HSV vector may be deficient in an immediate early gene selected from the group consisting of: ICP4, ICP22, ICP27, ICP47, and a combination thereof. Advantages of the HSV vector are its ability to enter a latent stage that can result in long-term DNA expression and its large viral DNA genome that can accommodate exogenous DNA inserts of up to 25 kb. HSV-based vectors are described in, for example, U.S. Pat. Nos. 5,837,532, 5,846,782, and 5,804,413, and International Patent Applications WO 91/02788, WO 96/04394, WO 98/15637, and WO 99/06583, each of which are incorporated by reference herein in its entirety.

G. Genome Edited Cells

The genome edited cells manufactured by the methods contemplated in particular embodiments provide improved cellular therapy compositions.

In various embodiments, genome edite cell comprise hematopoietic stem or progenitor cells, e.g., CD34$^+$ cells. In particular embodiments, genome edited hematopoietic stem or progenitor cells comprise a plurality of edits in one, two, three or more genes that contribute to repression of γ-globin gene expression and HbF, including, but not limited to the BCL11A locus, the KLF1 locus, the SOX6 locus, the GATA1 locus, and the LSD1 locus; a thalassemic allele of a β-globin locus, or a sickling allele of a β-globin locus.

In particular embodiments, a method of editing multiple target sites in one or more hematopoietic stem or progenitor cells comprises introducing a plurality of engineered nucleases into the population of cells; transducing the population of cells with a vector comprising a donor repair template that comprises a plurality of pairs of homology arms corresponding to a plurality of target sites in a genome, wherein each pair of homology arms flanks one or more transgenes; wherein expression of the engineered nucleases create double strand breaks at target sites in a genome, and the homology arms of the donor repair template enable the incorporation of the one or more transgenes into the target sites by homology directed repair (HDR) at the site of the double-strand break (DSB).

In particular embodiments, a method of editing multiple target sites in one or more hematopoietic stem or progenitor cells comprises introducing a plurality of engineered nucleases into the population of cells; transducing the population of cells with a vector comprising a donor repair template that comprises a plurality of pairs of homology arms corresponding to a plurality of target sites in a genome, wherein each pair of homology arms flanks a different transgene; wherein expression of the engineered nucleases create double strand breaks at target sites in a genome, and the homology arms of the donor repair template enable the incorporation of the one or more transgenes into the target sites by homology directed repair (HDR) at the site of the double-strand break (DSB).

In particular embodiments, a method of editing multiple target sites in one or more hematopoietic stem or progenitor cells comprises introducing a plurality of engineered nucleases into the population of cells; transducing the population of cells with a vector comprising a donor repair template that comprises a plurality of pairs of homology arms corresponding to a plurality of target sites in a genome, wherein each pair of homology arms flanks one or more transgenes, wherein at least two of the pairs of homology arms flank the same transgene; wherein expression of the engineered nucleases create double strand breaks at target sites in a genome, and the homology arms of the donor repair template enable the incorporation of the one or more transgenes into the target sites by homology directed repair (HDR) at the site of the double-strand break (DSB).

In various embodiments, genome edited cells comprise immune effector cells, e.g., T cells, comprising a plurality of genome edits. Without wishing to be bound to any particular theory, it is believed that the multiplex genome edited immune effector cells manufactured by the methods contemplated herein are imbued with superior properties, including increased improved safety, efficacy, and durability in vivo.

In particular embodiments, genome edited cells comprise a plurality of edits in genes encoding a TCR signaling component (e.g., constant region of TCRα gene); an immune system checkpoint gene including, but not limited to: PD-1, LAG-3, TIM-3, CTLA-4, BTLA, TIGIT, VISTA, and KIR genes; or an immunosuppressive signaling component including, but not limited to: IL-10Rα, TGFβR1, TGFβR2, AHR, SGK1, TSC2, VHL, A2AR, and CBLB.

In particular embodiments, genome edited cells comprise an engineered antigen receptor inserted into at least two genomic target sites selected from the group consisting of: the constant region of TCRα gene, PD-1, LAG-3, TIM-3, CTLA-4, BTLA, TIGIT, VISTA, a KIR gene, IL-10Rα, TGFβR1, TGFβR2, AHR, SGK1, A2AR, TSC2, VHL, and CBLB.

In particular embodiments, genome edited cells comprise an engineered antigen receptor inserted into the constant region of TCRα gene and one of more genes selected from the group consisting of PD-1, LAG-3, TIM-3, CTLA-4, BTLA, TIGIT, VISTA, a KIR gene, IL-10Rα, TGFβR1, TGFβR2, AHR, SGK1, A2AR, TSC2, VHL, and CBLB.

In particular embodiments, a method of editing multiple target sites in one or more T cells comprises activating a population of T cells and stimulating the population of T cells to proliferate; introducing a plurality of engineered nucleases into the population of T cells; transducing the population of T cells with a vector comprising a donor repair template that comprises a plurality of pairs of homology arms corresponding to a plurality of target sites in a genome, wherein each pair of homology arms flanks one or more transgenes; wherein expression of the engineered nucleases create double strand breaks at target sites in a genome, and the homology arms of the donor repair template enable the incorporation of the one or more transgenes into the target sites by homology directed repair (HDR) at the site of the double-strand break (DSB).

In particular embodiments, a method of editing multiple target sites in one or more T cells comprises activating a population of T cells and stimulating the population of T cells to proliferate; introducing a plurality of engineered nucleases into the population of T cells; transducing the population of T cells with a vector comprising a donor repair template that comprises a plurality of pairs of homology arms corresponding to a plurality of target sites in a genome, wherein each pair of homology arms flanks a different transgene; wherein expression of the engineered nucleases create double strand breaks at target sites in a genome, and the homology arms of the donor repair template enable the incorporation of the one or more transgenes into the target sites by homology directed repair (HDR) at the site of the double-strand break (DSB).

In particular embodiments, a method of editing multiple target sites in one or more T cells comprises activating a population of T cells and stimulating the population of T cells to proliferate; introducing a plurality of engineered nucleases into the population of T cells; transducing the population of T cells with a vector comprising a donor repair template that comprises a plurality of pairs of homology arms corresponding to a plurality of target sites in a genome, wherein each pair of homology arms flanks one or more transgenes, wherein at least two of the pairs of homology arms flank the same transgene; wherein expression of the engineered nucleases create double strand breaks at target sites in a genome, and the homology arms of the donor repair template enable the incorporation of the one or more transgenes into the target sites by homology directed repair (HDR) at the site of the double-strand break (DSB).

H. Compositions and Formulations

The compositions contemplated in particular embodiments may comprise one or more polypeptides, polynucleotides, vectors comprising same, and genome editing compositions and genome edited cell compositions, as contemplated herein. The genome editing compositions and methods contemplated in particular embodiments are useful for editing multiple target sites in a cell or a population of cells using a single DNA donor repair template. In preferred embodiments, engineered nucleases and a DNA donor repair template are used to introduce multiple edits in a genome of a hematopoietic cell, e.g., a hematopoietic stem or progenitor cell, a CD34$^+$ cell, a T cell, or an immune effector cell.

In particular embodiments, the compositions contemplated herein comprise a DNA donor repair template.

In particular embodiments, the compositions contemplated herein comprise a vector encoding a DNA donor repair template.

In various embodiments, the compositions contemplated herein comprise an engineered nuclease and/or a DNA donor repair template. The nuclease variant may be in the form of an mRNA that is introduced into a cell via polynucleotide delivery methods disclosed herein, e.g., electroporation, lipid nanoparticles, transduction etc. In one embodiment, a composition comprising an mRNA encoding a homing endonuclease variant or megaTAL, and a DNA donor repair template, is introduced in a cell via polynucleotide delivery methods disclosed herein. Expression of the gene editing enzymes in the presence of the donor repair template can be used to introduce genome edits at multiple target sites in a genome edited cell or population of genome edited cells by HDR. In particular embodiments, the population of cells comprise genetically modified immune effector cells.

Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the composition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" refers to a diluent, adjuvant, excipient, or vehicle with which the therapeutic cells are administered. Illustrative examples of pharmaceutical carriers can be sterile liquids, such as cell culture media, water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients in particular embodiments, include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Except insofar as any conventional media or agent is incompatible with the active ingredient, its use in the therapeutic compositions is contemplated. Supplementary active ingredients can also be incorporated into the compositions.

In one embodiment, a composition comprising a pharmaceutically acceptable carrier is suitable for administration to a subject. In particular embodiments, a composition comprising a carrier is suitable for parenteral administration, e.g., intravascular (intravenous or intraarterial), intraperitoneal or intramuscular administration. In particular embodiments, a composition comprising a pharmaceutically acceptable carrier is suitable for intraventricular, intraspinal, or intrathecal administration. Pharmaceutically acceptable carriers include sterile aqueous solutions, cell culture media, or dispersions. The use of such media and agents for pharmaceutically active substances is well known in the art. Except insofar as any conventional media or agent is incompatible with the transduced cells, use thereof in the pharmaceutical compositions is contemplated.

In particular embodiments, compositions contemplated herein comprise genetically modified T cells and a pharmaceutically acceptable carrier. A composition comprising a cell-based composition contemplated herein can be administered separately by enteral or parenteral administration methods or in combination with other suitable compounds to effect the desired treatment goals.

The pharmaceutically acceptable carrier must be of sufficiently high purity and of sufficiently low toxicity to render it suitable for administration to the human subject being treated. It further should maintain or increase the stability of the composition. The pharmaceutically acceptable carrier can be liquid or solid and is selected, with the planned manner of administration in mind, to provide for the desired bulk, consistency, etc., when combined with other components of the composition. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions contemplated herein include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers contemplated herein include, but are not limited to, Dulbecco's phosphate buffered saline (PBS), Ringer's solution, 5% dextrose in water (D5W), normal/physiologic saline (0.9% NaCl).

The pharmaceutically acceptable carriers may be present in amounts sufficient to maintain a pH of the composition of about 7. Alternatively, the composition has a pH in a range from about 6.8 to about 7.4, e.g., 6.8, 6.9, 7.0, 7.1, 7.2, 7.3, and 7.4. In still another embodiment, the composition has a pH of about 7.4.

Compositions contemplated herein may comprise a nontoxic pharmaceutically acceptable medium. The compositions may be a suspension. The term "suspension" as used herein refers to non-adherent conditions in which cells are not attached to a solid support. For example, cells maintained as a suspension may be stirred or agitated and are not adhered to a support, such as a culture dish.

In particular embodiments, compositions contemplated herein are formulated in a suspension, where the genome edited cells are dispersed within an acceptable liquid medium or solution, e.g., saline or serum-free medium, in an intravenous (IV) bag or the like. Acceptable diluents include, but are not limited to water, PlasmaLyte, Ringer's solution, isotonic sodium chloride (saline) solution, serum-free cell culture medium, and medium suitable for cryogenic storage, e.g., Cryostor® medium.

In certain embodiments, a pharmaceutically acceptable carrier is substantially free of natural proteins of human or animal origin, and suitable for storing a composition comprising a population of genome edited cells. The therapeutic composition is intended to be administered into a human patient, and thus is substantially free of cell culture components such as bovine serum albumin, horse serum, and fetal bovine serum.

In some embodiments, compositions are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions includes, but is not limited to QBSF-60 (Quality Biological, Inc.), StemPro-34 (Life Technologies), and X-VIVO 10.

In a preferred embodiment, the compositions comprising genome edited cells are formulated in PlasmaLyte.

In various embodiments, compositions comprising genome edited cells are formulated in a cryopreservation medium. For example, cryopreservation media with cryopreservation agents may be used to maintain a high cell viability outcome post-thaw. Illustrative examples of cryopreservation media used in particular compositions includes, but is not limited to, CryoStor CS10, CryoStor CS5, and CryoStor CS2.

In one embodiment, the compositions are formulated in a solution comprising 50:50 PlasmaLyte A to CryoStor CS10.

In particular embodiments, the composition is substantially free of *mycoplasma*, endotoxin, and microbial contamination. By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells. In particular embodiments, compositions comprising hematopoietic stem or progenitor cells transduced with a retroviral vector contemplated herein contain about 0.5 EU/mL to about 5.0 EU/mL, or about 0.5 EU/mL, 1.0 EU/mL, 1.5 EU/mL, 2.0 EU/mL, 2.5 EU/mL, 3.0 EU/mL, 3.5 EU/mL, 4.0 EU/mL, 4.5 EU/mL, or 5.0 EU/mL.

In certain embodiments, compositions and formulations suitable for the delivery of polynucleotides are contemplated including, but not limited to, one or more mRNAs encoding one or more reprogrammed nucleases, and optionally end-processing enzymes.

Exemplary formulations for ex vivo delivery may also include the use of various transfection agents known in the art, such as calcium phosphate, electroporation, heat shock and various liposome formulations (i.e., lipid-mediated transfection). Liposomes, are lipid bilayers entrapping a fraction of aqueous fluid. DNA spontaneously associates to the external surface of cationic liposomes (by virtue of its charge) and these liposomes will interact with the cell membrane.

In particular embodiments, formulation of pharmaceutically-acceptable carrier solutions is well-known to those of skill in the art, as is the development of suitable dosing and treatment regimens for using the particular compositions described herein in a variety of treatment regimens, including e.g., enteral and parenteral, e.g., intravascular, intravenous, intrarterial, intraosseously, intraventricular, intracerebral, intracranial, intraspinal, intrathecal, and intramedullary administration and formulation. It would be understood by the skilled artisan that particular embodiments contemplated herein may comprise other formulations, such as those that are well known in the pharmaceutical art, and are described, for example, in *Remington: The Science and Practice of Pharmacy*, volume I and volume II. 22$^{nd}$ Edition. Edited by Loyd V. Allen Jr. Philadelphia, Pa.: Pharmaceutical Press; 2012, which is incorporated by reference herein, in its entirety.

I. Genome Edited Cell Therapies

Genome edited cells manufactured by the compositions and methods contemplated herein provide improved drug products for use in the prevention, treatment, or amelioration of at least one symptom of a hemoglobinopathy, cancer, GVHD, an infectious disease, an autoimmune disease, an inflammatory disease, or an immunodeficiency. As used herein, the term "drug product" refers to genetically modified cells produced using the compositions and methods contemplated herein.

In particular embodiments, the drug product comprises genetically edited hematopoietic stem or progenitor cells or CD34$^+$ cells. In particular embodiments, an effective amount of genome edited hematopoietic stem or progenitor cells or CD34$^+$ cells comprising multiple edits in a genome are administered to a subject to prevent, treat, or ameliorate at least one symptom of a hemoglobinopathy, including but not limited to, β-thalassemia and sickle cell disease.

In particular embodiments, the drug product comprises genetically edited immune effector cells or T cells. Moreover, the genome edited T cells contemplated in particular embodiments provide safer and more efficacious adoptive cell therapies because they are resistant to T cell exhaustion and display increased durability and persistence in the tumor microenvironment that can lead to sustained therapy.

In particular embodiments, an effective amount of genome edited immune effector cells or T cells comprising multiple edits in a genome are administered to a subject to prevent, treat, or ameliorate at least one symptom of a cancer, GVHD, an infectious disease, an autoimmune disease, an inflammatory disease, or an immunodeficiency.

In particular embodiments, the genome edited cells comprise one or more immunopotency enhancers, immunosuppressive signal dampers, or engineered antigen receptors inserted into multiple target sites in genes that increase resistance to T cell exhaustion, increase T cell durability in vivo, and/or increase T cell persistence in vivo.

In particular embodiments, the genome edited cells comprise a CAR inserted into multiple target sites selected from the group consisting of the TCRα constant region, immune system checkpoint genes, and/or genes encoding immunosuppressive signaling components.

In particular embodiments, the genome edited cells comprise a CAR inserted into a TCRα constant region and one or more transgenes encoding an immunopotency enhancer, an immunosuppressive signal damper, or another engineered antigen receptor into one or more immune system checkpoint genes, and/or genes encoding immunosuppressive signaling components.

In particular embodiments, the genome edited cells comprise a CAR or flip receptor inserted into a TCRα constant region, one or more immune system checkpoint genes, and/or genes encoding immunosuppressive signaling components.

In particular embodiments, the genome edited cells comprise one or more flip receptors inserted into a TCRα constant region, one or more immune system checkpoint genes, and/or genes encoding immunosuppressive signaling components.

In particular embodiments, genome edited cells contemplated herein are used in the treatment of solid tumors or cancers.

In particular embodiments, genome edited cells contemplated herein are used in the treatment of solid tumors or cancers including, but not limited to: adrenal cancer, adrenocortical carcinoma, anal cancer, appendix cancer, astrocytoma, atypical teratoid/rhabdoid tumor, basal cell carcinoma, bile duct cancer, bladder cancer, bone cancer, brain/CNS cancer, breast cancer, bronchial tumors, cardiac tumors, cervical cancer, cholangiocarcinoma, chondrosarcoma, chordoma, colon cancer, colorectal cancer, craniopharyngioma, ductal carcinoma in situ (DCIS) endometrial cancer, ependymoma, esophageal cancer, esthesioneuroblastoma, Ewing's sarcoma, extracranial germ cell tumor, extragonadal germ cell tumor, eye cancer, fallopian tube cancer, fibrous histiosarcoma, fibrosarcoma, gallbladder cancer, gastric cancer, gastrointestinal carcinoid tumors, gastrointestinal stromal tumor (GIST), germ cell tumors, glioma, glioblastoma, head and neck cancer, hemangioblastoma, hepatocellular cancer, hypopharyngeal cancer, intraocular melanoma, kaposi sarcoma, kidney cancer, laryngeal cancer, leiomyosarcoma, lip cancer, liposarcoma, liver cancer, lung cancer, non-small cell lung cancer, lung carcinoid tumor, malignant mesothelioma, medullary carcinoma, medulloblastoma, menangioma, melanoma, Merkel cell carcinoma, midline tract carcinoma, mouth cancer, myxosarcoma, myelodysplastic syndrome, myeloproliferative neoplasms, nasal cavity and paranasal sinus cancer, nasopharyngeal cancer, neuroblastoma, oligodendroglioma, oral cancer, oral cavity cancer, oropharyngeal cancer, osteosarcoma, ovarian cancer, pancreatic cancer, pancreatic islet cell tumors, papillary carcinoma, paraganglioma, parathyroid cancer, penile cancer, pharyngeal cancer, pheochromocytoma, pinealoma, pituitary tumor, pleuropulmonary blastoma, primary peritoneal cancer, prostate cancer, rectal cancer, retinoblastoma, renal cell carcinoma, renal pelvis and ureter cancer, rhabdomyosarcoma, salivary gland cancer, sebaceous gland carcinoma, skin cancer, soft tissue sarcoma, squamous cell carcinoma, small cell lung cancer, small intestine cancer, stomach cancer, sweat gland carcinoma, synovioma, testicular cancer, throat cancer, thymus cancer, thyroid cancer, urethral cancer, uterine cancer, uterine sarcoma, vaginal cancer, vascular cancer, vulvar cancer, and Wilms Tumor.

In particular embodiments, genome edited cells contemplated herein are used in the treatment of solid tumors or cancers including, without limitation, liver cancer, pancreatic cancer, lung cancer, breast cancer, bladder cancer, brain cancer, bone cancer, thyroid cancer, kidney cancer, or skin cancer.

In particular embodiments, genome edited cells contemplated herein are used in the treatment of various cancers including but not limited to pancreatic, bladder, and lung.

In particular embodiments, genome edited cells contemplated herein are used in the treatment of liquid cancers or hematological cancers.

In particular embodiments, genome edited cells contemplated herein are used in the treatment of B-cell malignancies, including but not limited to: leukemias, lymphomas, and multiple myeloma.

In particular embodiments, genome edited cells contemplated herein are used in the treatment of liquid cancers including, but not limited to leukemias, lymphomas, and multiple myelomas: acute lymphocytic leukemia (ALL), acute myeloid leukemia (AML), myeloblastic, promyelocytic, myelomonocytic, monocytic, erythroleukemia, hairy cell leukemia (HCL), chronic lymphocytic leukemia (CLL), and chronic myeloid leukemia (CMIL), chronic myelomonocytic leukemia (CMML) and polycythemia vera, Hodgkin lymphoma, nodular lymphocyte-predominant Hodgkin lymphoma, Burkitt lymphoma, small lymphocytic lymphoma (SLL), diffuse large B-cell lymphoma, follicular lymphoma, immunoblastic large cell lymphoma, precursor B-lymphoblastic lymphoma, mantle cell lymphoma, marginal zone lymphoma, mycosis fungoides, anaplastic large cell lymphoma, Sezary syndrome, precursor T-lymphoblastic lymphoma, multiple myeloma, overt multiple myeloma, smoldering multiple myeloma, plasma cell leukemia, non-secretory myeloma, IgD myeloma, osteosclerotic myeloma, solitary plasmacytoma of bone, and extramedullary plasmacytoma.

Preferred cells for use in the genome editing methods contemplated herein include autologous/autogeneic ("self") cells, preferably hematopoietic cells.

In particular embodiments, methods comprising administering a therapeutically effective amount of genome edited cells contemplated herein or a composition comprising the same, to a patient in need thereof, alone or in combination with one or more therapeutic agents, are provided. In certain embodiments, the cells are used in the treatment of patients at risk for developing a hemoglobinopathy, cancer, GVHD, an infectious disease, an autoimmune disease, an inflammatory disease, or an immunodeficiency. Thus, particular embodiments comprise the treatment or prevention or amelioration of at least one symptom of a hemoglobinopathy, cancer, an infectious disease, an autoimmune disease, an inflammatory disease, or an immunodeficiency comprising administering to a subject in need thereof, a therapeutically effective amount of the genome edited cells contemplated herein.

In one embodiment, a method of treating a hemoglobinopathy, cancer, GVHD, an infectious disease, an autoimmune disease, an inflammatory disease, or an immunodeficiency in a subject in need thereof comprises administering an effective amount, e.g., therapeutically effective amount of a composition comprising genome edited cells contemplated herein. The quantity and frequency of administration will be determined by such factors as the condition of the patient, and the type and severity of the patient's disease, although appropriate dosages may be determined by clinical trials.

In one illustrative embodiment, the effective amount of genome edited cells provided to a subject is at least $2\times10^6$ cells/kg, at least $3\times10^6$ cells/kg, at least $4\times10^6$ cells/kg, at least $5\times10^6$ cells/kg, at least $6\times10^6$ cells/kg, at least $7\times10^6$ cells/kg, at least $8\times10^6$ cells/kg, at least $9\times10^6$ cells/kg, or at least $10\times10^6$ cells/kg, or more cells/kg, including all intervening doses of cells.

In another illustrative embodiment, the effective amount of genome edited cells provided to a subject is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, or about $10\times10^6$ cells/kg, or more cells/kg, including all intervening doses of cells.

In another illustrative embodiment, the effective amount of genome edited cells provided to a subject is from about $2\times10^6$ cells/kg to about $10\times10^6$ cells/kg, about $3\times10^6$ cells/kg to about $10\times10^6$ cells/kg, about $4\times10^6$ cells/kg to about $10\times10^6$ cells/kg, about $5\times10^6$ cells/kg to about $10\times10^6$ cells/kg, $2\times10^6$ cells/kg to about $6\times10^6$ cells/kg, $2\times10^6$ cells/kg to about $7\times10^6$ cells/kg, $2\times10^6$ cells/kg to about $8\times10^6$ cells/kg, $3\times10^6$ cells/kg to about $6\times10^6$ cells/kg, $3\times10^6$ cells/kg to about $7\times10^6$ cells/kg, $3\times10^6$ cells/kg to about $8\times10^6$ cells/kg, $4\times10^6$ cells/kg to about $6\times10^6$ cells/kg, $4\times10^6$ cells/kg to about $7\times10^6$ cells/kg, $4\times10^6$ cells/kg to about $8\times10^6$ cells/kg, $5\times10^6$ cells/kg to about $6\times10^6$ cells/kg, $5\times10^6$ cells/kg to about $7\times10^6$ cells/kg, $5\times10^6$ cells/kg to about $8\times10^6$ cells/kg, or $6\times10^6$ cells/kg to about $8\times10^6$ cells/kg, including all intervening doses of cells.

One of ordinary skill in the art would recognize that multiple administrations of the compositions contemplated in particular embodiments may be required to effect the desired therapy. For example a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated T cells to a subject and then subsequently redraw blood (or have an apheresis performed), activate T cells therefrom, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, 100 cc, 150 cc, 200 cc, 250 cc, 300 cc, 350 cc, or 400 cc or more. Not to be bound by theory, using this multiple blood draw/multiple reinfusion protocol may serve to select out certain populations of T cells.

The administration of the compositions contemplated in particular embodiments may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

In one embodiment, a method of treating a subject diagnosed with a hemoglobinopathy, comprises removing peripheral blood cells or bone marrow cells from the subject, editing the genome of said cells and producing a population of genome edited hematopoietic stem or progenitor cells, and administering the population of genome edited cells to the same subject. In a preferred embodiment, the immune effector cells comprise CD34$^+$ cells.

In one embodiment, a method of treating a subject diagnosed with a cancer, comprises removing immune effector cells from the subject, editing the genome of said immune effector cells and producing a population of genome edited immune effector cells, and administering the population of genome edited immune effector cells to the same subject. In a preferred embodiment, the immune effector cells comprise T cells.

The methods for administering the cell compositions contemplated in particular embodiments include any method which is effective to result in reintroduction of ex vivo genome edited cells or on reintroduction of the genome edited progenitors of cells that on introduction into a subject differentiate into mature cells. One method comprises genome editing peripheral blood cells or bone marrow cells ex vivo and returning the transduced cells into the subject.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Figure 3A:
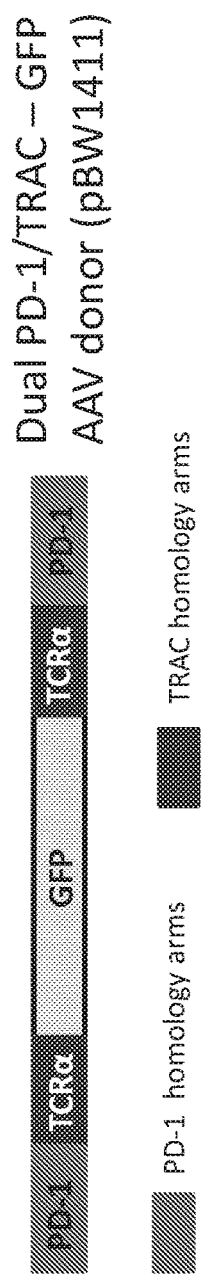
FIG. 3A shows a representative design of a single AAV donor repair template that simultaneously targets the PD-1 gene and TCRα constant region.

Targeted Integration of a Transgene into Two Different Loci Using a Single AAV HDR DNA Donor Repair Template Adeno-associated virus (AAV) plasmids comprising a promoter, a transgene encoding a green fluorescent protein, and a polyadenylation signal (SEQ ID NO: 1) were designed and constructed. The integrity of AAV ITR elements was confirmed with XmaI digest. The transgene cassette was flanked by regions of homology to the human program death receptor 1 (PD-1) and the constant region of the T cell receptor alpha (TCRα) genes. The PD-1 homology arms contained 300 bp regions flanking a megaTAL cleavage site in PD-1 exon 1. The TCRα homology arms contained 300 bp regions flanking a megaTAL cleavage site in the constant region of TCRα gene. The homology arms were placed in series, resulting in TCRα homology arms being placed immediately 5' and 3' of a transgene cassette while the PD-1 homolog arms were located immediately 5' and 3' of TCRα homology arms (FIG. 3A). Exemplary transgene expression cassettes contained a myeloproliferative sarcoma virus enhancer, negative control region deleted, d1587rev primer-binding site substituted (MND) promoter operably linked to a polynucleotide encoding a fluorescent polypeptide, e.g., blue fluorescent protein (BFP), red fluorescent protein (RFP), cyan fluorescent protein (CFP), green fluorescent protein (GFP), etc. The expression cassettes also contained the SV40 late polyadenylation signal.

Recombinant AAV (rAAV) was prepared by transiently co-transfecting HEK 293T cells with one or more plasmids providing the replication, capsid, and adenoviral helper elements necessary. rAAV was purified from the co-transfected HEK 293T cell culture using ultracentrifugation in an iodixanol-based gradient.

MegaTAL-induced homologous recombination was evaluated in primary human T cells activated with CD3 and CD28 and cultured in complete media supplemented with IL-2. After 3 days, T cells were washed and electroporated with in vitro transcribed mRNA encoding a megaTAL targeting exon 1 of the PD-1 gene, a megaTAL targeting the constant region of the TCRα gene or both megaTALs simultaneously. T cells were subsequently transduced with a purified recombinant AAV targeting vector comprising a DNA donor repair template encoding a MND-GFP transgene cassette. Controls included T cells treated with rAAV targeting vector alone. Flow cytometry was used at multiple time points to measure the frequency of T cells expressing the fluorescent protein and to differentiate transient expression of the fluorescent protein of the non-integrated rAAV targeting vector. MegaTAL-mediated TCRα disruption was detected by staining for CD3 expression while disruption of the PD-1 gene was detected by sequencing and the loss of PD-1 expression following polyclonal T cell activation.

Figure 3B:
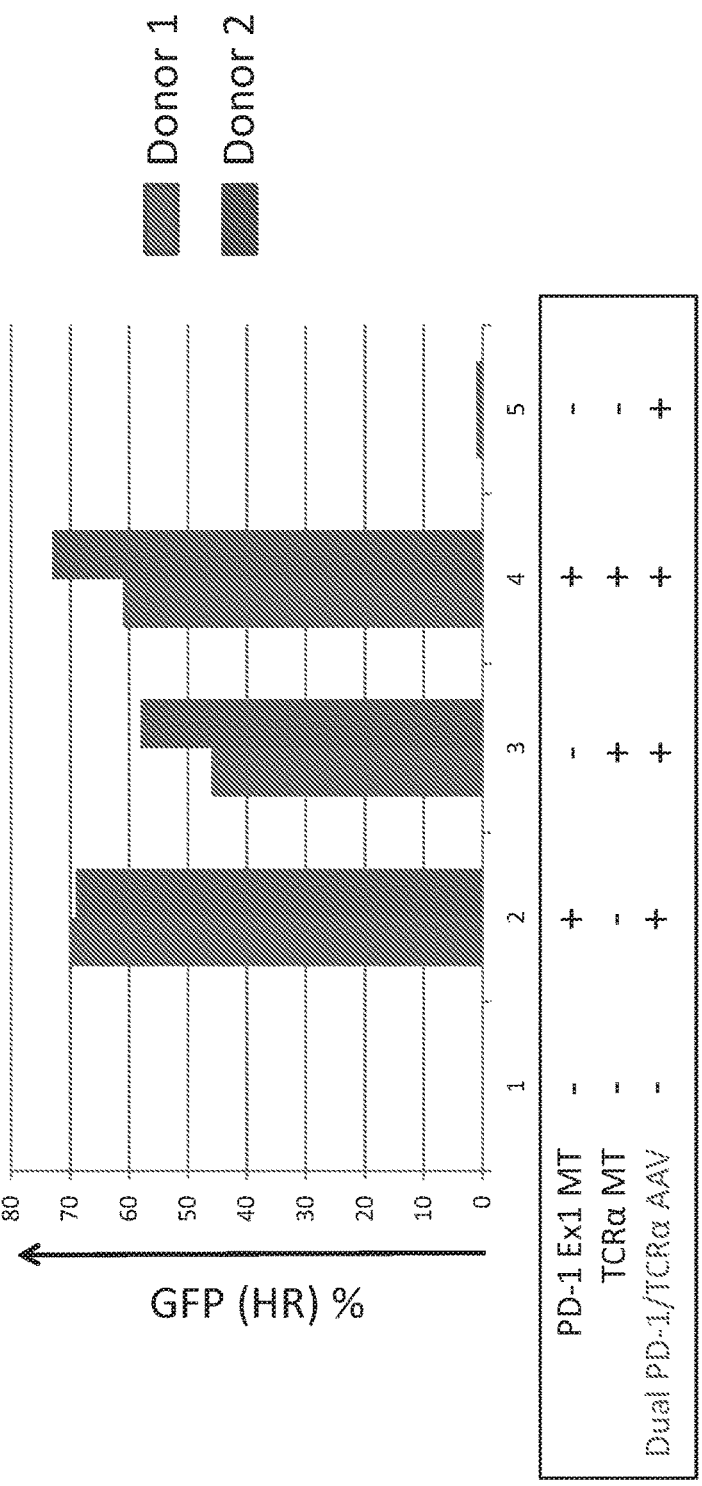
FIG. 3B shows the results of a homology directed repair experiment using PD-1 and TCRα megaTALs and a single AAV donor repair template that simultaneously targets the PD-1 gene and the TCRα constant region to introduce a polynucleotide sequence encoding GFP.
Figure 4:
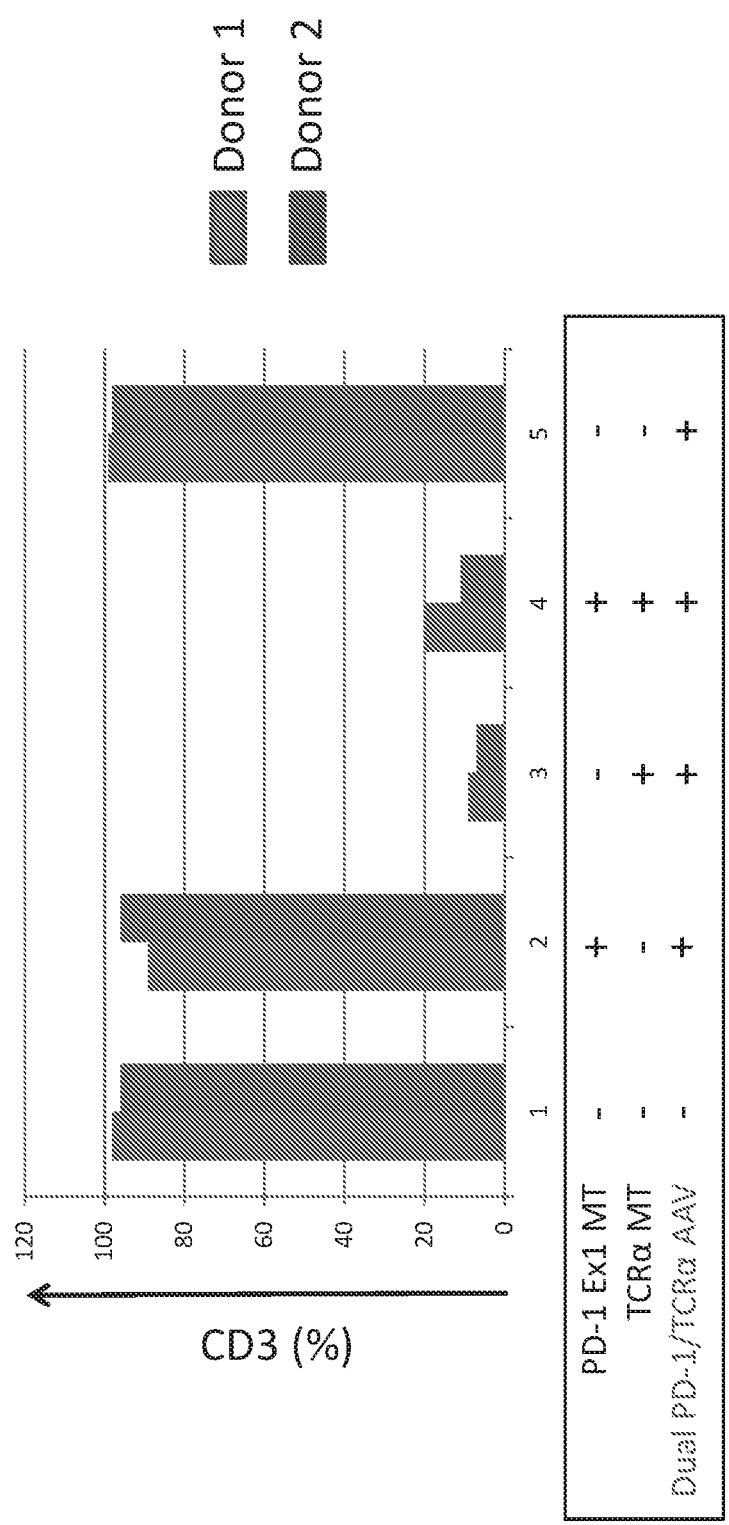
FIG. 4 shows knock-out efficiency of TCRα constant region, as measured by lack of CD3 expression. A TCRα megaTAL alone or together with a PD-1 megaTAL showed over 80% of knock-out efficiency (lanes 3 and 4).
Figure 5:
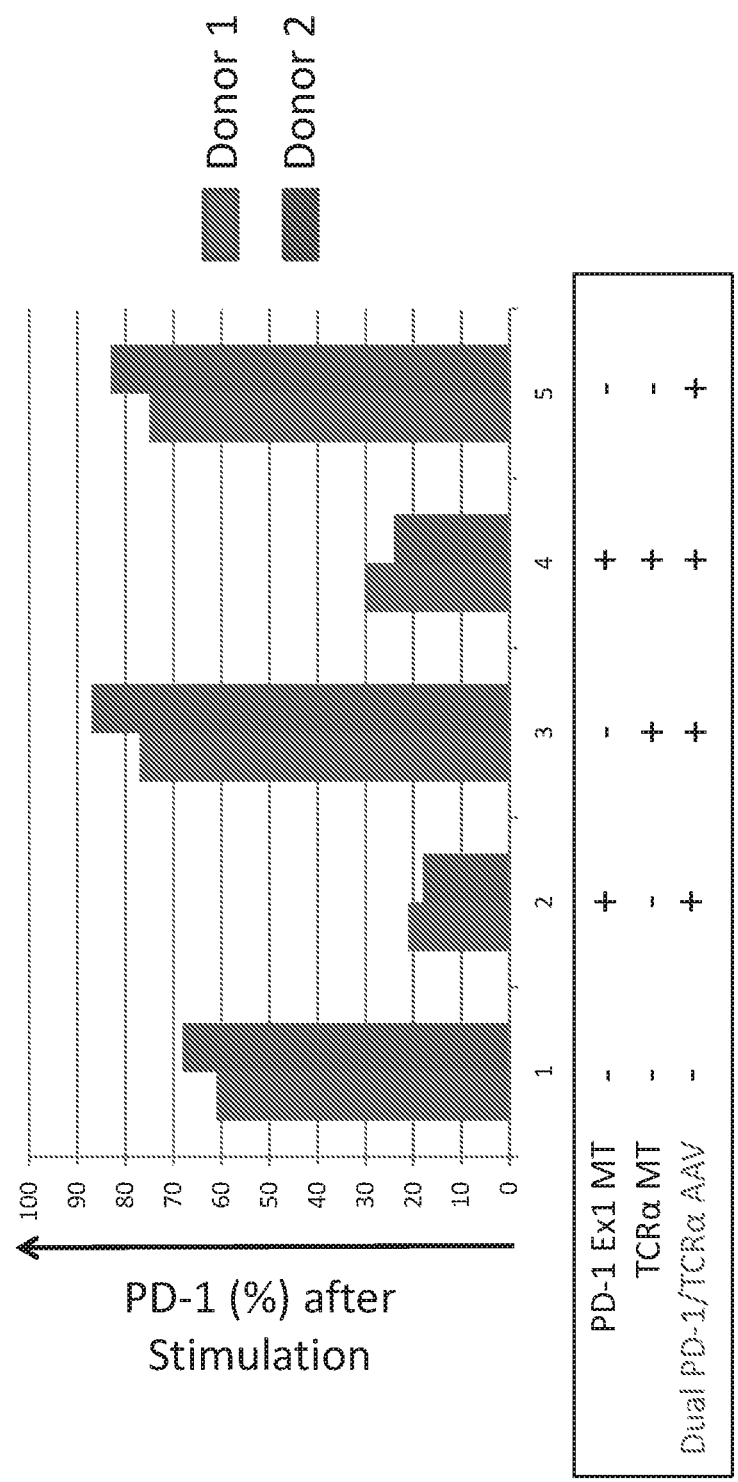
FIG. 5 shows decreased PD-1 expression in PD-1 megaTAL treated cells after PMA/ionomycin stimulation for 24 hours (lanes 2 and 4) compared to cells that were not treated with a PD-1 megaTAL (lanes 1, 3, and 5).

Long-term transgene expression was observed in 40-70% of the T cells that were treated with megaTAL(s) and the rAAV targeting vector (FIG. 3B). Control samples produced variable levels of transient fluorescent protein expression and very low levels (<1%) of long-term fluorescent protein expression, consistent with minimal random integration into the genome. MegaTAL-mediated disruption of TCRα gene ranged between 70-90% (FIG. 4) while megaTAL-mediated disruption of the PD-1 locus ranged from 60% to 80% (FIG. 5). Cleavage at each locus was independent, and combining megaTALs targeting PD-1 and TCRα did not substantially impact cleavage rates at PD-1 or TCRα target sites using either megaTAL alone. Similar homologous recombination rates were observed at either PD-1 or TCRα loci with the same rAAV homology template. Combined treatment with PD-1 and TCRα megaTALs together with rAAV template produced 60-70% stable GFP expression, with increased variability of GFP expression. The increased variability of GFP expression is indicative of a more heterogenous transgene integration pattern in two distinct genetic locations. Results were confirmed in experiments performed on T cells isolated from several independent donors.

Example 2

Figure 6A:
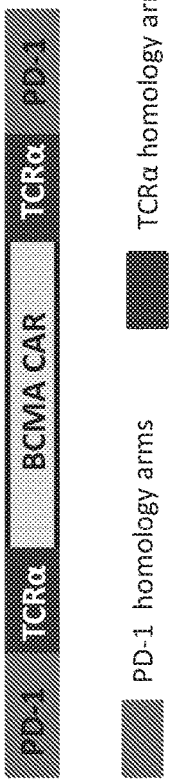
FIG. 6A shows a representative design of a single AAV donor repair template that simultaneously targets the PD-1 gene and TCRα constant region.

Targeted Integration of a BCMA-Specific Chimeric Antigen Receptor into Two Different Loci Using a Single AAV HDR DNA Donor Repair Template Adeno-associated virus (AAV) plasmids containing a promoter, a transgene encoding a chimeric antigen receptor (CAR), and a polyadenylation signal (SEQ ID NO: 2) were designed, constructed, and verified. The CAR expression cassette contained an MND promoter operably linked to a CAR comprising a CD8α-derived signal peptide, a single-chain variable fragment (scFV) targeting the B cell maturation antigen (BCMA), a CD8α derived hinge region and transmembrane domain, an intracellular 4-1BB co-stimulatory domain, and a CD3 zeta signaling domain. The homology arms were placed in series, resulting in TCRα homology arms being placed immediately 5' and 3' of the transgene cassette while the PD-1 homolog arms were located immediately 5' and 3' of TCRα homology arms (FIG. 6A).

Primary human T cells were activated with CD3 and CD28, as described in Example 1. MegaTAL-induced homology directed repair of the PD-1 and TCRα gene using an AAV donor repair template encoding an anti-BCMA CAR evaluated using activated primary human T cells electroporated with in vitro transcribed mRNA encoding a megaTAL targeting exon 1 of the PD-1 gene, a megaTAL targeting the constant region of the TCRα gene or both megaTALs simultaneously. Electroporated T cells were transduced with an AAV targeting vector comprising a DNA donor repair template encoding an anti-BCMA CAR and cultured in the presence of IL2 at 30° C. overnight and then transferred to 37° C. CAR staining was performed 7 days after electroporation (10 day total culture). Controls included T cells containing megaTAL or AAV treatments alone. Anti-BCMA-CAR expression was analyzed by flow cytometry by staining with PE-conjugated BCMA-Fc.

Figure 6B:
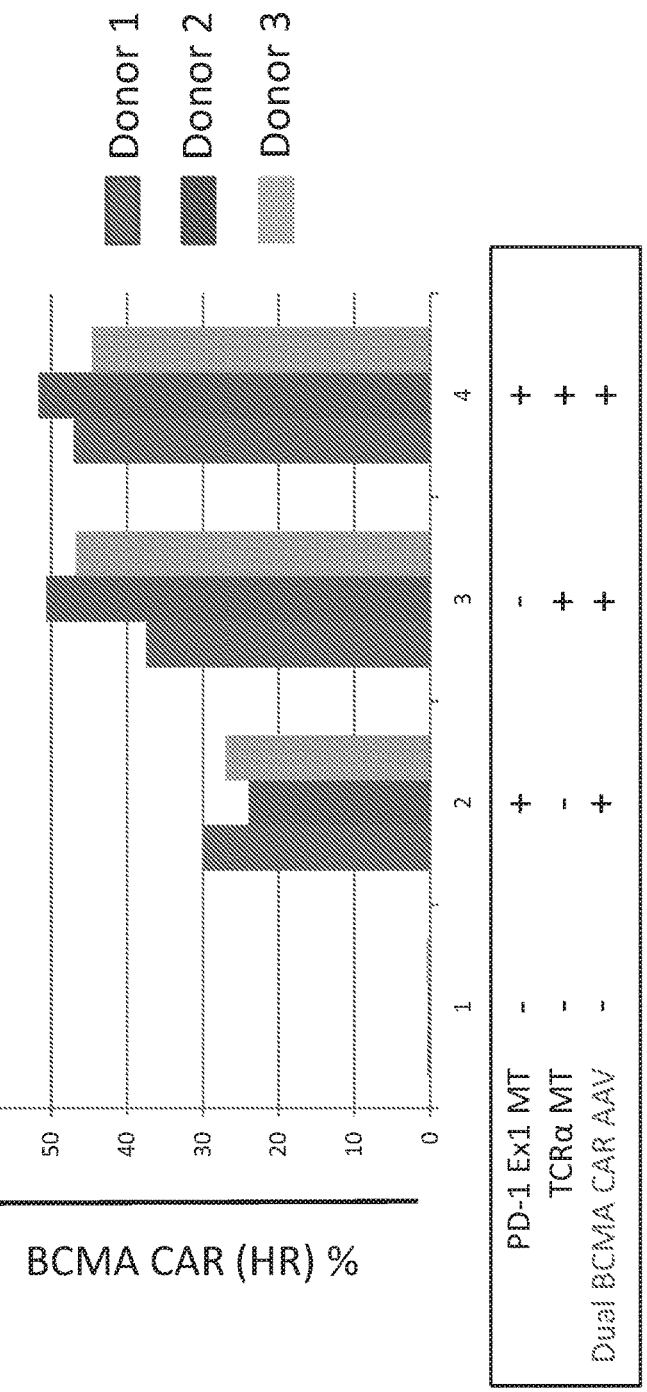
FIG. 6B shows the results of a homology directed repair experiment using PD-1 and TCRα megaTALs and a single AAV donor repair template that simultaneously targets the PD-1 gene and the TCRα constant region to introduce a polynucleotide sequence encoding a BCMA CAR.
Figure 7:
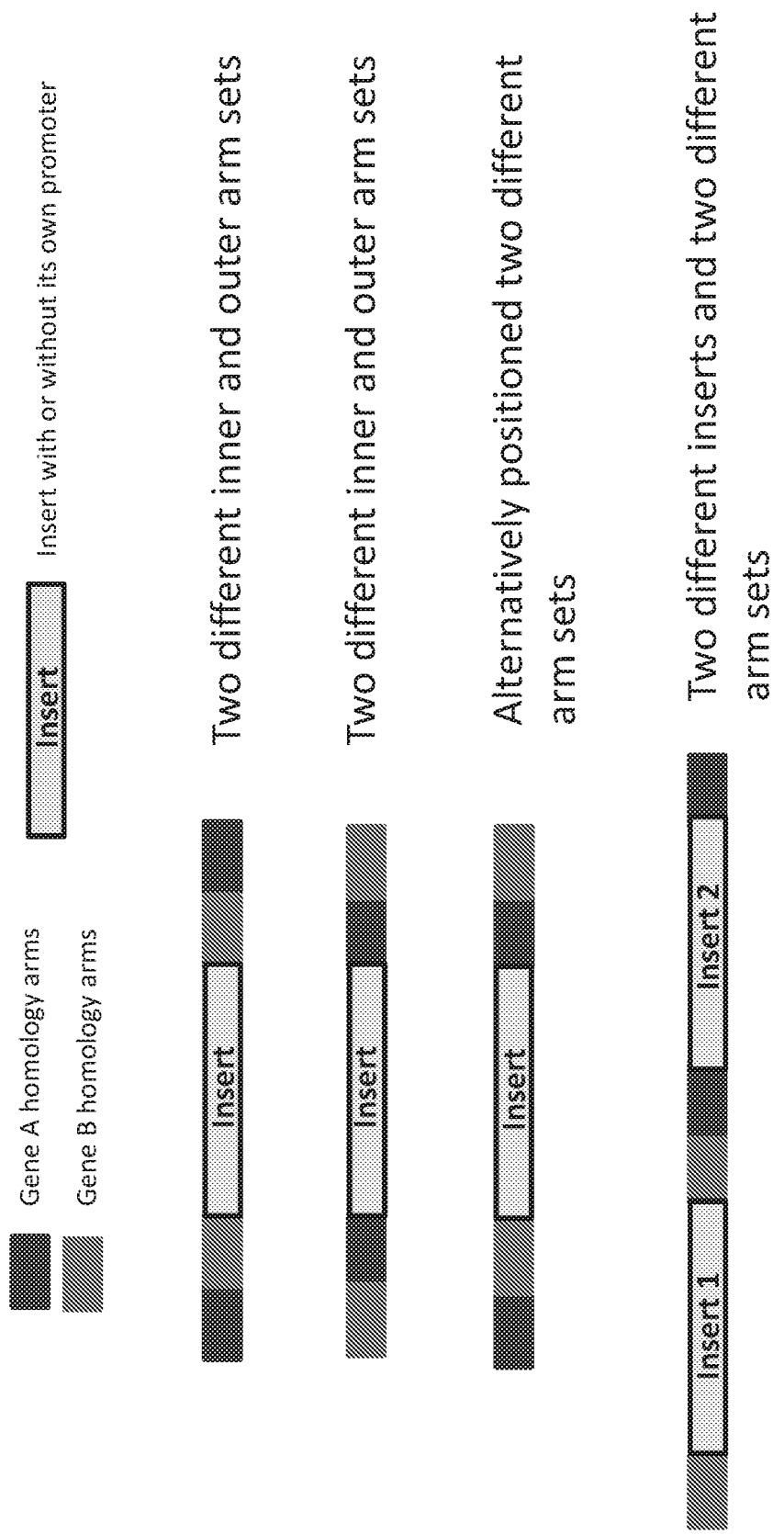
FIG. 7 shows representative embodiments of dual AAV donors. A single insert or two different inserts can be used for a dual AAV donor. Positions and orientations of insert and homology arms can have various combinations depending on usages. The number of different homology arms can be increased for targeting multiple target loci with a single AAV donor.

T cells treated with PD-1-targeting megaTAL mRNA and rAAV DNA donor repair template encoding an anti-BCMA CAR showed CAR expression in 20-30% of total cells, while cells treated with TCRα-targeting megaTAL and rAAV DNA donor repair template encoding an anti-BCMA CAR showed CAR expression in 30-50% of total cells. Combined treatment with both PD-1 and TCRα megaTALs resulted in anti-BCMA CAR expression in 40-55% of the cells (FIG. 6B). More variation in CAR expression was observed in cells treated with both PD-1 and TCRα targeting megaTAL, indicative of a more heterogenous transgene integration pattern in two distinct genetic locations. Similar rates of T cell expansion and a similar T cell phenotype was observed between untreated, AAV-treated and megaTAL/rAAV anti-BCMA CAR-treated T cells.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A DNA donor repair template comprising from 5' to 3':
   (a) a 5' homology arm homologous to a DNA sequence 5' of a first target site;
   (b) a 5' homology arm homologous to a DNA sequence 5' of a second target site;
   (c) a transgene;
   (d) a 3' homology arm homologous to a DNA sequence 3' of the second target site; and
   (e) a 3' homology arm homologous to a DNA sequence 3' of the first target site.

2. The DNA donor repair template of claim 1, wherein the lengths of the 5' and 3' homology arms to the first target site and/or the second target site are independently selected from about 100 bp to about 500 bp.

3. The DNA donor repair template of claim 1, wherein the first target site and the second target site are in different genes.

4. The DNA donor repair template of claim 1, wherein the first target site or the second target site comprises an engineered nuclease cleavage site in a TCRα gene or in an immune system checkpoint gene.

5. The DNA donor repair template of claim 1, wherein the first target site is a first engineered nuclease cleavage site in a TCRα gene and the second target site is a second engineered nuclease cleavage site in an immune system checkpoint gene.

6. The DNA donor repair template of claim 4 or claim 5, wherein the immune system checkpoint gene is selected from the group consisting of: programmed cell death protein 1 (PD-1), lymphocyte activation gene 3 protein (LAG-3), T cell immunoglobulin domain and mucin domain protein 3 (TIM-3), cytotoxic T lymphocyte antigen-4 (CTLA-4), band T lymphocyte attenuator (BTLA), T cell immunoglobulin and immunoreceptor tyrosine-based inhibitory motif domain (TIGIT), V-domain Ig suppressor of T cell activation (VISTA), and killer cell immunoglobulin-like receptor (KIR) genes.

7. The DNA donor repair template of claim 1, wherein the first target site is a first engineered nuclease cleavage site in a first immune system checkpoint gene and the second target site is a second engineered nuclease cleavage site in a second immune system checkpoint gene.

8. The DNA donor repair template of claim 7, wherein the first and second immune system checkpoint genes are independently selected from the group consisting of: programmed cell death protein 1 (PD-1), lymphocyte activation gene 3 protein (LAG-3), T cell immunoglobulin domain and mucin domain protein 3 (TIM-3), cytotoxic T lymphocyte antigen-4 (CTLA-4), band T lymphocyte attenuator (BTLA), T cell immunoglobulin and immunoreceptor tyrosine-based inhibitory motif domain (TIGIT), V-domain Ig suppressor of T cell activation (VISTA), and killer cell immunoglobulin-like receptor (KIR) genes.

9. The DNA donor repair template of claim 1, wherein the first target site is an engineered nuclease cleavage site in a TCRα gene and the second target site is an engineered nuclease cleavage site in an immune system checkpoint gene or a gene that encodes an immunosuppressive signaling component.

10. The DNA donor repair template claim 9, wherein the gene that encodes an immunosuppressive signaling component is independently selected from the group consisting of: interleukin receptor 10 alpha, transforming growth factor β receptor I (TGFβRI), transforming growth factor β receptor II (TGFβRII), aryl hydrocarbon receptor (AHR), serum and glucocorticoid-regulated kinase 1 (SGK1), tuberous sclerosis complex 2 (TSC2), von Hippel-Lindau tumor suppressor (VHL), adenosine A2a receptor (A2AR), and Cbl proto-oncogene B (CBLB).

11. The DNA donor repair template of claim 1, wherein the first target site is an engineered nuclease cleavage site in a first immune system checkpoint gene or a gene that encodes an immunosuppressive signaling component and the second target site is an engineered nuclease cleavage site in a second immune system checkpoint gene or a gene that encodes an immunosuppressive signaling component.

12. The DNA donor repair template claim 11, wherein the gene that encodes an immunosuppressive signaling component is independently selected from the group consisting of: interleukin receptor 10 alpha, transforming growth factor β receptor I (TGFβRI), transforming growth factor β receptor II (TGFβRII), aryl hydrocarbon receptor (AHR), serum and glucocorticoid-regulated kinase 1 (SGK1), tuberous sclerosis complex 2 (TSC2), von Hippel-Lindau tumor suppressor (VHL), adenosine A2a receptor (A2AR), and Cbl proto-oncogene B (CBLB).

13. The DNA donor repair template of claim 1, wherein the transgene comprises a polynucleotide encoding an engineered antigen receptor.

14. The DNA donor repair template of claim 13, wherein the transgene comprises a polynucleotide encoding a CAR.

15. A viral vector comprising the DNA donor repair template of claim 1.

16. The viral vector of claim 15, wherein the viral vector is a recombinant adeno-associated viral vector (rAAV) or a retrovirus.

17. The viral vector of claim 16, wherein the rAAV has one or more ITRs from AAV2.

18. A cell comprising the DNA donor repair template of claim 1.

19. A cell comprising the viral vector of claim 15.

* * * * *